US012667269B2

(12) United States Patent
Gunn et al.

(10) Patent No.: US 12,667,269 B2
(45) Date of Patent: Jun. 30, 2026

(54) INTRAOCULAR PHYSIOLOGICAL SENSOR

(71) Applicant: GLAUKOS CORPORATION, San Clemente, CA (US)

(72) Inventors: Nicholas Gunn, Newport Beach, CA (US); Andrew Johnson, San Clemente, CA (US); David S. Haffner, Mission Viejo, CA (US); Cesario Dos Santos, Newport Beach, CA (US)

(73) Assignee: GLAUKOS CORPORATION, Aliso Viejo, CA (US)

( * ) Notice: Subject to any disclaimer, the term of this patent is extended or adjusted under 35 U.S.C. 154(b) by 209 days.

(21) Appl. No.: 18/339,820

(22) Filed: Jun. 22, 2023

(65) Prior Publication Data

US 2023/0329571 A1      Oct. 19, 2023

Related U.S. Application Data

(63) Continuation of application No. 16/832,246, filed on Mar. 27, 2020, now Pat. No. 11,701,019.

(60) Provisional application No. 62/824,707, filed on Mar. 27, 2019.

(51) Int. Cl.
| | |
|---|---|
| *A61B 5/03* | (2006.01) |
| *A61B 5/00* | (2006.01) |
| *A61B 5/145* | (2006.01) |

(52) U.S. Cl.
CPC ............. *A61B 5/03* (2013.01); *A61B 5/0002* (2013.01); *A61B 5/14532* (2013.01); *A61B 5/6821* (2013.01); *A61B 5/6882* (2013.01); *A61B 2562/0214* (2013.01); *A61B 2562/0247* (2013.01)

(58) Field of Classification Search
CPC .... A61B 2562/0214; A61B 2562/0247; A61B 5/0002; A61B 5/03; A61B 5/14532; A61B 5/6821; A61B 5/6882; A61B 3/16; A61B 5/0031; A61F 2250/0001; A61F 2250/0002; A61F 9/00736
See application file for complete search history.

(56) References Cited

U.S. PATENT DOCUMENTS

| | | | | | |
|---|---|---|---|---|---|
| 4,220,386 A | * | 9/1980 | Kenny | ................. | H01B 7/0009 |
| | | | | | 439/948 |
| 4,548,205 A | * | 10/1985 | Armeniades | ........ | A61F 9/00736 |
| | | | | | 600/561 |
| 2006/0111753 A1 | * | 5/2006 | Imran | .................. | A61N 1/0509 |
| | | | | | 607/40 |

(Continued)

OTHER PUBLICATIONS

Supplementary European Search Report for EP Application No. 20778896 dated Nov. 23, 2022 (9 pages).

(Continued)

*Primary Examiner* — Eric J Messersmith
(74) *Attorney, Agent, or Firm* — K&L Gates LLP

(57) ABSTRACT

Intraocular physiological sensor implants include a physiological sensor, and a housing comprising a faceplate. The physiological sensor is integrated with the faceplate. The physiological sensor typically comprises an intraocular pressure sensor, such as a capacitive pressure sensor that may further include a flexible diaphragm electrode spaced apart from a counter electrode. The intraocular pressure sensor detects intraocular pressure, to identify patient conditions such as glaucoma.

17 Claims, 37 Drawing Sheets

280

514

500

(56) References Cited

U.S. PATENT DOCUMENTS

| | | | |
|---|---|---|---|
| 2008/0217752 A1 | 9/2008 | Hata et al. | |
| 2010/0170346 A1 | 7/2010 | Opitz et al. | |
| 2010/0282910 A1 | 11/2010 | Stothers et al. | |
| 2012/0032632 A1 | 2/2012 | Soar | |
| 2013/0090534 A1* | 4/2013 | Burns | G16H 10/60 |
| | | | 600/398 |
| 2013/0289467 A1 | 10/2013 | Haffner et al. | |
| 2014/0116122 A1 | 5/2014 | Lammel et al. | |
| 2014/0171777 A1 | 6/2014 | Sanchez et al. | |
| 2014/0296687 A1 | 10/2014 | Irazoqui et al. | |
| 2016/0000344 A1 | 1/2016 | Cao | |
| 2016/0058324 A1* | 3/2016 | Cao | A61B 5/7282 |
| | | | 600/302 |
| 2018/0325373 A1 | 11/2018 | Rodger et al. | |
| 2019/0053704 A1 | 2/2019 | Burns et al. | |

OTHER PUBLICATIONS

International Search Report and Written Opinion for related International Application No. PCT/US2020/025365; report dated Jun. 12, 2020 (15 pages).

International Preliminary Report on Patentability for elated International Application No. PCT/US2020/025365; report dated Sep. 28, 2021 (8 pages).

* cited by examiner

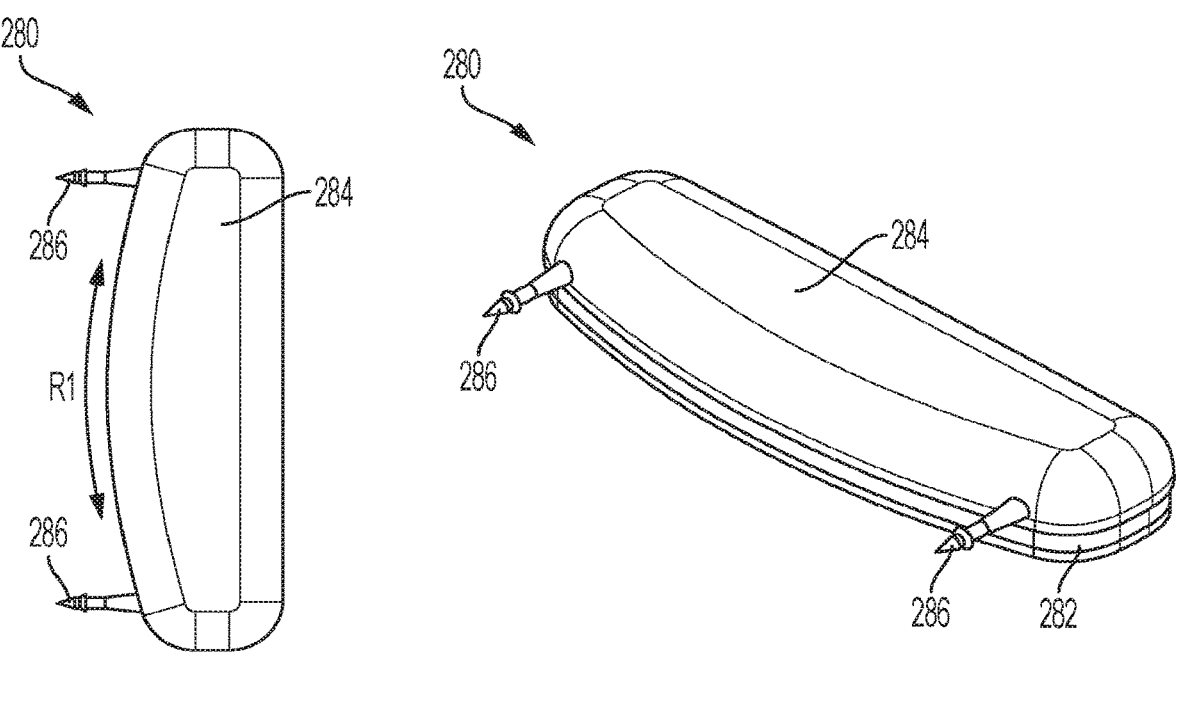
FIG. 4A
FIG. 4B
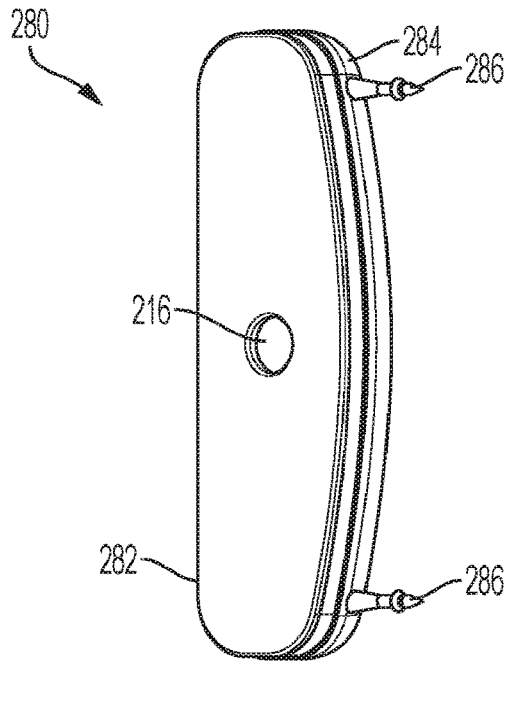
FIG. 4C

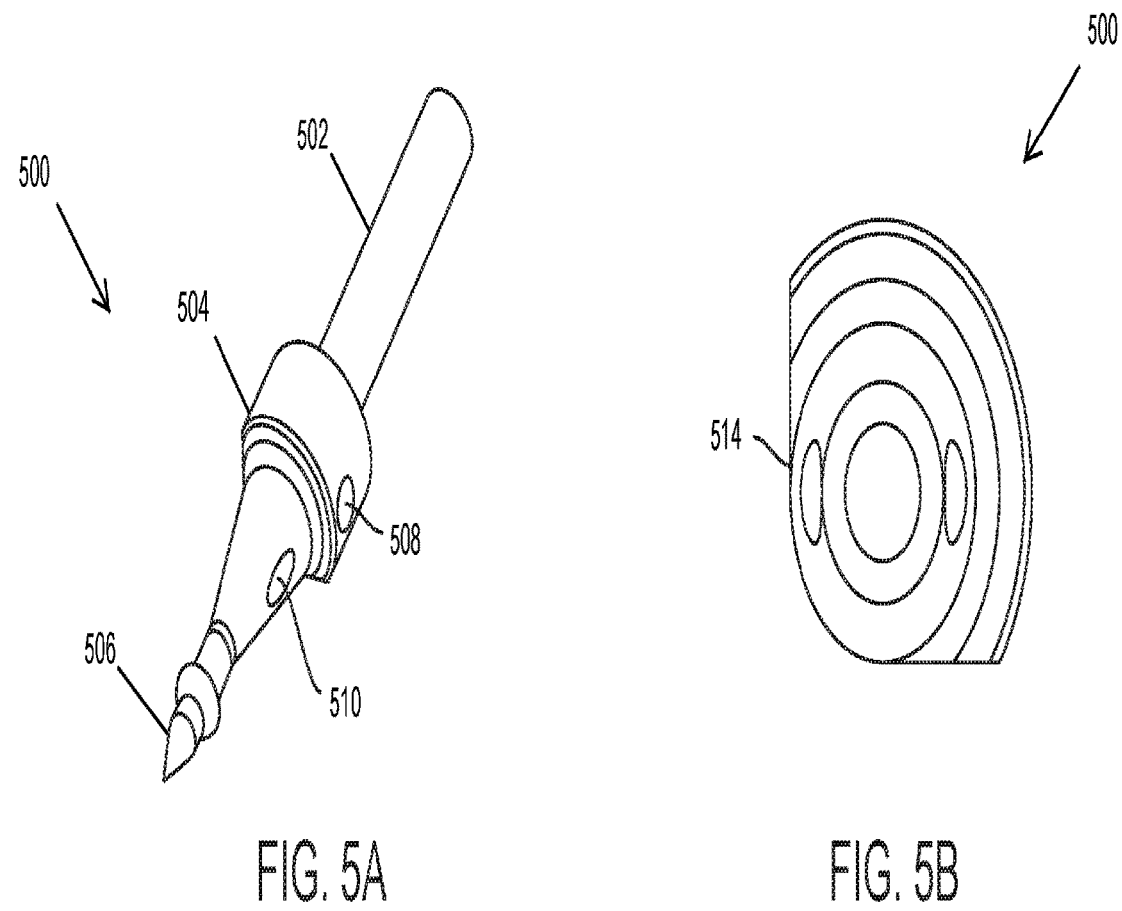
FIG. 5A
FIG. 5B
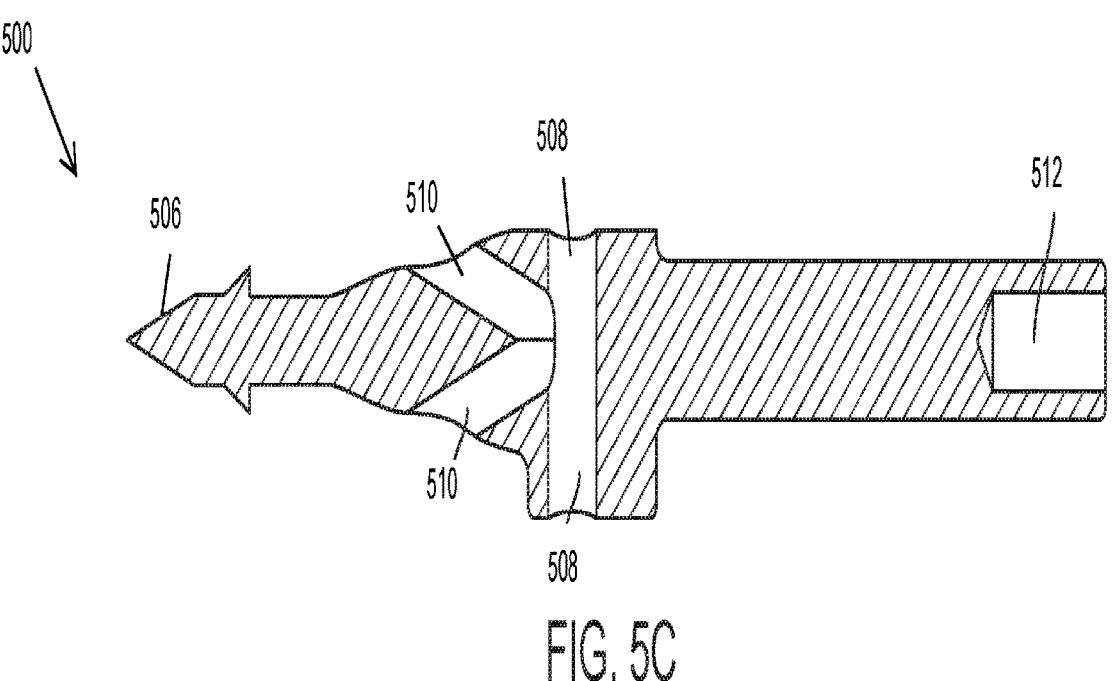
FIG. 5C

280

514

514

280

270

288

282

SEE FIG. 7D

260

273

219a    217    216    218    720    710

210

720        722        262        260

912

*284*

*282*        *288*

*288* propagation direction of flame reaction zone

1014 reacted solidification | melting zone | solder layer ignition-spark 1010
material B unreacted
multilayer stack 1012
material A brazing solder

1014

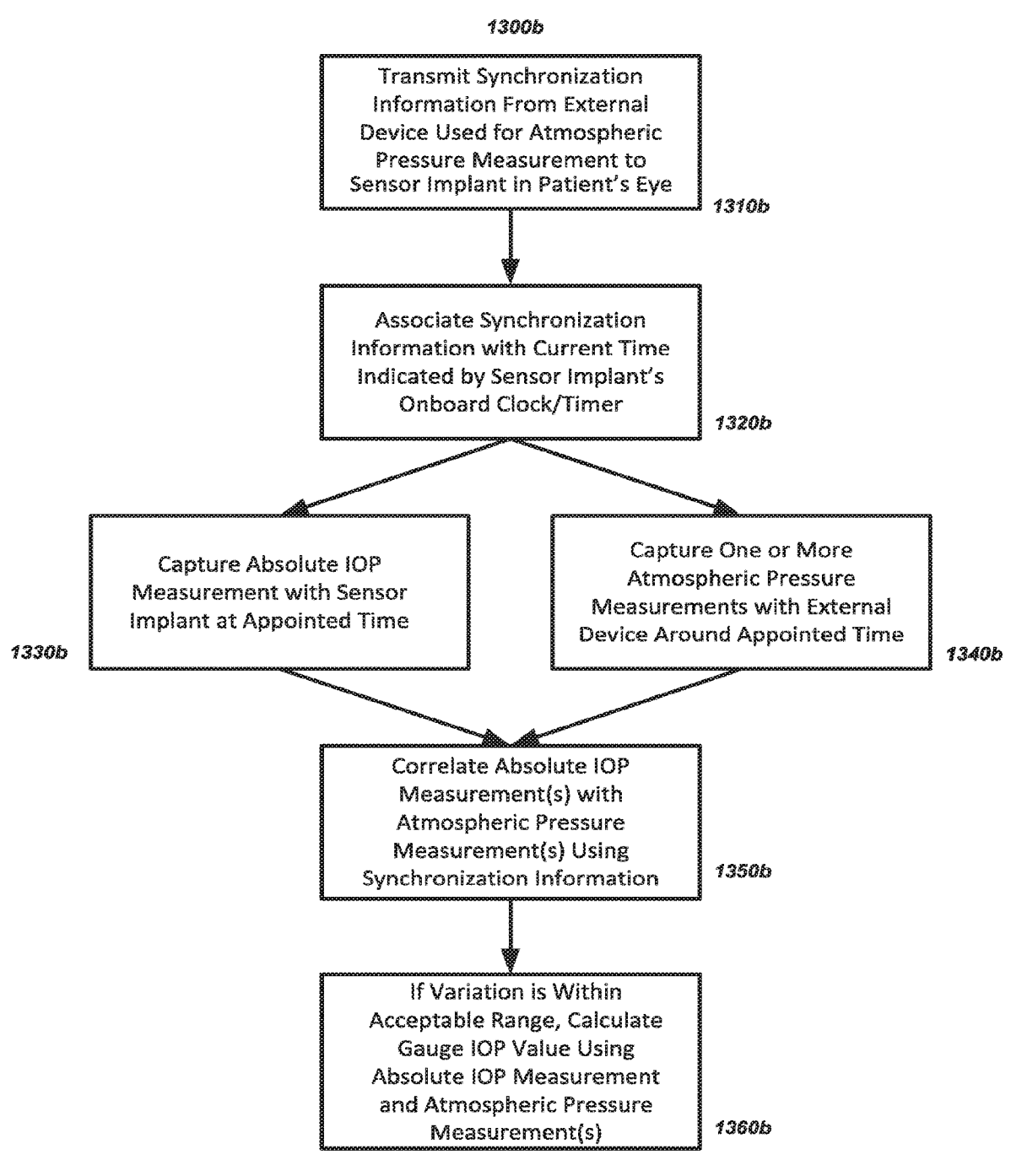

*1300b*

Transmit Synchronization Information From External Device Used for Atmospheric Pressure Measurement to Sensor Implant in Patient's Eye
*1310b*

Associate Synchronization Information with Current Time Indicated by Sensor Implant's Onboard Clock/Timer
*1320b*

Capture Absolute IOP Measurement with Sensor Implant at Appointed Time
*1330b*

Capture One or More Atmospheric Pressure Measurements with External Device Around Appointed Time
*1340b*

Correlate Absolute IOP Measurement(s) with Atmospheric Pressure Measurement(s) Using Synchronization Information
*1350b*

If Variation is Within Acceptable Range, Calculate Gauge IOP Value Using Absolute IOP Measurement and Atmospheric Pressure Measurement(s)
*1360b*

FIG. 13B

INTRAOCULAR PHYSIOLOGICAL SENSOR

PRIORITY CLAIM AND CROSS-REFERENCE TO RELATED APPLICATION

This application is a continuation of U.S. patent application Ser. No. 16/832,246, filed Mar. 27, 2020, which claims priority to U.S. Provisional Patent Application No. 62/824,707 filed on Mar. 27, 2019, entitled "INTRAOCULAR PHYSIOLOGICAL SENSOR," the entire contents of which are incorporated by reference herein and relied upon.

BACKGROUND

Field

The field of the invention generally relates to implantable physiological sensors. In particular, embodiments of the invention generally relate to implantable intraocular sensors for measuring physiological characteristics such as intraocular pressure and/or glucose concentration.

Description of the Related Art

Some diseases, including glaucoma, diabetes, and others, can be more effectively treated if they are diagnosed early and/or monitored effectively. Glaucoma, for example, is a leading cause of blindness. This disease damages the optic nerve in the eye due to elevated intraocular pressure, which can lead to complete vision loss if untreated. The risk of blindness can be reduced, however, if the elevated intraocular pressure is detected early and is appropriately managed. Similarly, diabetes is a serious condition which can be more effectively treated with early-stage detection of elevated blood glucose concentration and appropriate management. Appropriate management of either of these conditions can be improved using enhanced monitoring.

Accordingly, diagnostic physiological sensors have been developed for implantation within the human body in order to monitor physiological characteristics such as intraocular pressure and glucose concentration. Such implantable sensors may be used to effectively diagnose and treat certain physiological conditions.

SUMMARY

The present disclosure provides for new physiological sensors for implantation into the ocular environment and related measurement of ocular characteristics. The new sensors, and methods of sensing, disclosed herein advantageously provide for continuous monitoring of physiological phenomena, such as intraocular pressure and glucose concentration. The sensors disclosed herein may wirelessly transmit measured data to an external device for additional processing and analysis; similarly, the sensors disclosed herein may wirelessly charge, via an external device, for improved usability and overall lifespan. Sensors may further provide for flow via internal flow pathways, thus reducing intraocular pressure within the anterior chamber.

In light of the disclosure herein, and without limiting the scope of the invention in any way, in a first aspect of the present disclosure, which may be combined with any other aspect listed herein unless specified otherwise, an intraocular implant includes a physiological sensor, a housing, and at least one protruding anchor. The housing includes a faceplate and a cover. The physiological sensor is integrated with the faceplate. The at least one protruding anchor is configured to penetrate a trabecular meshwork. The at least one protruding anchor includes an internal flow pathway.

In a second aspect of the present disclosure, which may be combined with any other aspect listed herein unless specified otherwise, the physiological sensor comprises an intraocular pressure sensor.

In a third aspect of the present disclosure, which may be combined with any other aspect listed herein unless specified otherwise, the intraocular pressure sensor comprises a capacitive pressure sensor.

In a fourth aspect of the present disclosure, which may be combined with any other aspect listed herein unless specified otherwise, the capacitive pressure sensor comprises a flexible diaphragm electrode spaced apart from a counter electrode.

In a fifth aspect of the present disclosure, which may be combined with any other aspect listed herein unless specified otherwise, the faceplate comprises a first substrate bonded to a second substrate. The flexible diaphragm electrode comprises at least a portion of the first substrate and the counter electrode comprises at least a portion of the second substrate In a sixth aspect of the present disclosure, which may be combined with any other aspect listed herein unless specified otherwise, the implant further includes a first conductive via connected to the flexible diaphragm electrode and extending through the faceplate, a second conductive via connected to the counter electrode, and an electrical interconnect circuit connected to the first conductive via and the second conductive via.

In a seventh aspect of the present disclosure, which may be combined with any other aspect listed herein unless specified otherwise, the implant further includes a coil embedded in an interior surface of the faceplate.

In an eighth aspect of the present disclosure, which may be combined with any other aspect listed herein unless specified otherwise, the coil comprises a conductor provided in a channel formed in the interior surface of the faceplate, the channel being laid out to form a plurality of loops.

In a ninth aspect of the present disclosure, which may be combined with any other aspect listed herein unless specified otherwise, the implant further includes a stress-relief cutout formed in the faceplate around the physiological sensor.

In a tenth aspect of the present disclosure, which may be combined with any other aspect listed herein unless specified otherwise, the stress-relief cutout comprises a channel that extends partially through the faceplate.

In a eleventh aspect of the present disclosure, which may be combined with any other aspect listed herein unless specified otherwise, the faceplate and the physiological sensor are both formed from silicon.

In a twelfth aspect of the present disclosure, which may be combined with any other aspect listed herein unless specified otherwise, the implant further includes a humidity sensor provided inside the housing.

In a thirteenth aspect of the present disclosure, which may be combined with any other aspect listed herein unless specified otherwise, the humidity sensor comprises a capacitor with a plurality of electrodes and a moisture-sensitive dielectric material.

In a fourteenth aspect of the present disclosure, which may be combined with any other aspect listed herein unless specified otherwise, the moisture-sensitive dielectric material comprises a getter material.

In a fifteenth aspect of the present disclosure, which may be combined with any other aspect listed herein unless specified otherwise, the implant further includes a capacitance-to-digital converter to read the capacitance of the humidity sensor.

In a sixteenth aspect of the present disclosure, which may be combined with any other aspect listed herein unless specified otherwise, the physiological sensor comprises a capacitive sensor, and a capacitance-to-digital converter is connected to the physiological sensor to read the capacitance of the physiological sensor.

In a seventeenth aspect of the present disclosure, which may be combined with any other aspect listed herein unless specified otherwise, the physiological sensor comprises a glucose sensor.

In a eighteenth aspect of the present disclosure, which may be combined with any other aspect listed herein unless specified otherwise, the housing comprises a convex curved surface with a first radius of curvature in a first direction and a second radius of curvature in a second direction that is orthogonal to the first direction.

In a nineteenth aspect of the present disclosure, which may be combined with any other aspect listed herein unless specified otherwise, the first radius of curvature corresponds to a radius of curvature of an iridocorneal angle of a normal human eye in a plane orthogonal to an optical axis of the eye, and the second radius of curvature corresponds to the radius of curvature of the iridocorneal angle in a plane that includes the optical axis of the eye.

In a twentieth aspect of the present disclosure, which may be combined with any other aspect listed herein unless specified otherwise, an exterior of the housing is covered in a thin-film atomic layer deposition (ALD) coating.

In a twenty-first aspect of the present disclosure, which may be combined with any other aspect listed herein unless specified otherwise, the thin-film ALD coating covers a surface of the physiological sensor.

In a twenty-second aspect of the present disclosure, which may be combined with any other aspect listed herein unless specified otherwise, the thin-film ALD coating further covers a hermetic seal.

In a twenty-third aspect of the present disclosure, which may be combined with any other aspect listed herein unless specified otherwise, the thin-film ALD coating comprises a multi-layer stack of at least two different materials.

In a twenty-fourth aspect of the present disclosure, which may be combined with any other aspect listed herein unless specified otherwise, the physiological sensor is located in a depression formed in an exterior surface of the faceplate.

In a twenty-fifth aspect of the present disclosure, which may be combined with any other aspect listed herein unless specified otherwise, the housing includes one or more protrusions or grooves to facilitate the flow of aqueous humor around the housing.

In a twenty-sixth aspect of the present disclosure, which may be combined with any other aspect listed herein unless specified otherwise, the housing comprises at least one anchoring tab that holds the at least one protruding anchor.

In a twenty-seventh aspect of the present disclosure, which may be combined with any other aspect listed herein unless specified otherwise, the anchoring tab comprises a through-hole, and the at least one protruding anchor includes a penetrating head at a first end and an elongate body, the elongate body extending through the through-hole of the anchoring tab and having a diameter smaller than the diameter of the through-hole, the penetrating head having a diameter greater than the diameter of the through-hole, wherein a second end of the protruding anchor is deformable.

In a twenty-eighth aspect of the present disclosure, which may be combined with any other aspect listed herein unless specified otherwise, the implant further includes a controller configured to take a measurement of a physiological characteristic using the physiological sensor.

In a twenty-ninth aspect of the present disclosure, which may be combined with any other aspect listed herein unless specified otherwise, the implant further includes a controllable switching device connected between a battery and one or more other electrical components, the controllable switching device being configured to fail open.

In a thirtieth aspect of the present disclosure, which may be combined with any other aspect listed herein unless specified otherwise, the implant further includes a transceiver configured to wirelessly transmit measurement data to an external device.

In a thirty-first aspect of the present disclosure, which may be combined with any other aspect listed herein unless specified otherwise, the implant further includes a hermetic seal between the faceplate and the cover, the hermetic seal comprising a eutectic solder.

In a thirty-second aspect of the present disclosure, which may be combined with any other aspect listed herein unless specified otherwise, a method of monitoring intraocular pressure includes obtaining an intraocular pressure measurement with an intraocular implant, where the intraocular implant includes a physiological sensor, such that intraocular pressure is measured with the physiological sensor. The method includes storing the intraocular pressure measurement in a memory of the intraocular implant. The method includes transmitting the intraocular pressure measurement to an external device via a coil embedded in an interior surface of the intraocular implant. The external device wirelessly receives the intraocular pressure measurement via RF-transmission from the intraocular implant.

In a thirty-third aspect of the present disclosure, which may be combined with any other aspect listed herein unless specified otherwise, the method further includes powering a capacitor disposed within the intraocular implant, where the powering includes wirelessly transmitting power from the external charging device to the coil embedded in the interior surface of the intraocular implant.

Additional features and advantages of the disclosed devices, systems, and methods are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not necessarily have to have all of the advantages listed herein. Moreover, it should be noted that the language used in the specification has been selected for readability and instructional purposes, and not to limit the scope of the inventive subject matter.

BRIEF DESCRIPTION OF THE DRAWINGS

Various embodiments and features of devices, systems, and methods disclosed herein will be described with reference to the following drawings. The drawings, associated descriptions, and specific implementations are provided to illustrate embodiments of the invention and not to limit the scope of the disclosure.

FIGS. 4A-4C illustrate a top view, a top perspective view, and a bottom perspective view, respectively, of another example embodiment of the housing for an intraocular physiological sensor implant.

FIGS. 5A-5C illustrate perspective, front, and cross-sectional side views of example embodiments of anchors that include clocking features and fluid flow passageways.

FIG. 13B illustrates an example method for correlating an atmospheric pressure measurement from an external device with an absolute IOP measurement from a sensor implant for purposes of determining a gauge IOP value.

DETAILED DESCRIPTION

There is a need to effectively monitor intraocular pressure within a patient's eye in order to detect or monitor the progression of glaucoma. Intraocular pressure can be measured non-invasively using, for example, a tonometer. While tonometers have the advantage of being non-invasive, they have the disadvantages of generally being expensive, nonportable, specialized equipment that requires skilled operation. Accordingly, as a practical matter, it is difficult to use a tonometer to effectively monitor intraocular pressure in a patient's eye with a time resolution greater than one measurement every few days or weeks. However, since intraocular pressure can vary significantly over relatively short periods of time, such relatively sparse intraocular pressure measurements may not provide a complete or accurate picture of the patient's risk for, or progression of, glaucoma. It would therefore be advantageous to be able to measure intraocular pressure more often or even continuously.

Figure 1A:
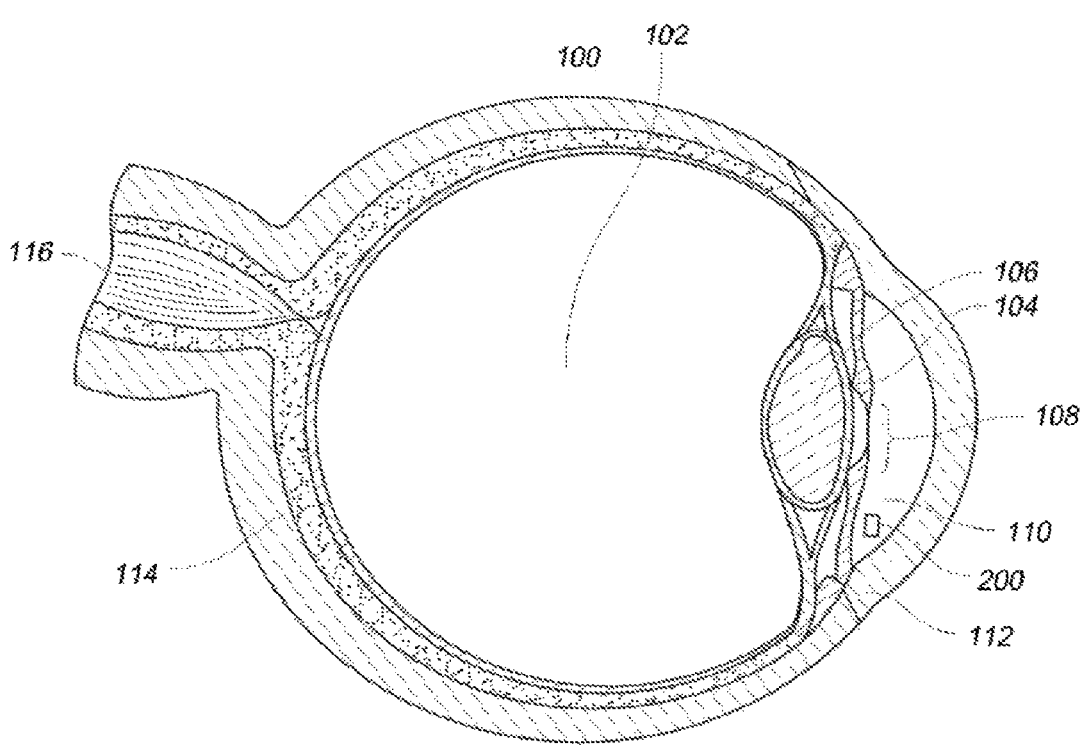
FIG. 1A illustrates a schematic illustration of an intraocular physiological sensor implant located in a human eye.

FIG. 1A is a schematic illustration of an intraocular physiological sensor implant 200 located in a human eye 100. For reference, various anatomical features of the eye 100 are labeled in FIG. 1A. For example, FIG. 1A shows the vitreous humor 102, the iris 104, the lens 106, the pupil 108, the anterior chamber 110 (including the aqueous humor which fills the anterior chamber), the cornea 112, the retina 114, and the optic nerve 116. FIG. 1A also illustrates an intraocular physiological sensor implant 200 (not necessarily drawn to scale or shape) that is located within the anterior chamber of the eye. The sensor implant 200 is capable of continuously measuring one or more physiological characteristics, such as intraocular pressure within the eye.

Figure 1B:
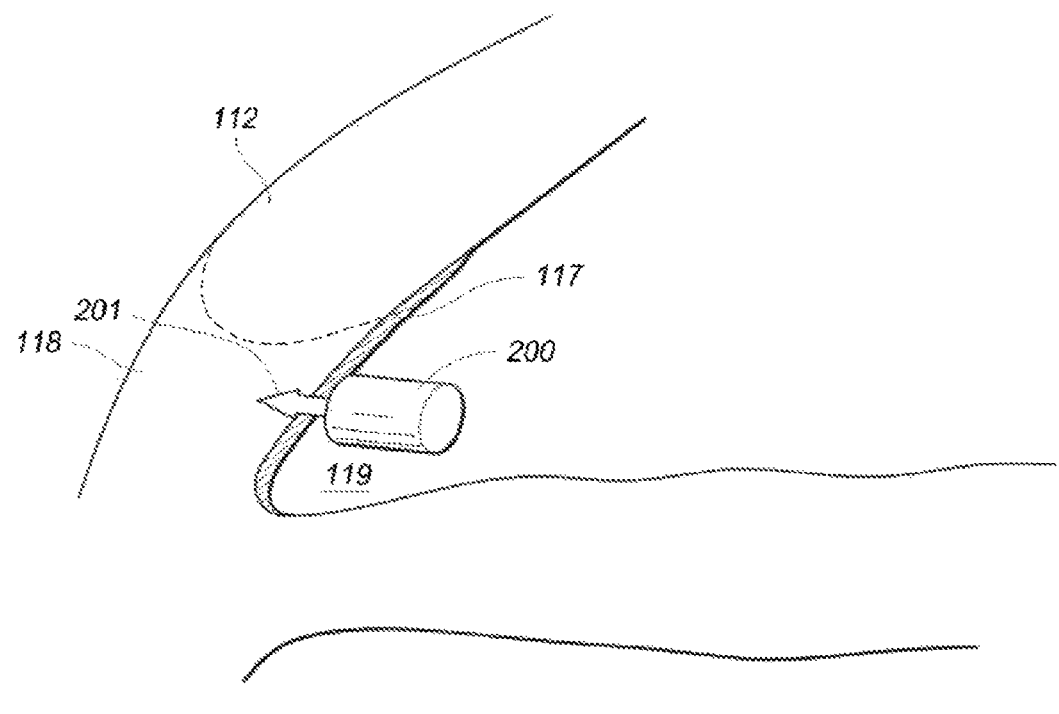
FIG. 1B illustrates a schematic illustration of an intraocular physiological sensor implant fixed by an anchor embedded into scleral tissue, through meshwork tissue, in the iridocorneal angle.

The sensor implant 200 can be positioned at several different locations within the eye 100. For example, the sensor implant 200 can be fixedly attached or anchored to any suitable anatomical feature of the eye, including but not limited to the sclera or iris, depending upon the particular application. The sensor implant 200 can also be fixedly attached or anchored to or within a physiological aqueous humor outflow pathway. The physiological aqueous humor outflow pathways include the "conventional" pathway comprising the trabecular meshwork and Schlemm's canal, and the "uveoscleral" pathway comprising the ciliary body, the sclera, and the supraciliary/suprachoroidal space. FIG. 1B illustrates the location of the sensor implant 200 fixed by an anchor 201 that is inserted through trabecular meshwork tissue 117 and is embedded into scleral tissue 118 in the iridocorneal angle 119. Alternatively, the sensor implant 200 could be attached to some other anatomical feature such as the sclera, the scleral spur, the vitreous cavity, or even another intraocular implant, such as an intraocular lens.

While some embodiments of the sensor implant 200 measure intraocular pressure, some embodiments may also, or alternatively, measure glucose concentration in the aqueous humor. Specifically, there is a need to measure glucose concentration within the human body as a means to treat or prevent complications from diabetes. Glucose is typically measured from blood or urine sampling. Some implantable glucose sensors have been developed that measure glucose from interstitial fluids; however, the body may have a negative immunological response to such implants, which may degrade the performance of the sensor over time. The eye 100, especially the anterior chamber 110 of the eye, is an immunologically-privileged site within the body. Thus, an intraocular sensor implant for measuring glucose within the eye can have advantages over other implantable sensors that are made to measure glucose in non-immunologically privileged parts of the body. In addition, although the glucose concentration within the aqueous humor may not be identical to blood glucose concentration, the two may be correlated such that a measurement of glucose concentration in the aqueous humor can be predictive of blood glucose concentration.

In an embodiment, the sensor 200 runs a current and measures an initial rate of decay of reactive buildup on a glucose sensor. From this measured initial rate of decay, the sensor 200 implements an algorithm to approximate glucose levels at the time where all buildup has decayed. In this way, sensor 200 advantageously avoids unnecessary power consumption associated with burning off the entire reactive buildup.

It may be advantageous to measure both intraocular pressure and glucose concentration in the aqueous humor because the glucose concentration measurement can be used to diagnose and/or treat diabetes. Meanwhile, diabetes patients are also at higher risk of developing glaucoma. Thus, there may be a significant overlap of the patient population for whom intraocular pressure and glucose concentration measurements would be valuable.

Furthermore, in various embodiments, it should be appreciated that the sensors disclosed herein, such as sensor implant 200, could be implanted and positioned in alternate locations within the human body besides the eye. For example, sensor implant 200 could measure pressure of other organs, such as the brain or heart, or other locations, such as the thoracic cavity, exterior limbs, and the like. Likewise, sensor implant 200 could measure other values, such as glucose concentration, at these alternate locations. Alternate location implantation can be performed with limited, if any, design changes to the sensor implant 200 disclosed herein. Thus, in certain embodiments, sensor implant 200 is location agnostic.

Figures 2A, 2B:
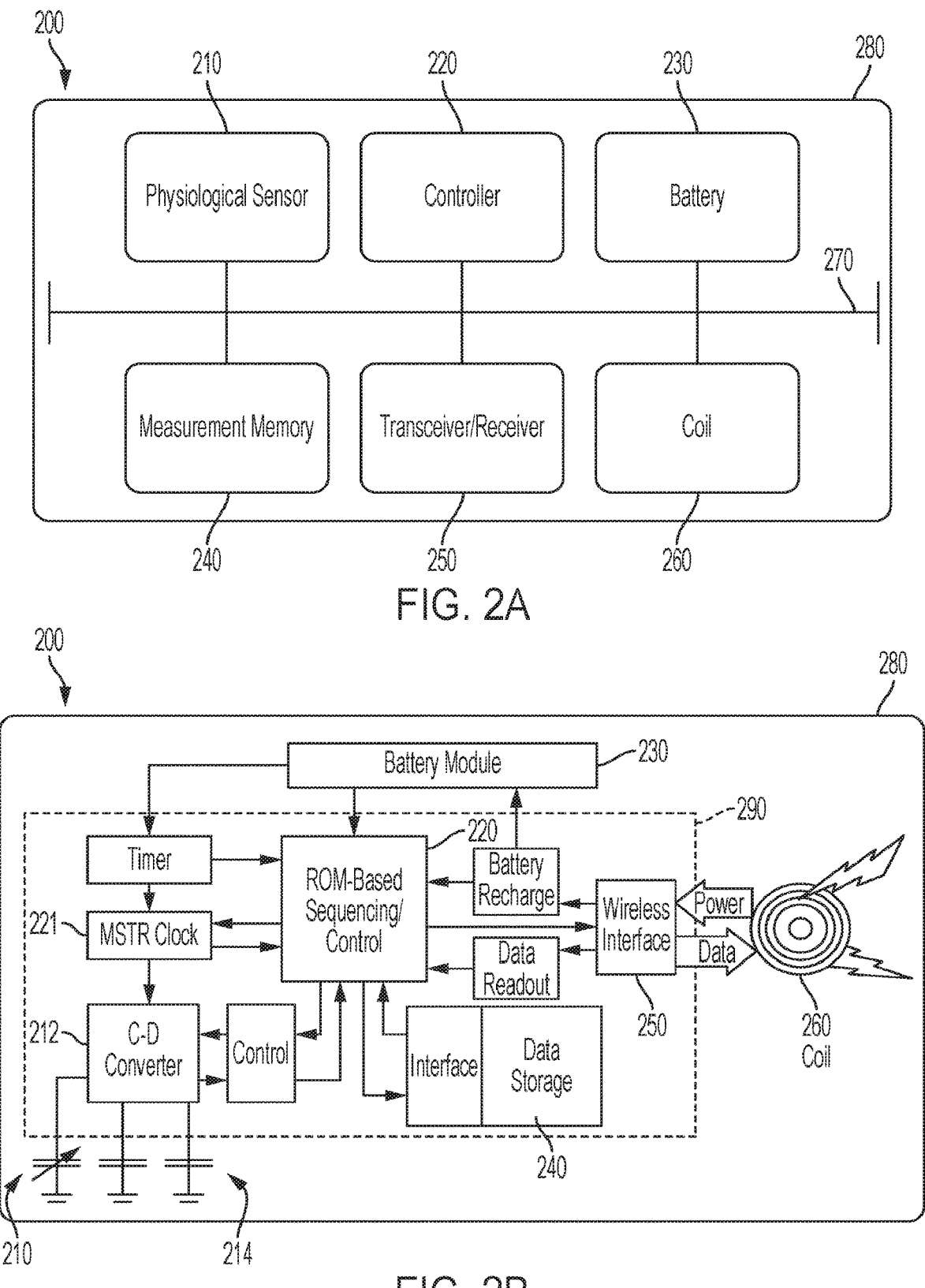
FIG. 2A illustrates a block diagram of an example embodiment of an intraocular physiological sensor implant.
FIG. 2B illustrates a block diagram of another example embodiment of an intraocular physiological sensor implant.

FIG. 2A is a block diagram of an example embodiment of the intraocular physiological sensor implant 200. The illustrated embodiment of the sensor implant 200 includes a physiological sensor 210, a controller 220, a battery 230, a measurement memory 240, a transceiver/receiver 250, an inductive coil 260, and an electrical interconnect circuit 270 for communicating power and/or data between the various components of the implant 200. One or more of the illustrated components can be implemented as one or more integrated circuits. Some embodiments of the sensor implant 200 may omit one or more of the components illustrated in FIG. 2A, or may include additional or alternative components besides those which are specifically illustrated. Each of the components of the sensor implant 200 may be wholly or partially housed in a biocompatible housing 280, as described in greater detail herein.

The physiological sensor 210 is a component that performs measurements of one or more physiological characteristics of interest. The physiological sensor 210 can output a signal, such as an electrical signal, that is quantitatively representative of the physiological characteristic under measurement. In some embodiments, the physiological sensor 210 can be designed to measure intraocular pressure, intraocular glucose concentration, and/or any other physiological characteristic of interest that can be detected within the eye. The sensor implant 200 may also include multiple instances of the physiological sensor 210. Each instance of the sensor 210 may be used to measure a different physiological characteristic. For example, the sensor implant 200 can include two instances of a physiological sensor 210 for measuring intraocular pressure and glucose concentration.

Measurements taken using the physiological sensor 210 can be stored in the measurement memory 240. The measurement memory 240 can be, for example, a solid-state electronic memory device. The measurement memory 240 can be used to internally log measurements from the physiological sensor 210 until they can be retrieved by an external device that is communicatively coupled to the sensor implant 200 via the transceiver/receiver 250.

The transceiver/receiver 250, such as a bi-directional radio, can be communicatively coupled to the coil 260 and can be used to wirelessly receive data, such as commands, from an external device and/or to wirelessly transmit data including physiological measurements from the sensor implant 200 to the external device. The transceiver/receiver 250 may be controlled, such as via controller 220, to transmit measurements on demand, according to a set schedule, and/or at regular or irregular intervals, such as daily. In some embodiments, the external device may be a data logger that is worn by the patient for storing the measurements until they can be downloaded by a clinician. In other embodiments, the external device may be a handheld reader device used by a clinician to periodically download measurement data that is stored internally by the measurement memory 240. The reader device can then transmit the downloaded measurements to a computer, via the Internet or some other communication network, for processing and/or for analysis by a clinician. The reader device can also provide the downloaded measurements to the patient via a user interface.

The controller 220 can be used, for example, to perform control operations for the other components of the sensor implant 200. In some embodiments, the controller 220 may provide commands to cause measurements to be taken using the physiological sensor 210. In some embodiments, the controller 220 causes measurements to be taken at regular intervals. For example, measurements may be taken on demand, such as based on input from an external device, according to a set schedule, and/or at regular or irregular intervals, such as at least hourly, at least every 15 minutes, at least every minute, or the like, depending upon the particular application. In some embodiments, the controller 220 causes measurements to be taken at time intervals which are shorter than the typical interval over which appreciable changes in the physiological characteristic can occur. In this way, trend data regarding the physiological characteristic of interest can be collected so as to provide a more useful or complete picture of how the physiological characteristic changes as a function of time. In some embodiments, the controller 220 causes measurements to be take even faster, such as at a rate of 20 Hz or faster such that high-frequency IOP fluctuations, such as those due to the cardiac pulse, can be identified and recorded. Alternatively, in some embodiments, measurements could be taken less frequently throughout the day in order to conserve energy including battery life.

The controller 220 may also control the writing and reading of measurement data to a measurement memory 240. The controller 220 may also control transmission and reception of data using a transceiver/receiver 250. In addition, the controller 220 may control power settings of the battery 230 and/or power supply electronics.

The controller 220 may also perform other functions. For example, in some embodiments, the controller 220 can perform data processing tasks on the measurements collected using the physiological sensor 210. In other embodiments, however, any required data processing tasks can be performed by an external device after downloading the measurements in order to avoid the power demands of onboard processing. In addition, the controller 220 may monitor the collected measurements and output alarm signals, such as to an external device via the transceiver/receiver 250, if the physiological characteristic that is being monitored reaches some threshold value or if immediate notification is otherwise considered necessary. For example, an alarm signal can be triggered if the sensor implant 200 detects a potentially dangerous low blood sugar level. The controller 220 can also perform measurement data compression to allow for more measurements to be stored in the measurement memory 240. The controller 220 can also perform encryption on the data or information being sent by or received by the transceiver/receiver 250. The controller 220 can also issue commands to other components of the sensor implant 200, such as the transceiver/receiver 250, the measurement memory 240, the physiological sensor 210, and the like, to shut down or enter a power-saving state when not in use.

In the illustrated embodiment, the sensor implant 200 uses a battery 230 to wholly or partially satisfy the power demands of any or all of the other components of the sensor implant 200. The battery 230 can be rechargeable. For example, the sensor implant 200 can use the coil 260 to receive power from an external device via inductive or radio frequency (RF) coupling. This power can be used to recharge the battery 230. In some embodiments, the battery 230 can be a thin-film lithium-ion or lithium-metal battery. The sensor implant 200 can also include power supply electronics, such as a voltage regulator, a voltage converter, and/or any other electrical component that may be desirable for conditioning the electrical power output by the battery 230 so that it can be satisfactorily used by other electrical components within the sensor implant 200.

In some embodiments, the battery 230 can be connected to the other components of the sensor implant 200 by a switch or other switching component that can be controlled by the controller 220. When the switch is closed, the sensor implant 200 consumes power from the battery 230. When the switch is open, the sensor implant 200 is in the on-demand mode in which it can consume power that is wirelessly-transferred from an external device. The switch can be advantageous to ensure that battery power is only consumed when instructed by the controller 220. The switch can be designed such that it fails open when the battery 230 becomes discharged and power to the controller 220 is lost. This ensures that the sensor implant 200 can be operated in the on-demand mode if the battery 230 is discharged or becomes inoperable.

Figure 3A:
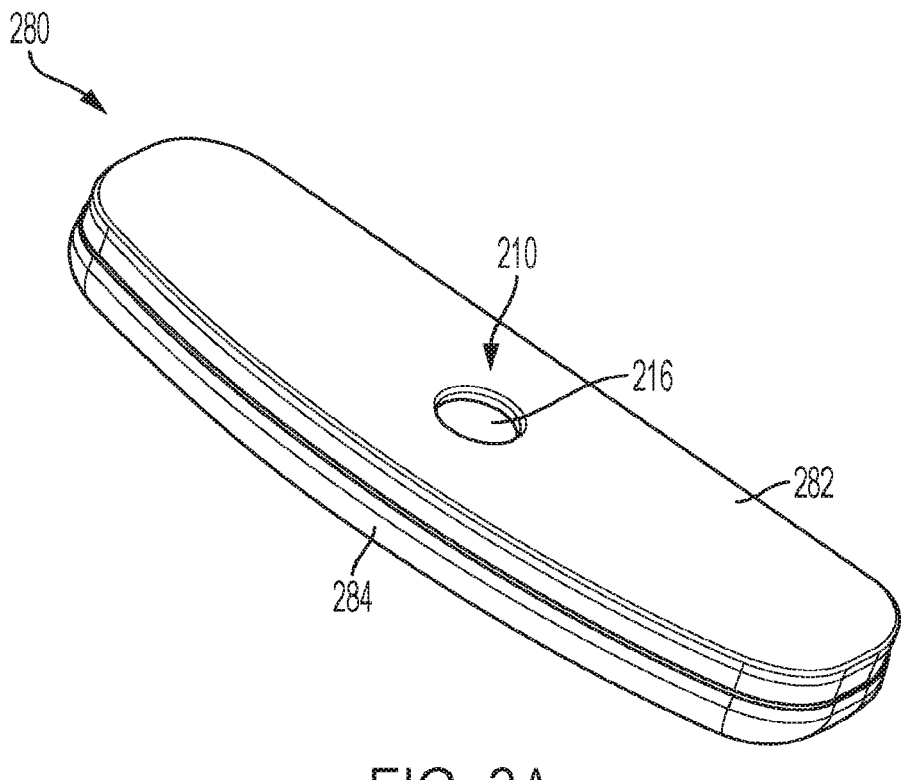
FIG. 3A illustrates a bottom perspective view of an example embodiment of the housing for an intraocular physiological sensor implant.
Figure 3B:
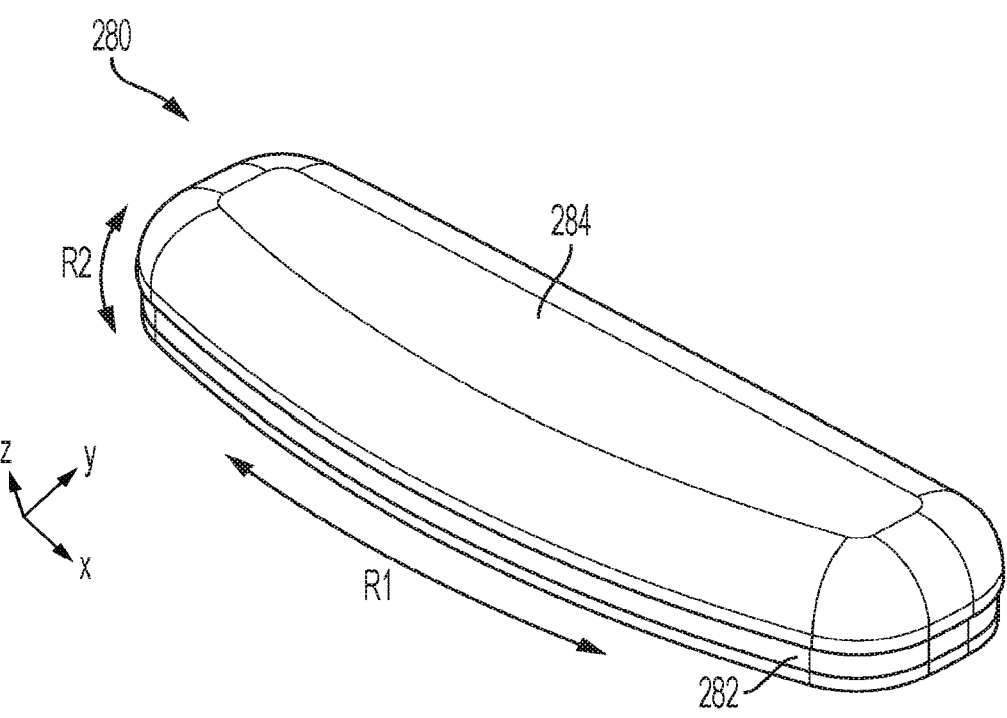
FIG. 3B illustrates a top perspective view of the example embodiment of the housing for the intraocular physiological sensor implant which is shown in FIG. 3A.

FIG. 2B is a block diagram of another example embodiment of the intraocular physiological sensor implant 200. In this embodiment, the sensor implant 200 is an intraocular pressure sensor. The illustrated embodiment of the sensor implant 200 includes a pressure sensor 210, a controller 220, a battery 230, a measurement memory 240, a transceiver/receiver 250, a coil 260, and an interconnect 270 for communicating power and/or data between the various components of the implant 200. Each of the components of the sensor implant 200 may be wholly or partially housed in a biocompatible housing 280, which is illustrated in FIGS. 3A and 3B.

Various ones of the illustrated components can be implemented together as an application-specific integrated circuit (ASIC) 290 (illustrated as the dashed box in FIG. 2B) on a chip, though some components can also be provided as discrete components with, for example, electrical connections to the integrated circuit 290.

There are several different types of tonometric devices for measuring intraocular pressure, any of which can be used as the pressure sensor 210. In some embodiments, the pressure sensor 210 includes a capacitor whose capacitance varies in response to the pressure of the medium where the sensor implant 200 is located. The capacitor can include a microelectromechanical system (MEMS). For example, the pressure sensor 210 can include a fixed capacitor plate electrode in proximity to a flexible diaphragm or membrane electrode.

The distance between the flexible diaphragm electrode and the fixed plate electrode varies in response to the pressure applied by the aqueous humor when the sensor implant 200 is implanted within the eye 100. This is detected as a change in capacitance of the capacitor. In other embodiments, pressure sensor 210 additionally or alternatively uses other means for measuring pressure, such as resistive strain gauges, piezoresistive strain gauges, piezoelectric strain gauges, optical measurement, or any other related means for measuring pressure.

In some embodiments, the pressure sensor 210, when combined with the rest of the system of the sensor implant 200, is capable of measuring intraocular pressure from about 0 mmHg to about 50 mmHg of gauge pressure within the eye 100 with about ±0.5 mmHg resolution. In some embodiments, the cavity underneath the flexible diaphragm is sealed under vacuum, and the pressure sensor 210 responds over the range of approximately 500 to 1000 mmHg absolute pressure with about an essentially infinite resolution as the output is a variable analogue capacitance signal. The atmospheric pressure can be measured independently outside the body and subtracted from the absolute pressure measured by the pressure sensor 210 to yield the intraocular pressure. In some embodiments, the capacitance varies in an approximately linear fashion relative to the intraocular pressure. In some embodiments, the capacitance may increase approximately linearly from approximately 1 picofarads (pF) to approximately 4 pF over the range of absolute pressure from 500 to 900 mmHg. In other embodiments the absolute pressure range is smaller or larger or the sensitivity of the sensor is more or less. In some embodiments, the capacitance varies in a non-linear fashion relative to intraocular pressure.

The pressure sensor 210 can be electrically connected to a capacitance-to-digital converter 212 that outputs a value which is indicative of the capacitance of the pressure sensor 210, and, therefore, the detected pressure. This value can be provided to the controller 220. In some embodiments, the intraocular pressure sensor 210 also includes one or more reference capacitors 214.

Namely, pressure sensor 210 may include one or more reference capacitors 214, such as a buried cavity reference MEMS capacitor disposed adjacent to pressure sensor 210. The reference capacitors 214 can also be connected to the capacitance-to-digital converter 212, and can be used to provide a reference value for calibration and/or temperature compensation. The structure of the reference capacitor 214 is similar to that described above with respect to pressure sensor 210, except that a sensing port is not present. Thus, the faceplate 282 above the reference capacitor 214 prevents the reference capacitor 214 from appreciably responding to pressure changes within the anterior chamber of the eye. In this embodiment, a through-silicon via is used to connect to the reference capacitor 214. The capacitive signal generated by the reference capacitor 214 can be used to filter out effects unrelated to changes in pressure, such as intrinsic stresses, mechanical stresses, temperature changes, and the like, thereby improving the accuracy of the system as a whole. Signal from the reference capacitor 214 can be used directly, such as via a direct analogue subtraction of its capacitance from the capacitance of pressure sensor 210 within the ASIC's operation or a digital subtraction of the same, or indirectly by reading its value substantially concurrently with reading the reference capacitor 214 and the capacitance of pressure sensor 210 and using both measurements during downstream data processing/calibration. In the preferred embodiment, the reference capacitor 214 has the same dimensions as the pressure sensor 210, but can also be of different size and shape and still provide similar utility.

In an embodiment, a temperature sensor is built into the interconnect circuit 270, and also can be used for temperature compensation and/or for calibration purposes. Another benefit of integrating the temperature sensor with the interconnect circuit 270 in one embodiment is to compensate for thermal drift as the interconnect circuit, and various components thereon, are subjected to heating and cooling that could result in unpredictable thermal expansion impacting the integrity and reliability of sensor measurements.

Pressure measurements from the pressure sensor 210 can be stored in the measurement memory 240. In some embodiments, the measurement memory 240 is a solid-state memory that is provided as part of the integrated circuit 290. For example, the measurement memory 240 can be a 8 kB static random-access memory (SRAM), though other types of memory and/or capacities can also be used. In some embodiments, the controller 220 performs data compression on the pressure measurements before storing them in the measurement memory 240. By performing data compression, the measurement memory 240 can hold more measurements. This can allow for more frequent measurements and/or less frequent data downloading events. In some embodiments it may be advantageous to use a relatively simple compression technique so as to preserve computational resources. One example data compression algorithm could be to store the difference between sequential measurements rather than the measurements themselves. This technique could allow for fewer bits per measurement to be used by the measurement memory 240.

The controller 220 can perform any of the functions described elsewhere herein. For example, in some embodiments, the controller 220 can be programmed to cause measurements to be taken using the pressure sensor 210 at predetermined times, on demand, and/or regular intervals determined by, for example, the MSTR clock 221. Each recorded/reported measurement can, however, be calculated from multiple measurements taken using the pressure sensor 210. For example, the controller 220 can be programmed to obtain multiple measurements, such as three measurements, at relatively short intervals, such as 30 seconds, or even shorter intervals, such as 0.5 seconds. These can then be averaged and recorded/reported as a single measurement at the measurement memory 240. This process can then be repeated at longer intervals, such as hourly.

The sensor implant 200 illustrated in FIG. 2B includes a battery 230 to power components such as the controller 220, the pressure sensor 210, the transceiver/receiver 250, and the like. The battery can have a power rating of approximately 5 μAh, or greater. Such a power rating is estimated to provide sufficient power for at least approximately 7 days between recharges. In some embodiments, the sleep power consumption of the sensor implant 200 is on the order of picowatts or nanowatts while the active power consumption is on the order of nanowatts or microwatts. It should be understood, however, that the size and power rating of the battery 230 could be different than the figures listed above, as could the power consumption of the sensor implant 200.

In some embodiments, the battery 230 is rechargeable by an external device, as discussed elsewhere herein. For example, the battery 230 can be recharged wirelessly via inductive coupling or RF energy from an external device. In other embodiments, the battery 230 can be charged by solar power or by an infrared laser (in which case, the sensor implant 200 can include an appropriate photovoltaic cell to convert the solar or infrared laser light to electrical power) or by a fuel cell powered by glucose present in the aqueous humor.

The transceiver/receiver 250 and the coil 260 can be used to wirelessly transmit pressure measurements stored in the measurement memory 240 to an external reader device. The external reader device can be integrated into a pair of eyeglasses that are worn by the patient to download pressure measurements from the sensor implant 200. The coil 260 can also serve a dual purpose of receiving power wirelessly via inductive coupling in order to charge the battery 230, such as while the stored measurements are being downloaded. A wireless charging device can be integrated in the same eyeglasses that include the external reader device for downloading data from the sensor implant 200. The coil 260 can transmit measurement data and receive power for recharging the battery 230 either simultaneously, or one at a time (in either order). In some embodiments, the coil 260 includes multiple conductive loops which are oriented so that their axis is generally aligned with the optical axis of the eye. This orientation can allow for a relatively larger amount of electromagnetic flux to pass through the conductive loops after being transmitted from an external device positioned in front of the eye, such as from an external device integrated into the frame of a pair of eyeglasses.

FIG. 3A is a bottom perspective view of an example embodiment of the housing 280 for the intraocular physiological sensor implant 200. In the illustrated embodiment, the housing 280 includes two sections which fit together to jointly form the housing. The housing 280 can include, for example, a bottom faceplate 282 and a top cover 284. In some embodiments, the faceplate 282 is generally flat, while the top cover 284 is domed. The faceplate 282 and the cover 284 can both be made of impermeable, biocompatible materials, though they need not necessarily be made of the same material. The selected materials for the housing 280 can be at least partially transmissive, and preferably substantially transparent, to radio frequency (RF) electromagnetic radiation, such as ceramic, glass or silica. A hermetic seal can be provided between the faceplate 282 and the cover 284 to prevent aqueous humor or moisture from infiltrating the housing 280 and/or to prevent atoms or molecules of metals or other materials inside the housing 280 from being introduced into the patient's eye.

In the illustrated embodiment, the physiological sensor 210 is integrated into the faceplate 282. In this example, the physiological sensor 210 is a capacitive intraocular pressure sensor which includes a flexible diaphragm 216, as already discussed above. In some embodiments, the flexible diaphragm 216 and the faceplate 282 can be made partially or wholly of the same material, such as silicon. The faceplate 282 and the flexible diaphragm 216 can be formed as a unitary body, such as from one or more contiguous substrates of the chosen material, like silicon, as shown and described further herein. This type of design may be advantageous because it can eliminate a hermetic seal between the physiological sensor 210 and the faceplate 282, which might otherwise be needed if the physiological sensor and faceplate were constructed as separate components and subsequently joined together. The lack of a need for such a hermetic seal between the physiological sensor 210 and the faceplate 282 is advantageous because there are then fewer locations where aqueous humor can infiltrate the housing 280 and also because a hermetic seal around, or in the vicinity of, the flexible diaphragm 216 could induce mechanical stresses or strains which might influence the performance of the flexible diaphragm.

FIG. 3B is a top perspective view of the example embodiment of the housing 280 for the intraocular physiological sensor implant 200 which is shown in FIG. 3A. This view shows the top cover 284. Like the faceplate 282, the top cover 284 can be made of a biocompatible material, although the specific material can be different from the one used for the faceplate. In some embodiments, the top cover 284 is ceramic or glass. For example, the top cover 284 can be made of injection-molded zirconia-toughened alumina (ZTA) ceramic, injection-molded yttria-stabilized zirconia (YSZ), sapphire or glass. Other materials and other manufacturing technologies, such as machining or milling, can also be used.

In some embodiments, the sensor implant 200 may be sized and shaped to be placed in the iridocorneal angle of the human eye. The dimensions of the sensor implant 200 may be for example, 2 to 6 mm in length, 0.5 to 2 mm in width, and 0.3 to 1 mm in height. As illustrated, in some embodiments, the top cover 284 and/or the faceplate 282 may have one or more contoured surfaces or chamfers. For example, one side surface of the housing 280 may be contoured with a convex radius of curvature R1 (in the illustrated x-y plane) which corresponds to the normal radius of curvature of the iridocorneal angle of the human eye in a plane generally perpendicular to the optical axis of the eye. The radius of curvature R1 can be, for example, in the range of 5 to 7 mm. The same side surface of the housing 280 may also be contoured with a convex radius of curvature R2 (in the illustrated y-z plane) which corresponds to the normal radius of curvature of the iridocorneal angle of the human eye generally in the plane of the optical axis of the eye. The radius of curvature of R2 can be, for example, in the range of 0.1 to 0.4 mm.

The contoured shape of the illustrated embodiment of the housing 280 allows the intraocular physiological sensor implant 200 to be effectively placed deep into the iridocorneal angle of the patient's eye. This in turn limits the external visibility of the sensor implant 200 outside of the eye. In some embodiments, the sensor implant 200 can be provided with documentation which instructs a surgeon to position the sensor implant in the iridocorneal angle at the superior portion of the patient's eye. This position can take advantage of the fact that the upper eyelid typically extends further than the lower eyelid and is therefore able to more effectively hide the sensor implant 200.

The contoured shape of the housing 280 also provides for additional enclosed volume as compared to a straight-sided housing with similar placement in the iridocorneal angle, which would leave a gap between the housing and the curved surfaces of the iridocorneal angle. This additional enclosed volume inside the housing 280 can be used to fit additional or larger components and/or to shrink other dimensions of the housing. For example, as discussed further herein, the more efficient usage of space which is provided by the contoured housing 280 can allow for a larger coil 260, which can in turn improve communication and/or power transfer between the sensor implant 200 and an external device, or allow for a larger battery 230, which can increase the time between charging.

Since the housing 280 of the sensor implant 200 is designed with at least one contoured surface so as to fit deep within the iridocorneal angle, it may have the potential to limit the outflow of aqueous humor—either through the "conventional" outflow pathway comprising the trabecular meshwork and Schlemm's canal or the "uveoscleral" outflow pathway comprising the ciliary body, the sclera, and the supraciliary/suprachoroidal space—from the portion of the iridocorneal angle where it is located. Given the relatively small portion of the iridocorneal angle which is occupied by the sensor implant 200, any reduction in outflow of aqueous humor is likely to be minor. However, in some embodiments, the housing 280 may include one or more flow-enabling features, such as protruding ribs or recessed grooves/channels. Flow-enabling features such as these can create areas of separation between the housing 280 and the iridocorneal angle, thus allowing aqueous humor to exit the anterior chamber via the physiological outflow pathways even when the housing of the sensor implant 200 is positioned in contact with the surfaces of the iridocorneal angle.

In some embodiments, the flow-enabling features can be made out of or include a porous material, such as fritted glass, porous plastic such as polypropylene, polyethylene, porous bonded polymer fibers such as polyethylene, polyester, or other materials that are preferably hydrophilic and can be formed into an open-cell porous structure. Such porous materials provide a plurality of fluid handling capillary or pseudo-capillary structures that enable fluid transfer through the bulk structure of the material itself. For example, the porous material may be provided on substantially the entire exterior surface of the housing 280, in ribs or strips on the housing, in grooves/channels formed on the outside of the housing, or the like. In an embodiment, these flow-enabling features, such as ribs or grooves in ceramic, can be formed directly onto housing 280, even though the ceramic itself remains a single monolithic component.

FIGS. 4A-4C include a top view, a top perspective view, and a bottom perspective view, respectively, of another example embodiment of the housing 280 for the intraocular physiological sensor implant 200. As shown in these figures, the housing 280 can include one or more anchors 286. The anchors 286 can protrude from, for example, the contoured surface of the housing 280 which is designed to be positioned adjacent to the surfaces of the iridocorneal angle. The anchors 286 are illustrated as protrusions from the top cover 284, but they could alternatively be protrusions from the faceplate 282. The embodiment of the housing 280 shown in FIGS. 4A-4C can otherwise be identical to the embodiment described with respect to FIGS. 3A-3B.

The anchors 286 can include a penetrating tip, which is designed to penetrate ocular tissue, such as the sclera, the trabecular meshwork, and the like, and a barb or other retention feature so as to remain anchored in the tissue after having been inserted. In some embodiments, the anchors 286 can be drug eluting anchors, similar to the one illustrated in FIG. 18 of U.S. Patent Publication 2015/0342875 (see accompanying appendix), filed May 28, 2015, and entitled "IMPLANTS WITH CONTROLLED DRUG DELIVERY FEATURES AND METHODS OF USING SAME," the entire contents of which are hereby incorporated by reference herein. In some embodiments, the anchors 286 can be drainage stents which enhance outflow of aqueous humor from the eye, similar to the one illustrated in FIG. 18 of U.S. Pat. No. 9,554,940 (see accompanying appendix), filed Mar. 14, 2013, and entitled "SYSTEM AND METHOD FOR DELIVERING MULTIPLE OCULAR IMPLANTS," the entire contents of which are hereby incorporated by reference herein. Drainage stent anchors are discussed in greater detail herein with reference to FIGS. 4N-4R.

As shown in FIGS. 4A-4C, the width of the housing 280 along its length can be the greatest in the central portion of the housing. Meanwhile, the housing 280 can taper in width towards the ends of the housing. In some embodiments, the anchors 286 can be positioned toward the ends of the housing 284, such as outside the central third of the housing.

This placement of the anchors 286 can reduce the overall width of the sensor implant 200 as compared to an alternative embodiment with placement of an anchor at the middle section of the housing 284. This reduced overall width of the sensor implant 200 can make the device easier to insert and maneuver within the patient's eye.

Figure 4D:
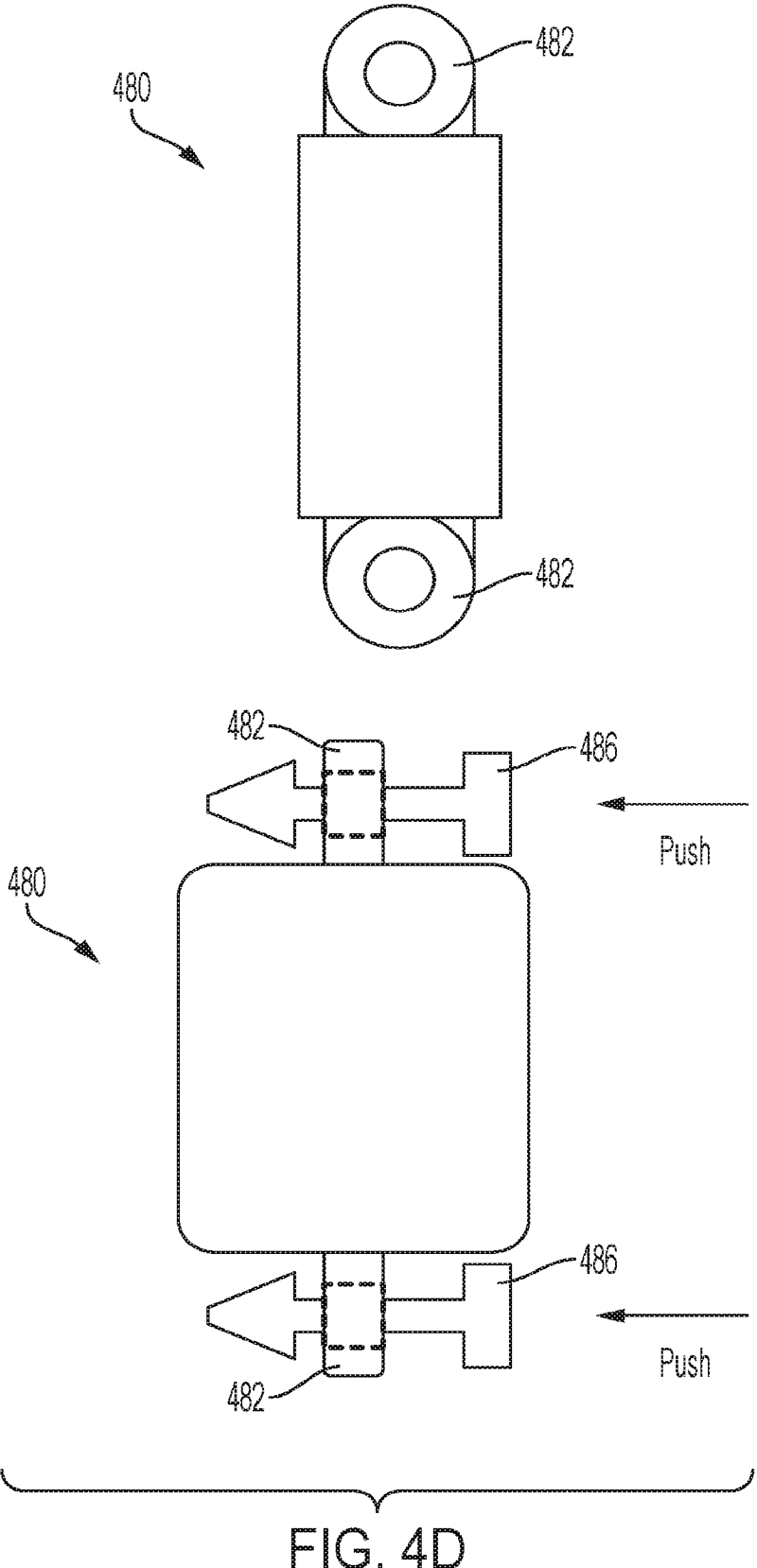
FIG. 4D illustrates side and top views of another example embodiment of a housing for the intraocular physiological sensor implant.

FIG. 4D illustrates another example embodiment of a housing 480 for the intraocular physiological sensor implant 200. In the embodiment illustrated by FIG. 4D, the housing 480 is positioned at the implantation location, and then anchors are pushed through anchoring tabs 482 via a blunt tool, to penetrate tissue and secure the implant in place. Specifically, the top portion of FIG. 4D shows a side view of the housing 480, while the bottom portion of FIG. 4D shows a top view of the housing. In the illustrated embodiment, the housing 480 includes two anchoring tabs 482 which extend from opposite sides of the housing. Although two anchoring tabs 482 are illustrated, other embodiments may include more or fewer anchoring tabs. Each of the anchoring tabs includes a through hole which is configured and dimensioned to hold an anchor 486. Each of the anchors 486 includes a penetrating head with a penetrating tip, an elongate body, and a retention head. The elongate body of each anchor 486 has a diameter which is smaller than the diameter of the through hole in the corresponding anchoring tab 482, while the penetrating head and retention head of the anchor have diameters which are larger than the diameter of the through hole. As a result, each anchor 486 can freely slide within the through hole of the corresponding anchoring tab, but the penetrating head and the retention head of the anchor retain it so that it is captured in the anchoring tab. In some embodiments, the length of the elongate body of each anchor 486 is at least as long as the thickness of the corresponding anchoring tab 482 plus the desired insertion depth of the penetrating tip in ocular tissue.

Once a surgeon has positioned the housing 480 at the desired location within the patient's eye, he or she exerts a longitudinal force on the retention head of each anchor 486 along the axis of its body. This causes the penetrating head of the anchor 486 to extend into ocular tissue so as to hold the housing 480 in place. Similar anchoring tabs 482 and captured anchors 486 can be used in other embodiments of the sensing implant 200. For example, the housing 280 of the sensing implant 200 shown in FIGS. 3A-3B could be modified to include anchoring tabs 482 on opposite ends of the housing.

Figure 4E:
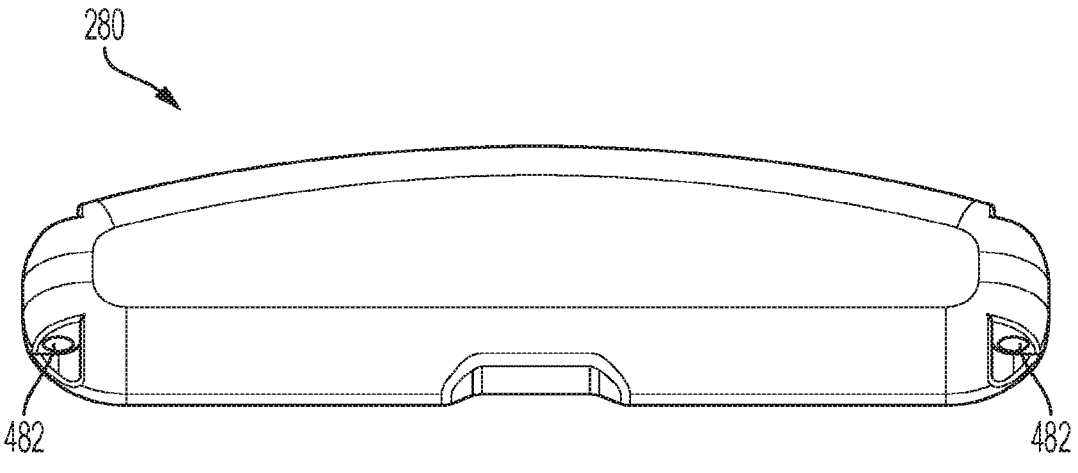
FIGS. 4E-4G illustrate top perspective views of another example embodiment of the housing and related anchor for an intraocular physiological sensor implant.
Figure 4F:
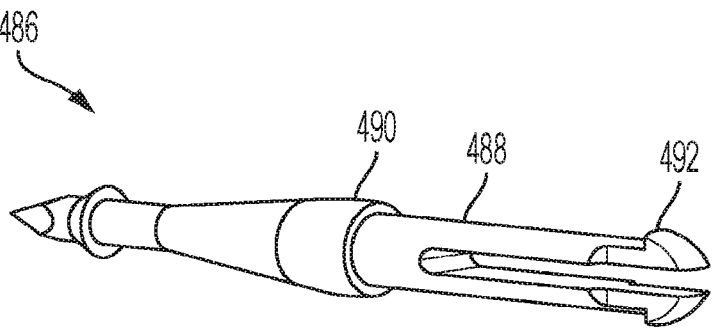
Figure 4G:
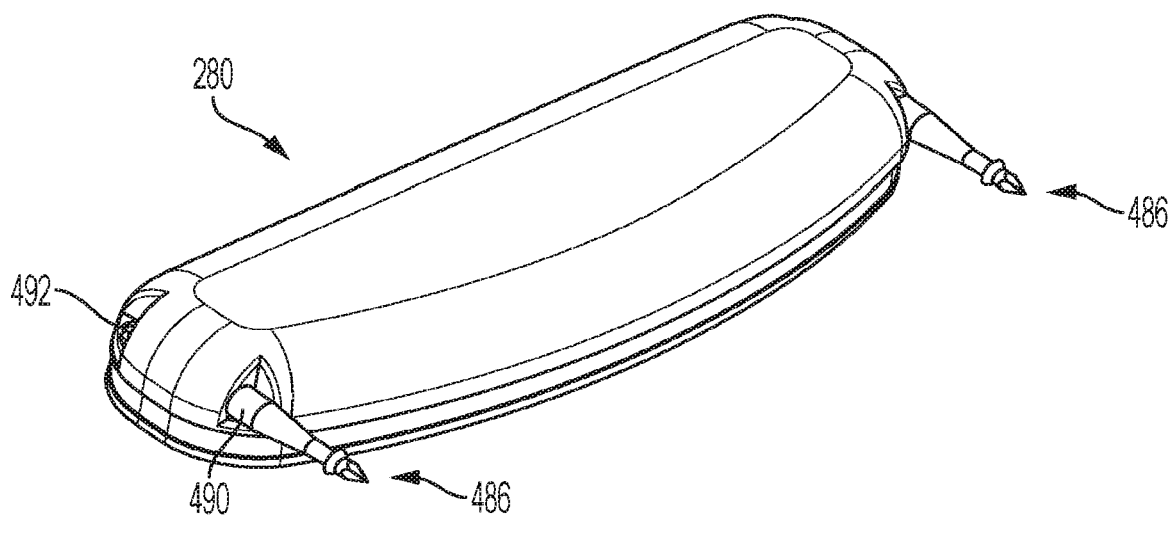

Specifically, for example, FIGS. 4E-4G illustrate housing 280, which further includes several anchoring tabs 482, disposed within housing 280, and configured to receive anchors 486. When compared to FIG. 4D, FIGS. 4E to 4G illustrate embodiments where anchors are rigidly fixed to the implant, prior to implantation in the eye. In other words, no separate "pushing" of the anchors is required to secure the implant. FIG. 4E to 4F illustrate an embodiment where the implant is unassembled. FIG. 4G illustrates an embodiment where the implant is assembled.

In these embodiments, by positioning the implant at the implantation location, the anchors penetrate tissue and secure the implant in place. With reference to FIG. 4E, holes 482 in housing 280 for receiving anchors 486 can be the same size or, alternatively, be different sizes for receiving different features. For example, one hole could receive an anchor 486, whereas another hole could receive a detachable dose canister, a permanent flow device, a flow anchor, or the like. In an embodiment, anchors 486 are constructed of titanium or other related materials. In a preferred embodiment, anchors 486 are approximately 1.5 mm long and 0.17 mm wide.

Figure 4H:
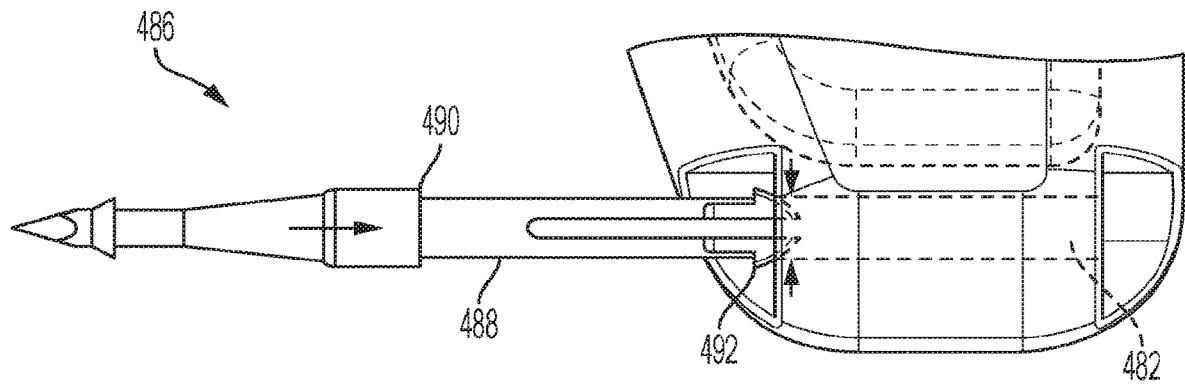
FIGS. 4H-4I illustrate top perspective views of an example embodiment of anchor insertion.
Figure 4I:
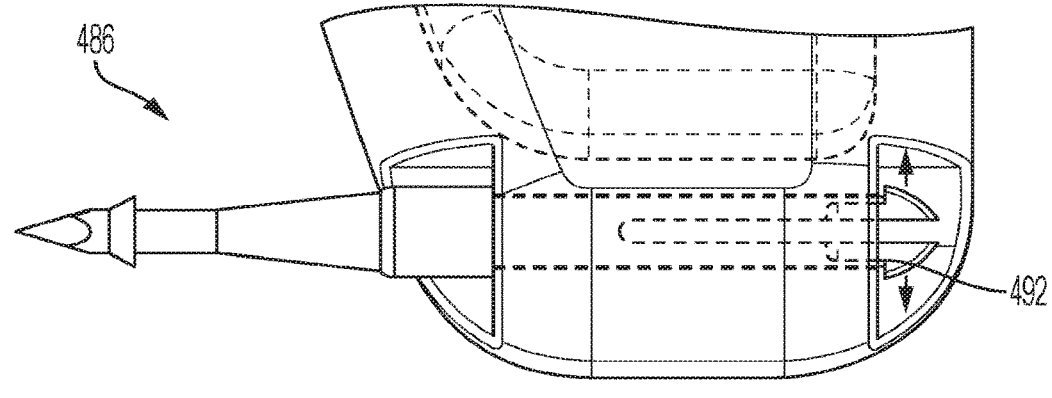
Figure 4J:
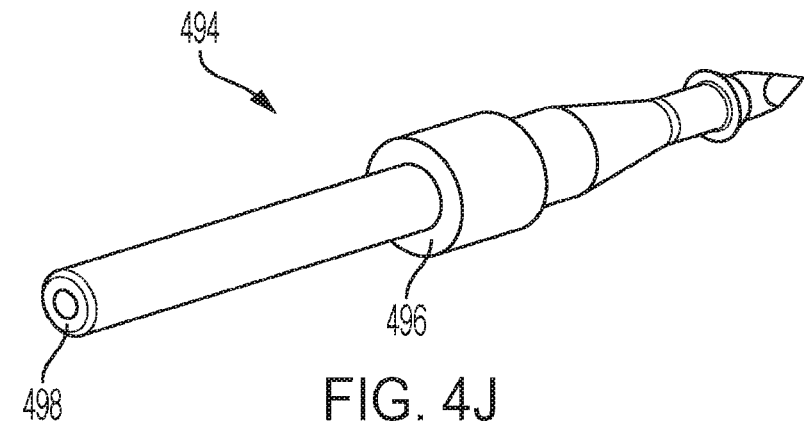
FIGS. 4J-4M illustrate top perspective views and cross-sectional side views of an example embodiment of anchor insertion.
Figure 4K:
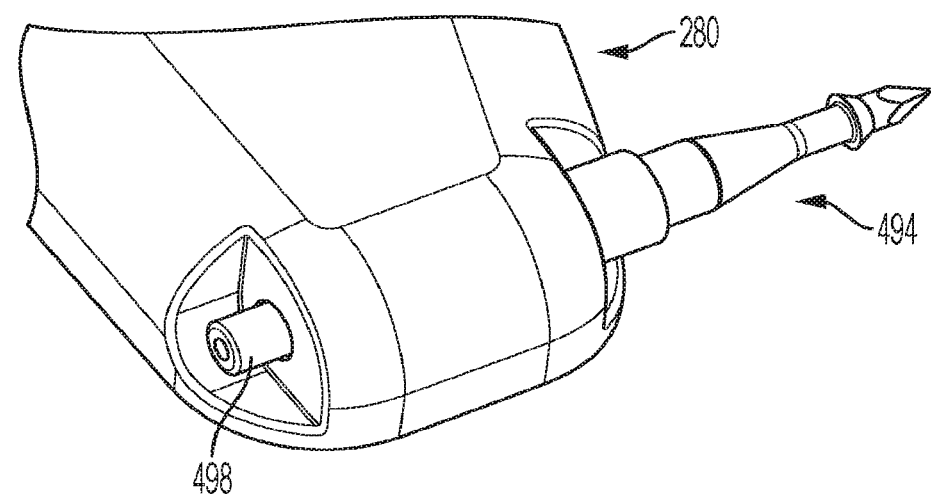
Figure 4L:
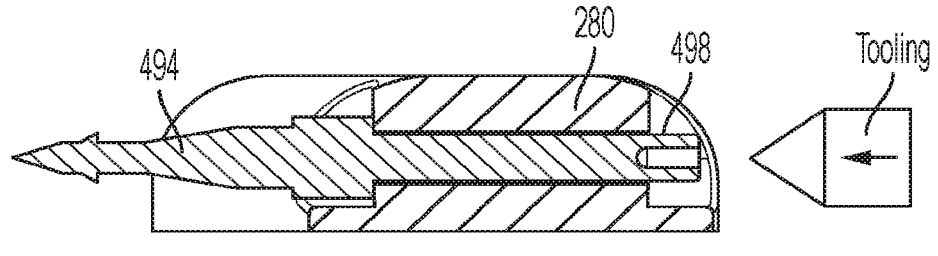
Figure 4M:
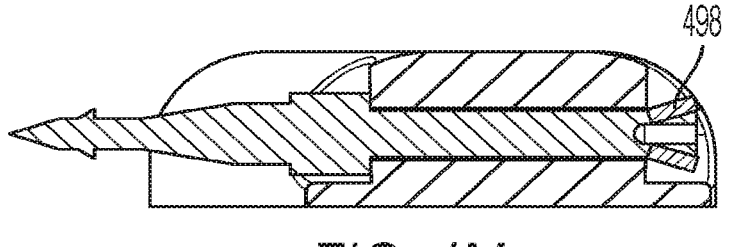
Figure 4N:
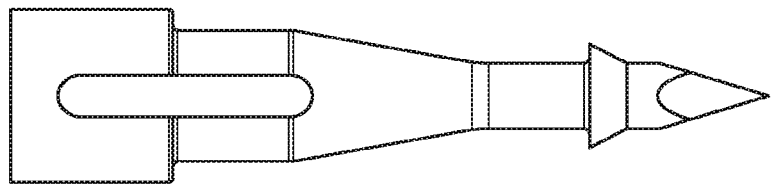
FIGS. 4N-4R illustrate side and top perspective views of example embodiments of anchors that include fluid flow passageways.
Figure 4O:
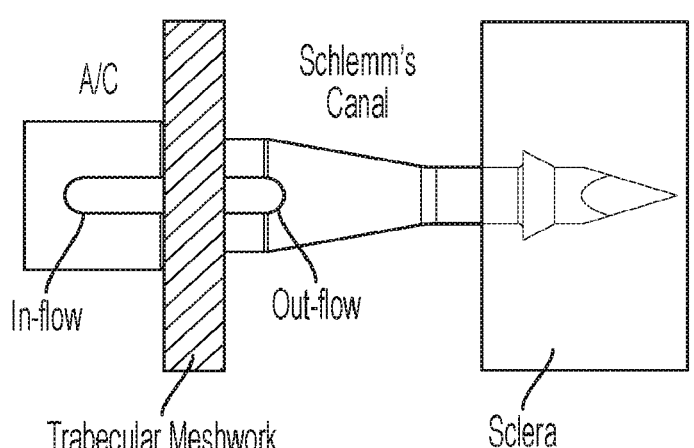
Figure 4P:
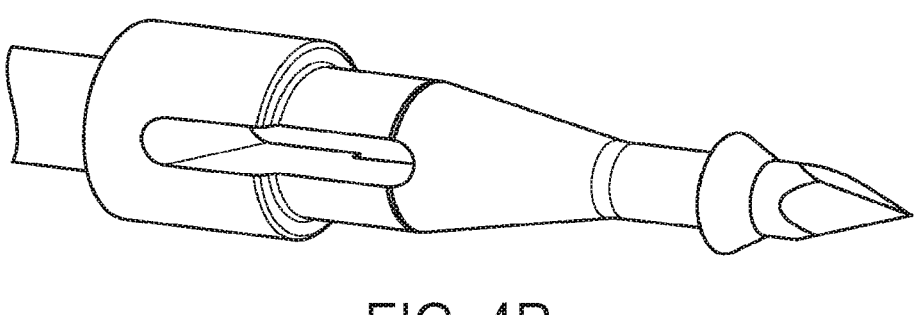
Figure 4Q:
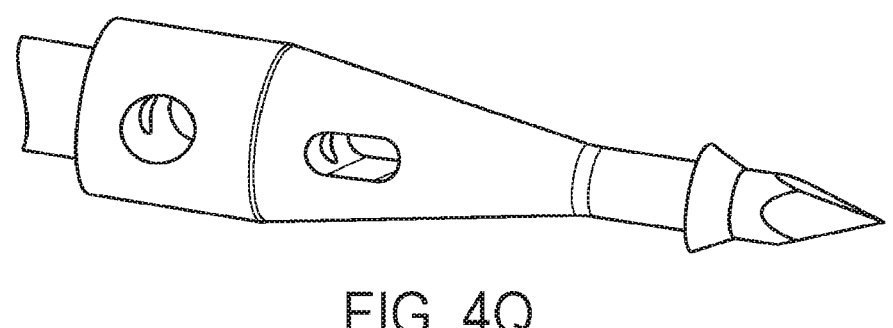
Figure 4R:
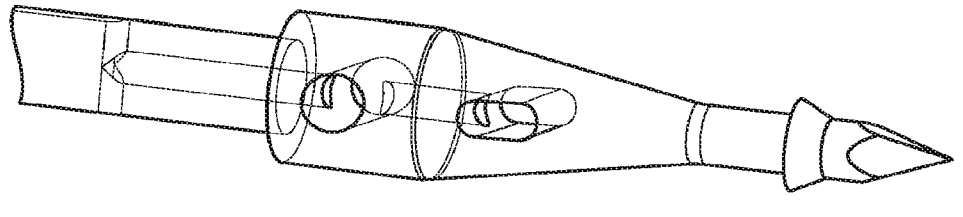

FIGS. 4H-4I illustrate the physical insertion of anchor 486 into anchoring tab 482 of housing 280, for assembly purposes. It should be appreciated that anchor 486 can be inserted into anchoring tab 482 of housing 280 prior to surgery or, alternatively, during surgery. Generally, the elongate body 488 of each anchor 486 has a diameter which is smaller than the diameter of the through hole in the corresponding anchoring tab 482, while the maximum diameters of penetrating head 490 and retention head 492 of the anchor 486 are larger than the diameter of the through hole. As a result, each anchor 486 can freely slide within the through hole of the corresponding anchoring tab, but the penetrating head 490 and the retention head 492 of the anchor 486 retain it so that it is captured in the anchoring tab 482. In some embodiments, the length of the elongate body 488 plus the length of the penetrating head 490 of each anchor 486 is at least as long as the thickness of the corresponding anchoring tab 482 plus the desired insertion depth of the penetrating tip in ocular tissue. In other embodiments, a portion of the anchor 486, such as a portion of elongate body 488 and retention head 492 includes a space or gap, so that the user and/or assembler can reduce the diameters of these components via pinching for insertion into anchoring tabs 482. In some embodiments, the retention head 492 is dimensioned with its space or gap so that it can be decoupled from the anchoring tabs 482 some time after implantation, if desired.

In related embodiments, housing 280 includes alternate or additional features for securing anchors 486. For example, housing 280 may include a figure-eight loop wire, instead of rigid holes. The figure-eight loop wire could be affixed to housing, and tightened by the surgeon when implanted, to securely fasten anchors 486 at the ends of the loop. Alternatively, housing 280 could include both rigid holes and a figure-eight loop wire for alignment and subsequent fastening.

In another embodiment, anchor 494 is affixed to housing 280 via alternate means. For example, FIGS. 4J-4M illustrate anchors 494 that do not include retention heads 492. In a preferred embodiment, anchors 494 are approximately 1.6 mm long and 0.2 mm wide. Specifically, anchors 494 are disposed within housing, such as via anchoring tabs 482 discussed previously herein. In this particular embodiment, anchors 494 are inserted into anchoring tab 482 of housing 280 prior to surgery. Generally, the elongate body of each anchor 494 has a diameter which is smaller than the diameter of the through hole in the corresponding anchoring tab 482, while the maximum diameters of penetrating head 496 is larger than the diameter of the through hole. As a result, each anchor 494 can freely slide within the through hole of the corresponding anchoring tab 482, but the penetrating head 496 of the anchor 494 retains it so that it is captured in the anchoring tab 482. Anchor 494 further includes a deformable end 498, which may further include a partial indentation, deformation, or hole. Once the anchor 494 is fully inserted within the through hole of the corresponding anchoring tab 482, the housing 280 and anchor 494 are fixedly secured to a workpiece. A carbide tip, or other similar mechanical tooling, is then pressed into the deformable end 498 of anchor 494, such that the deformable end 498 is mechanically deformed and results in a new, larger, diameter. In this way, by deforming anchor 494 at deformable end 498, anchor 494 is permanently fixed to housing 280. Once permanently fixed, anchor 494 and housing 280 can be implemented as described herein.

In various embodiments, anchors, such as anchor 486 or anchor 494, may be a drug eluting anchor and/or have one or more fluid flow passageways, to enhance outflow of aqueous humor from the eye, as illustrated by FIGS. 4N-4R. For example, the anchor may include one or more in-flow outlets, one or more out-flow outlets, and one or more fluid passageways connecting the in-flow outlets to the out-flow outlets. In an embodiment, once the anchor is inserted through the trabecular meshwork and anchored to the sclera, the in-flow outlet resides in the anterior chamber of the eye and the out-flow outlet resides in Schlemm's canal, such that the anchor conducts fluid from the anterior chamber to Schlemm's canal via the fluid flow passageway. In some embodiments, the fluid flow passageways are open channel passageways, such as those illustrated by FIGS. 4N-4P; with open channel passageways, the in-flow outlet, out-flow outlet, and fluid flow passageway are one single open passageway. In other embodiments, the fluid flow passageways are enclosed passageways, such as those illustrated by FIGS. 4Q-4R.

In an embodiment in which the anchor is a drug eluting anchor, it serves at least two functions: (1) securing the housing 280 (and entire sensor implant 200) to the ocular tissue; and (2) providing to the eye a slow-release drug elution into the anterior chamber to assist with any ocular medical condition requiring continuous medication, such as improving aqueous outflow and treating glaucoma. One such stand-alone drug eluting anchor is described in U.S. Patent Publication No. 2015/0342875, entitled "IMPLANTS WITH CONTROLLED DRUG DELIVERY FEATURES AND METHODS OF USING SAME," which is incorporated by reference herein. Although only discussed as a stand-alone drug eluting implant in U.S. Patent Pub. No. 2015/0342875, it should be appreciated that the anchor portion of the drug eluting implant could serve the additional purpose of securing to ocular tissue the intraocular sensor discussed herein or any other desirable ocular implant intended to remain static within the anterior chamber (or any other anatomical portion) of the eye.

Figures 5D, 5E:
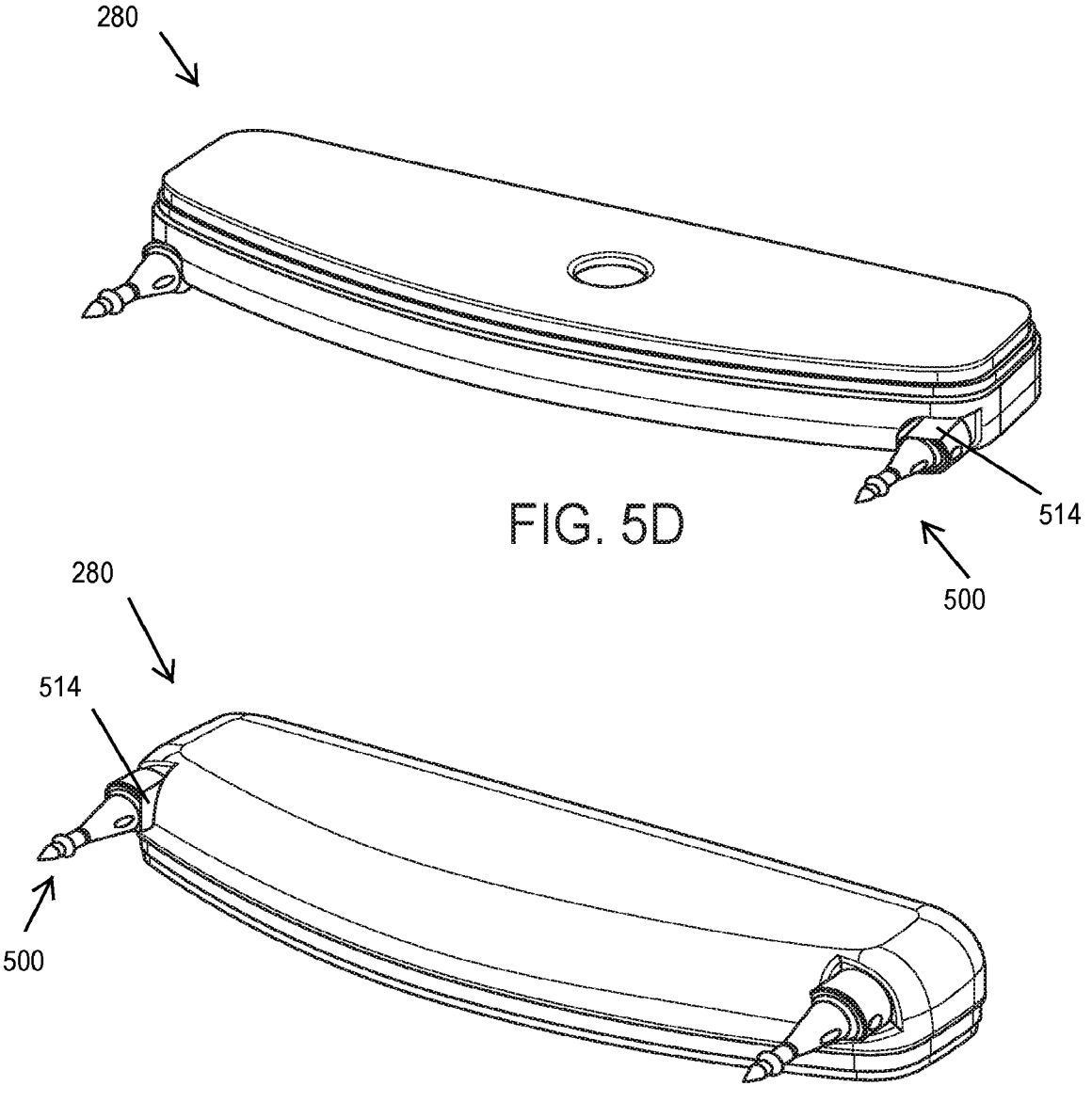
FIGS. 5D-5G illustrate perspective and front views of intraocular physiological sensor implants with anchors that include clocking features and fluid flow passageways
Figure 5F:
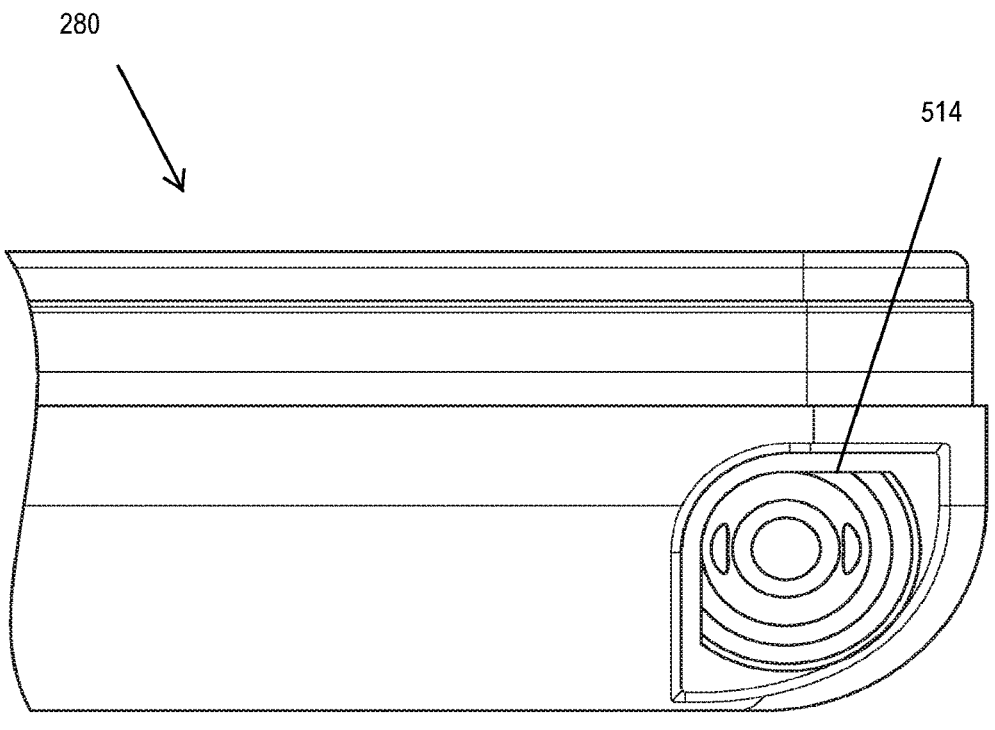
Figure 5G:
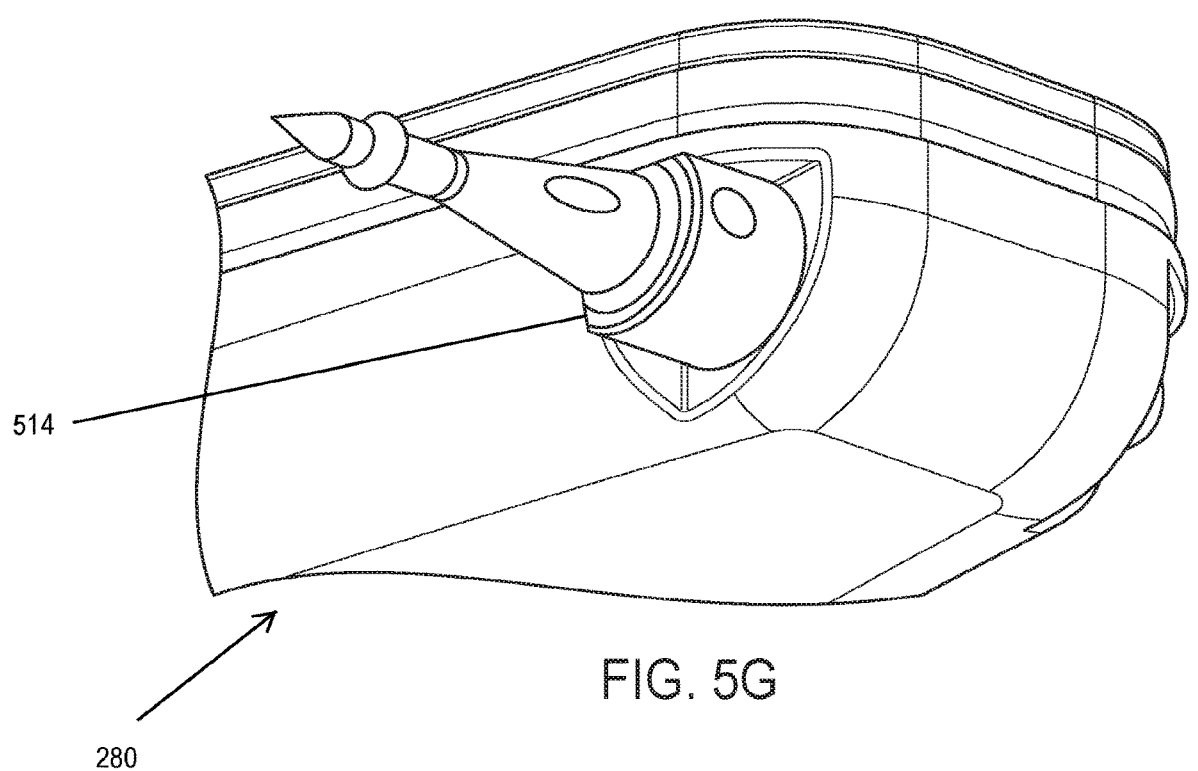

In a preferred embodiment, the anchors include several of the features discussed above. For example, the anchors may include one or more fluid flow passageways and may include a mechanically deformable end. In this preferred embodiment, the anchors further include a clocking feature. For example, FIGS. 5A-5C illustrate perspective, front, and cross-sectional side views of anchors 500 that include a clocking feature along with fluid flow passageways and mechanically deformable ends. FIGS. 5D-5G further illustrate additional perspective and front views of intraocular physiological sensor implants, including anchors 500 that include clocking features and fluid flow passageways as discussed herein. Specifically, anchor 500 includes elongate body 502, retention head 504, and penetrating head 506 (as previously discussed above). Furthermore, anchor 500 includes at least one fluid flow passageway having in-flow outlets 508 and out-flow outlets 510. In an embodiment, the fluid flow passageway between in-flow outlets 508 and out-flow outlets 510 is angled as it passes through retention head 504. Once the anchor 500 is inserted through the trabecular meshwork, and anchored to the sclera, the in-flow outlets 508 reside in the anterior chamber of the eye and the out-flow outlets 510 reside in Schlemm's canal, such that the anchor 500 conducts fluid from the anterior chamber to Schlemm's canal via the fluid flow passageway.

In this preferred embodiment, anchor 500 further includes a staking feature 512. For example, staking feature 512 is a deformable end, which may further include a partial indentation, deformation, or hole. Once the anchor 500 is fully inserted to housing 280, the staking feature 512 is deformed (as discussed in greater detail above with respect to deformable end 498), to affix anchor 500 to housing 280 (or housing 480).

Furthermore, in this preferred embodiment, anchor 500 further includes a clocking feature 514. For example, clocking feature 514 may be a specific geometric profile, such as a bevel, chamfer, fillet, or other rounded edge, on the surface of retention head 504 of anchor 500. Housing 280 may, likewise, include a similar geometric profile, such that the clocking feature 514 on retention head 504 matches with housing 280. Clocking feature 514 prevents the anchor 500 from inadvertently twisting once it is inserted into housing 280. By preventing twisting of anchor 500, clocking feature 514 ensures that in-flow outlets 508 and out-flow outlets 510 are properly aligned with respect to housing 280 and related anatomical features in the ocular environment, thus ensuring proper flow and drainage across the fluid flow passageway.

Figure 5H:
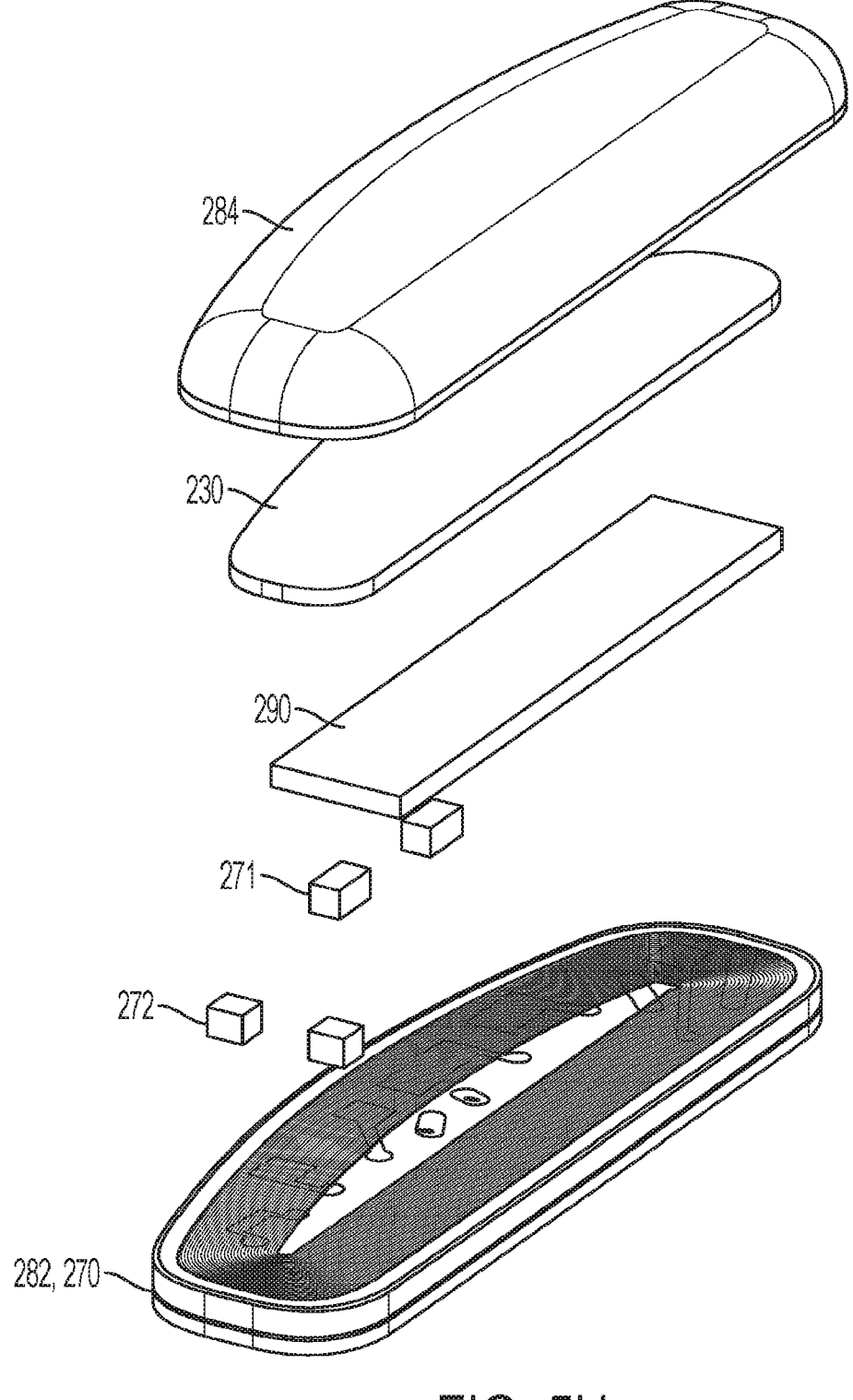
FIG. 5H illustrates an exploded view of an example embodiment of an intraocular physiological sensor implant.

FIG. 5H shows an exploded view of an example embodiment of the intraocular physiological sensor implant 200. It should be appreciated that certain structure previously described, such as anchors 286, 486 are included, though not illustrated in several of the remaining figures. In the illustrated embodiment, the faceplate 282 includes an electrical interconnect circuit 270 (described in more detail below). Conductive posts 272 and surface mount capacitors 271 are provided on the electrical interconnect circuit 270. The integrated circuit 290 and the battery 230 are then provided on the faceplate 282 in a stacked configuration. The top cover 284 is then joined together with the faceplate 282 to form the sealed housing 280.

Figure 5I:
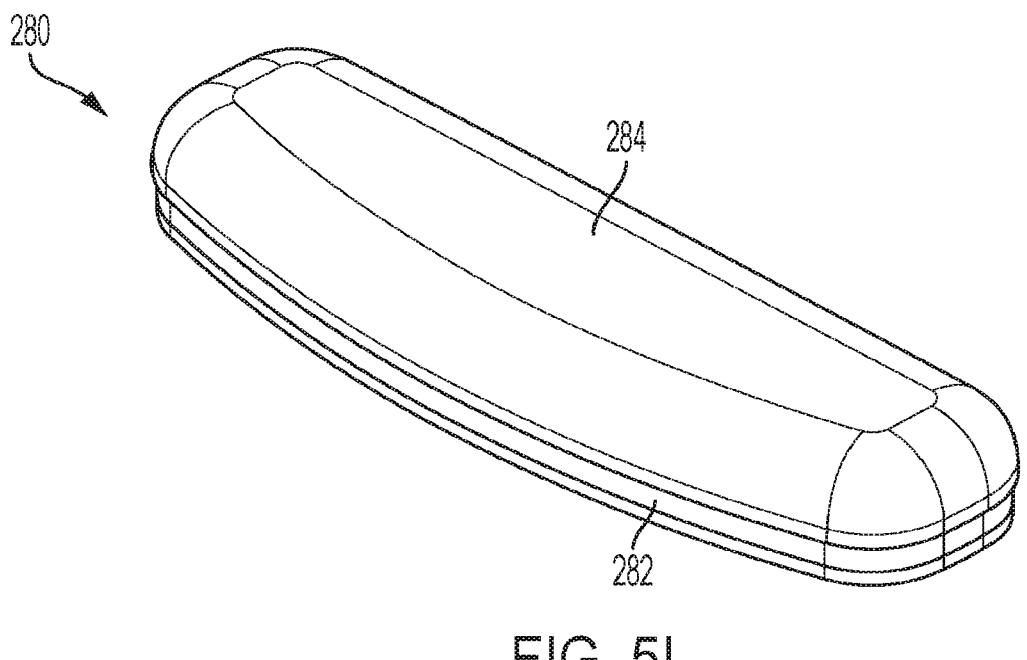
FIGS. 5I-5L illustrate layer-by-layer perspective views of the example embodiment of the intraocular physiological sensor implant shown in FIG. 5H.
Figure 5J:
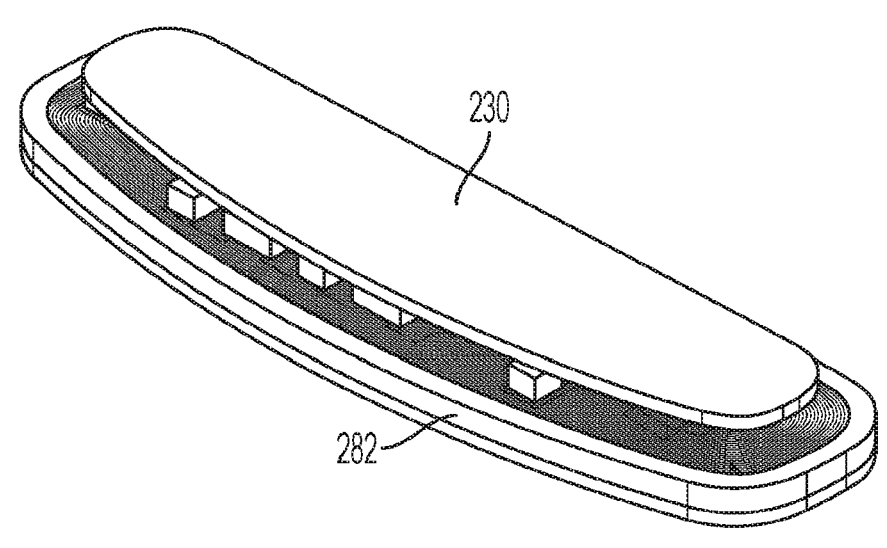

FIGS. 5I-5L are layer-by-layer perspective views of the example embodiment of the intraocular physiological sensor implant 200 shown in FIG. 5H. In FIG. 5I, the complete housing 280 is shown with the faceplate 282 and the top cover 284 joined together to enclose the battery 230, the integrated circuit 290, and the other components of the sensor implant 200. In FIG. 5J, the top cover 284 of the housing 280 is shown removed. In the illustrated embodiment, the battery 230 is provided at the top of a stack of electrical components for the sensor implant 200. In some embodiments, the battery 230 is a thin-film rechargeable lithium-ion or lithium-metal battery. The illustrated embodiment of the battery 230 includes electrical contacts on its bottom surface to connect with battery connection posts 272, which are in turn connected to the electrical interconnect circuit 270, such as via conductive epoxy. During assembly, battery connection posts 272 may be accessed for testing of system integrity and additional battery 230 calibration, such as critical voltage threshold testing. For example, some of the connection posts 272 may be implemented specifically for power-purposes, serving as cathodes and anodes; other connection posts 272 may be testing or calibration posts. In various embodiments, the programming and calibration that is enabled via one or more of the posts 272 also includes marking the device's serial number. It should be appreciated that the posts 272 also provide a level surface upon which the battery is mounted. Having a level surface is beneficial, for example, when interrogating with a probecard for probing several electrical pads at once and/or for testing fixtures.

Figure 5K:
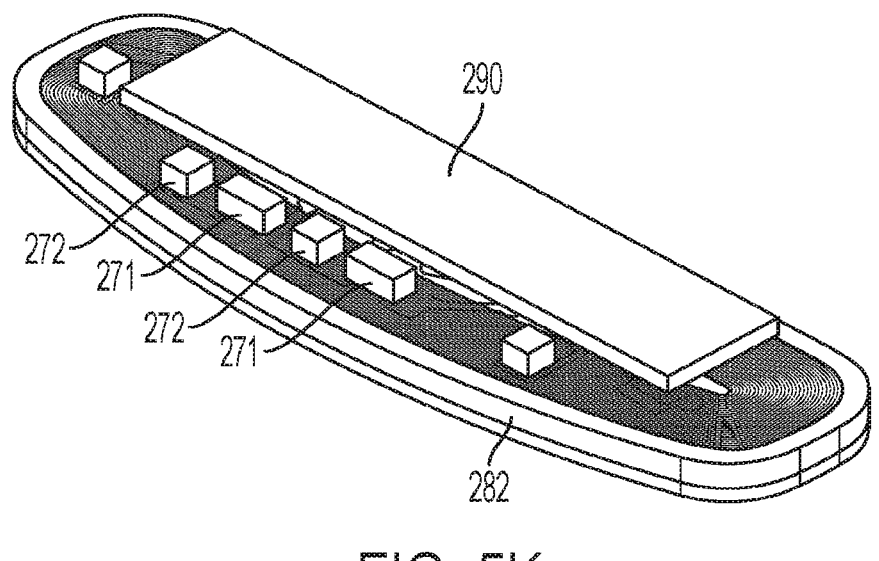
Figure 5L:
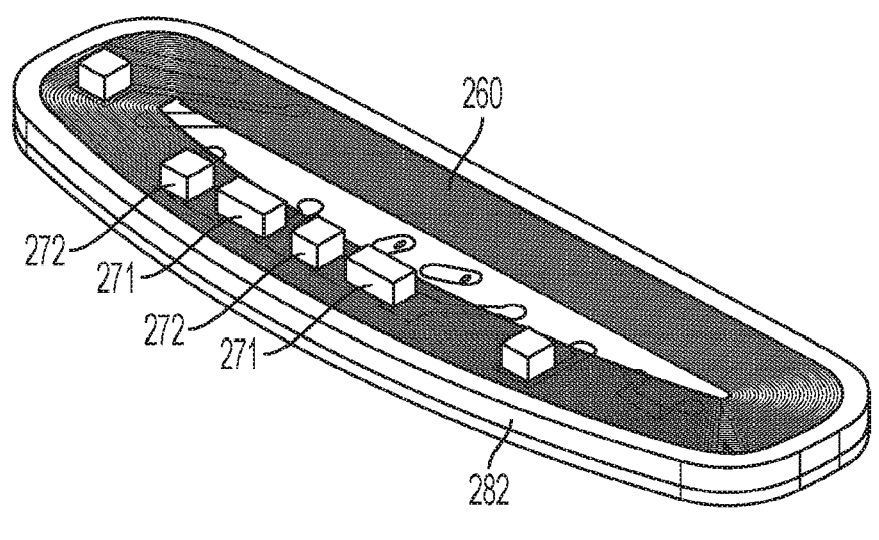

In FIG. 5K, the battery 230 has been removed to reveal the integrated circuit 290. As already discussed, the integrated circuit 290 can include, for example, the controller 220, the measurement memory 240, the transceiver/receiver 250, the capacitance-to-digital converter 212, and other related components. In FIG. 5L, the integrated circuit 290 has been removed to reveal the electrical interconnect circuit 270, embodiments of which are described in more detail below. FIG. 5L also shows the coil 260. In the illustrated embodiment, the coil 260 is embedded into the faceplate 282, as described below.

Figure 6A:
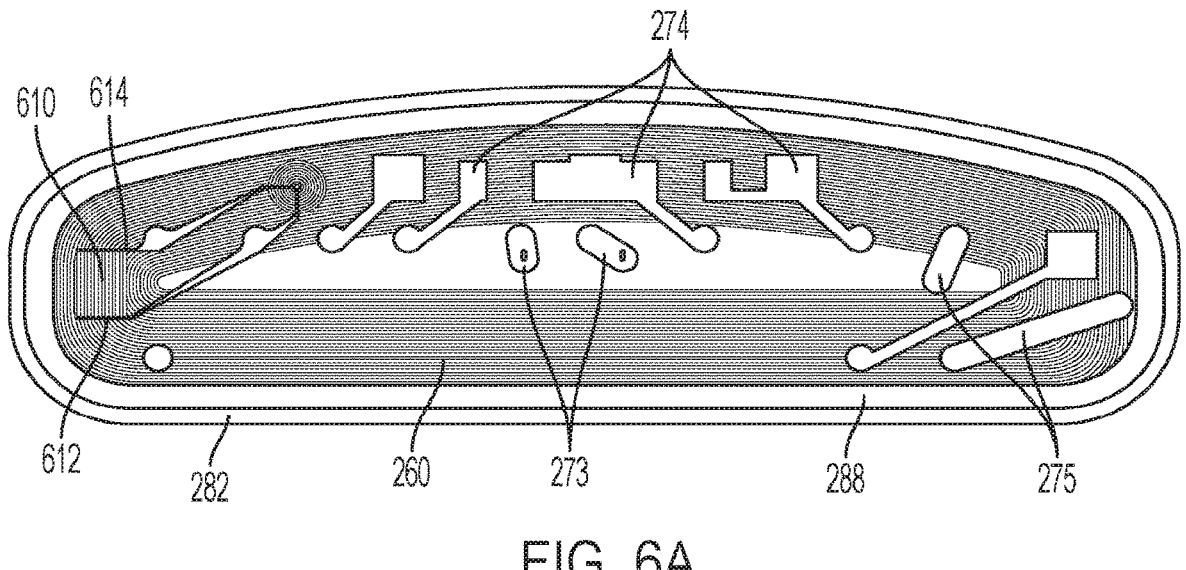
FIGS. 6A-6D illustrate layer-by-layer top views of the example embodiment of the intraocular physiological sensor implant shown in FIG. 5H.

FIGS. 6A-6D are layer-by-layer top views of the example embodiment of the intraocular physiological sensor implant 200 shown in FIG. 5H. FIG. 6A is a top view which shows the inside surface of the faceplate 282. As discussed further herein, a hermetic seal 288 can be formed around the perimeter of the inside surface of the faceplate 282. The electrical interconnect circuit 270 can be formed in or on the inside surface of the faceplate 282. The electrical interconnect circuit 270 can include various conductive pads 274 and traces for making electrical connections between the various electrical components of the sensor implant 200. These conductive pads and traces can be provided on the inside surface of the faceplate 282 over the embedded copper loops of the coil 260. An insulation layer can be provided atop the embedded copper coils of coil 260 to electrically insulate it from the electrical interconnect circuit 270. This insulation layer can be, for example a polymer such as polyimide, parylene, photoresist or other photopatternable polymers including SU-8, BCB, or photopatternable polyimide. The insulation layer can also be an oxide or nitride layer such as silicon oxide deposited by physical vapor deposition (PVD), for example. Other insulations layers are possible. In the illustrated embodiment, the electrical interconnect circuit 270 includes two electrical pads 273 which are connected to conductive vias which pass through the faceplate 282 and connect with the electrodes of the physiological sensor 210.

FIG. 6A shows the coil 260, which, in the illustrated embodiment, consists of conductive loops, such as copper, silver, gold, platinum, tungsten, low-resistivity silicon, such as silicon doped with impurities such as boron or phosphorous, or the like, embedded into the inside surface of the faceplate 282. In a preferred embodiment, coil 260 is entirely recessed into faceplate 282 such that its top surface is flush with the surface of faceplate 282. In the preferred embodiment, coil 260 is electrically insulated from the bulk material of faceplate 282 by a liner oxide, nitride, or other insulating material, such as polymeric material, that is deposited onto the silicon before the structure is filled with the conductive material (e.g., copper, silver, or other related materials) via a sputtering, plating, or other deposition method. This liner material electrically isolates the coil 260 from the faceplate 282. In some embodiments, further design elements are included for the purpose of improving the electrical isolation of the coil 260 from faceplate 282. For example the insulating liner material may be made purposefully thick specifically for this reason. For example, a thick insulating layer of oxide of several microns may be grown or deposited on the silicon surface of faceplate 282, or the silicon structure can be entirely converted to a silicon dioxide structure by thermal conversion before deposition of the coil conductor. As a further approach to minimize parasitic capacitance and or eddy current effects in the silicon material near the coil 260, the faceplate 282 may be designed such that there is an air or vacuum gap underneath and/or above the coil in its final arrangement by selective removal of the silicon of faceplate 282 during the fabrication processes. In some embodiments, the embedded coil 260 does not necessarily require that the faceplate 282 be made thicker than it otherwise would in view of structural concerns such as stiffness and strength. Thus, by embedding the coil loops into the inside surface of the faceplate 282, the housing 280 can be made smaller because little or no additional room for the coil 260 is required inside the housing as would be required if the coil was provided as a discrete component from the faceplate 282. In an alternate embodiment, coil 260 and interconnect circuit 270 are provided as a discrete component as a flexible circuit as discussed in conjunction with FIGS. 9A to 9D below. In yet another embodiment, the coil 260 and interconnect circuit 270 are provided as a discrete component that is rigid, such as a coil embedded in a thin, free-standing piece of silicon, or in other rigid material such as glass, or rigid polymer such as epoxy, BCB, or SU-8. The flexible circuit 900 or any other discrete component may advantageously avoid certain thermal expansion characteristics described in greater detail herein. The flexible circuit 900 may advantageously avoid certain thermal expansion characteristics described in greater detail herein. For example, one single piece flexible circuit 900 is beneficial. In addition, or alternatively, by embedding the coil 260 in the faceplate 282, the conductive material which makes up the coil loops can be made thicker because doing so does not necessarily occupy additional space beyond that which would have already been occupied by the faceplate. The thickness of the conductive material as well aspect ratio (thickness-to-width of the embedded conductive material) may also be made greater by embedding the coil in the faceplate 282, than could otherwise be achieve using an additive process to fabricate a coil on top of the faceplate. The increased thickness of the conductive material makes the coil 260 have lower electrical resistance, which improves its quality factor or efficiency. In addition, a larger number of turns improves the inductance of the coil 260, also improving efficiency. The ends of the conductor which makes up the coil 260 can be connected to conductive pads 274 provided as part of the electrical interconnect circuit 270 so as to connect the coil with other components of the sensor implant 200, specifically the integrated circuit 290.

FIG. 6A also shows a humidity sensor 610 provided on the inside surface of the faceplate 282. The humidity sensor 610 can be used to detect moisture inside the housing 280. This can be useful for purposes of detecting failure or impending failure of the sensor implant 200 due to breach or failure of a hermetic seal or housing 280 because some of its components, like the battery 230, may suffer reduced operative lifetime, reduced performance, or even malfunction if exposed to too much moisture. In the case of a very slow leak of moisture inside the housing 280, the humidity sensor 610 may provide significantly advanced notice of the leak than otherwise would be possible.

In some embodiments, the humidity sensor 610 can be a capacitor which includes spaced-apart comb-like electrodes, such as the interdigitated electrodes 612, 614 shown in FIG. 6A. A moisture-sensitive dielectric material can be placed between, on, or around the electrodes 612, 614. The capacitance of the humidity sensor 610 will be dependent on the dielectric constant of the moisture-sensitive dielectric material. Thus, if a material whose dielectric constant changes when exposed to moisture is used, then moisture inside the housing 280 can be detected by detecting a change in the capacitance of the humidity sensor 610. In one embodiment, there is not a dielectric material applied atop the interdigitated electrodes, but the change in dielectric constant of the air itself inside the implant is sensed as the moisture content in the air increases. The number of fingers or branches, as well as the spacing between fingers or branches, of comb-like interdigitated electrodes 612, 614 may be adjusted and designed to generate a specific range of capacitance based upon the capacitance sensitivity of the integrated circuit. In some embodiments, the humidity sensor 610 includes as many as ten or twenty or more fingers or branches on each of its sides. By increasing the number of fingers or branches, the humidity sensor 610 has increased sensitivity and outputs a capacitance signal high enough to be registered by the integrated circuit.

In some embodiments, a getter material can be provided inside the housing 280. The getter material, such as a desiccant material, can be used to absorb, adsorb, or chemically combine with moisture, gases, and the like, so as to keep those contaminants away from sensitive components inside the housing 280 and maintain a suitable operating environment. Such a getter material would be useful even in the absence of the humidity sensor 610 because even moisture-impermeable materials, such as ceramic, may allow some moisture to pass through (depending on thickness) if they are exposed to moisture over an extended period of time, such as years or decades. Such a getter material is also useful to remove, absorb, adsorb, or chemically combine, residual gases or moisture that are entrapped within the implant during the hermetically operation of the faceplate to the housing. For example, even if the implant assembly and sealing processes are performed under a vacuum or inert gas environment such as helium, argon, or nitrogen, residual other gases and water vapor will nonetheless be inadvertently trapped. Such entrapped species may otherwise react with the battery, degrading its performance, or with the integrated circuit causing its performance to drift over time. Additionally, gases and/or moisture will outgas from the various components or from the surfaces of the various components in the internal implant volume over time. These components include the faceplate itself, the integrated circuit, flexible coil circuit, and the conductive epoxies used for interconnections. In embodiments which include the humidity sensor 610, however, the getter material can be used as the moisture-sensitive dielectric material for the humidity sensor, thereby achieving a synergistic effect of not only removing or isolating moisture inside the housing 280 but also making it possible to detect such moisture. The getter material can be, for example, a sorbing species suspended in a carrier material that can be dispensed or deposited atop the interdigitated electrodes. For example sorbing particles, such as a made of metal or metal alloy that reacts with nitrogen, oxygen, water vapor, and the like, or microporous or nanoporous particles, such as zeolite mineral, that absorb gas or water vapor, can be suspended in liquid adhesive that is dispensed over the interdigitated electrodes. Although the getter material can be used as the moisture-sensitive dielectric material for the humidity sensor 610, this is not necessarily required. The getter material can be placed elsewhere, or throughout, the housing 280. The getter can be provided in the housing 280 as, for example, a paste or a surface coating or a preformed solid component, known as a preform.

The capacitance of the humidity sensor 610 can be determined using a capacitance-to-digital converter. In some embodiments, the same capacitance-to-digital converter 212 which is used to read the capacitive pressure sensor 210 can also be connected to the humidity sensor 610 and used to read its capacitance. In this way, the space, costs, and/or complexity of an additional capacitance-to-digital converter can be avoided.

The capacitance of the humidity sensor 610 can be read by the controller 220 periodically, according to a set schedule, and/or on demand, such as whenever intraocular pressure measurements are downloaded from the sensor implant 200 by an external device or when the battery 230 is recharged by the external device the capacitance of humidity sensor 610 could also be read. By tracking the capacitance of the humidity sensor 610 over time, moisture inside the housing 280 can be detected. For example, the controller 220 and/or an external device can determine if the capacitance of the humidity sensor 610 changes over time by an above-threshold amount. Based on measurements from the humidity sensor 610, the failure or impending failure of the sensor implant 200 can be identified.

Measurements from the humidity sensor 610 can also be used during manufacturing in order to ensure the integrity of the hermetic seal 288. During manufacturing, the faceplate 282 and the top cover 284 can be sealed together in a dry environment. The humidity sensor 610 can then be used to observe any extraneous moisture inside the sealed housing. An initial capacitance value can be read from the humidity sensor 610 after sealing the housing 280. A subsequent capacitance value can then be read from the humidity sensor 610 at a time later and can be compared to the initial capacitance value. Optionally, the housing 280 can be exposed to external high moisture environment and also optionally increased pressure in order to accelerate any moisture ingress through a defective hermitic seal 288. If there is an above-threshold change in the capacitance of the humidity sensor 610, then the failure of the hermetic seal 288 can be advantageously detected before the sensor implant 200 is surgically implanted in a patient's eye.

Figure 6B:
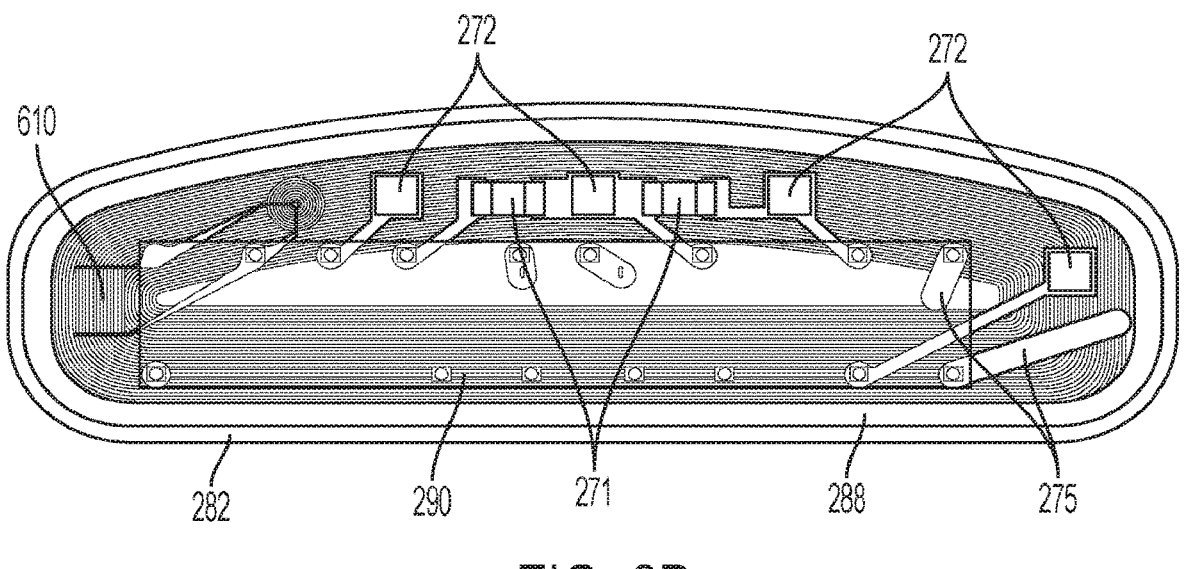

FIG. 6B is a top view which shows the integrated circuit 290 (shown with semi-transparent shading) stacked in position on top of the faceplate 282. As illustrated, the bottom surface of the integrated circuit 290 can include multiple electrical contacts, such as pads, connectors, or the like, to make electrical connections between the integrated circuit and the underlying electrical interconnect circuit 270.

FIG. 6B shows conductive posts 272 positioned on top of some of the pads of the electrical interconnect circuit 270. The conductive posts 272 can be used to make connections with components, such as the battery 230, higher up in the stacked configuration of components inside the housing 280 of the sensor implant 200. The battery 230 is connected to the interconnect circuit 270 and to the conductive posts 272 with conductive epoxy. The conductive pillars may provide probing locations for use during assembly to interface with the integrated circuit. FIG. 6B also shows the surface mount capacitors 271 positioned in place. In an embodiment, surface mount capacitors 271 are configured to absorb frequency spikes, such as those associated with decoupling responsive to digital logic switching.

Figure 6C:
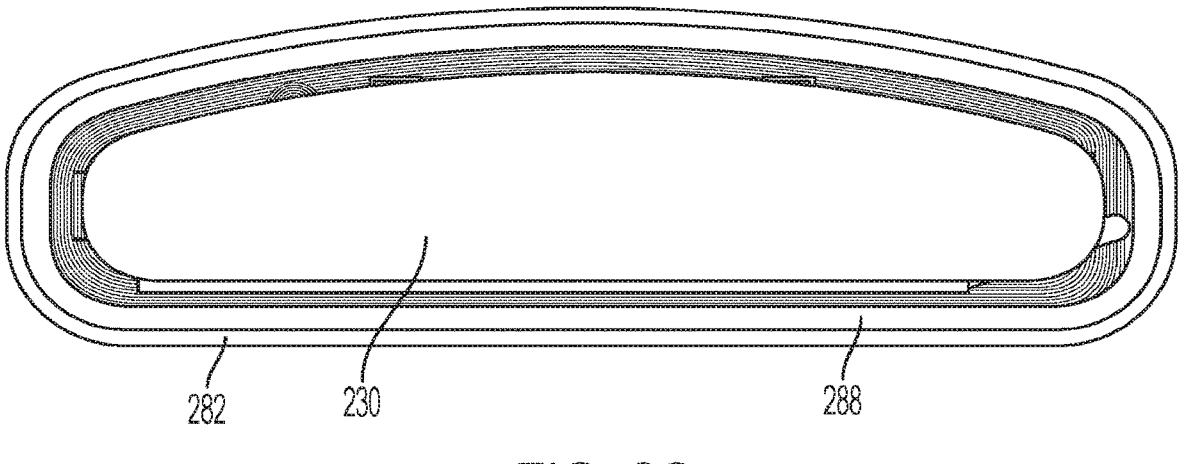
Figure 6D:
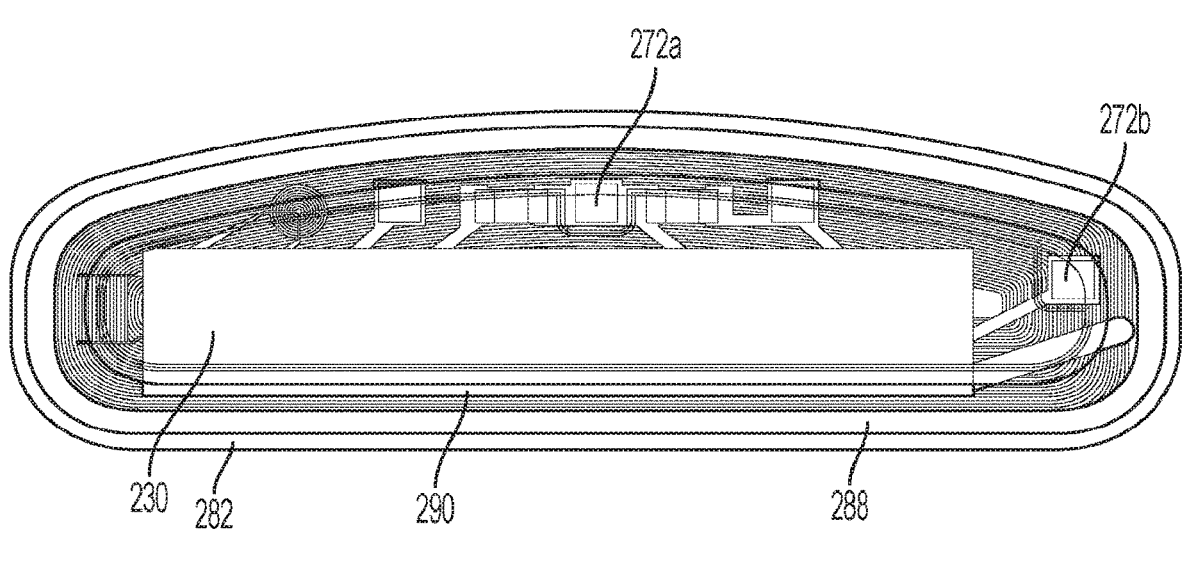

FIG. 6C is a top view which shows the battery 230 stacked in position on top of the integrated circuit 290. FIG. 6D is the same view as FIG. 6C except that the battery 230 is shown with semi-transparent shading to reveal electrical connections made underneath the battery at its bottom surface. Conductive post 272a is connected to the anode contact of the battery 230, while conductive post 272b is connected to the cathode contact. These connections can be made using, for example, conductive epoxy. It should be appreciated that the anode contact tracing 272a may be larger as compared to the cathode contact tracing 272b so that it can be used to ensure the backside of interconnect circuit 270 has a more reliable grounding to the system. Additional conductive pillars may be included, which do not make connection with battery 230. For example, these additional conductive pillars can be used during programming of sensor implant 200, such as programming of the ASIC during assembly, tuning voltages of the battery 230 and related components, trimming current and voltages, and the like.

Figure 7A:
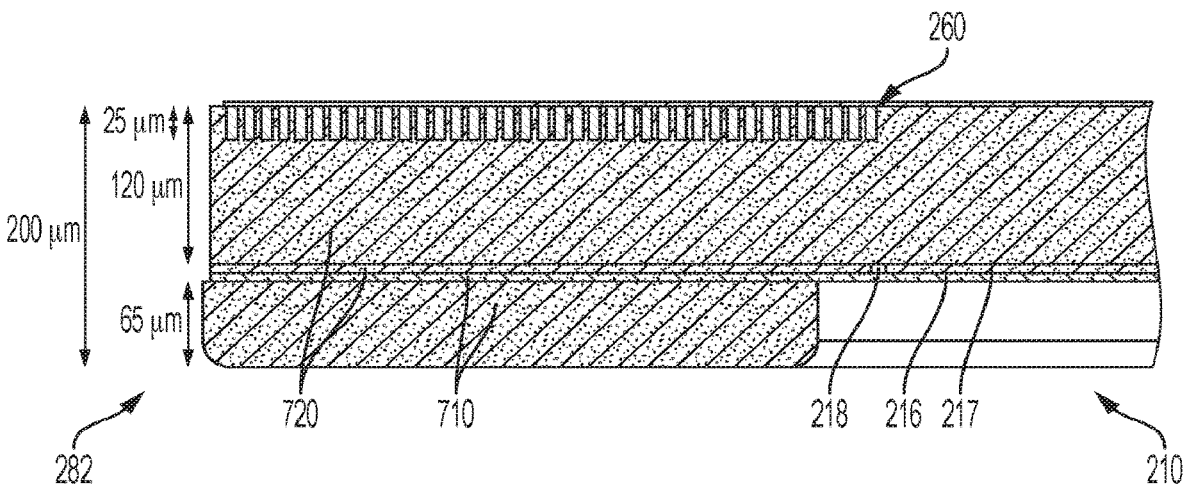
FIG. 7A illustrates a cross-sectional view of a portion of an example faceplate for the housing of an intraocular physiological sensor implant.

FIG. 7A is a cross-sectional view of a portion of an example faceplate 282 for the housing 280 of the intraocular physiological sensor implant 200. In some embodiments, the faceplate 282 can include a stacked configuration of silicon substrates 710, 720, 730 or even more stacked substrates. In the illustrated embodiment, the total thickness of the faceplate 282 is 200 μm, though in other embodiments the thickness of the faceplate can be, for example, 50 μm to 300 μm. Each of the silicon substrates 710, 720, 730 can be a bulk silicon layer or a high-conductivity silicon layer, which can be formed, for example, by adding suitable dopants to the bulk silicon and/or using polycrystalline silicon. In the illustrated embodiment, the bottom substrate 710 is a bulk silicon layer that is 65 μm thick, the middle silicon substrate 720 is a high-conductivity silicon layer that is 10 μm thick, and the top substrate 730 is a bulk silicon layer that is 120 μm thick, though other thicknesses can also be used.

The conductive loops which form the coil 260 can be embedded in the top surface of the bulk silicon layer of the top substrate 720 (which corresponds to the inner surface of the faceplate 282). In the illustrated embodiment, the loops of the coil 260 are embedded in channels formed in the bulk silicon layer of the top substrate 720 to a depth of 25 μm, with a width of 8 μm and a 4 μm gap between loops of the coil 260. Other depths and related dimensions can also be used, however.

As shown, the top and bottom silicon substrates 710, 720 can be stacked and bonded together with the high-conductivity silicon layers facing one another. The bulk silicon layer of the bottom substrate 710 can be etched away or otherwise removed in the region of the capacitive pressure sensor 210, thereby exposing the high-conductivity silicon layer of the bottom substrate in that region. In some embodiments, the high-conductivity silicon layers can have a thickness of 1 μm to 20 μm. The thicknesses of the two layers may be the same or different thicknesses.

The high-conductivity silicon layers can serve as the two electrodes 216, 217 for the capacitive pressure sensor 210. In the illustrated embodiment, the high-conductivity silicon layer of the bottom substrate 710 serves as the flexible diaphragm electrode 216, while the high-conductivity silicon layer of the top substrate 720 serves as the counter electrode 217 for the capacitive pressure sensor 210. Although the two electrodes 216, 217 appear in FIG. 7A to be in contact with one another, there is a gap between them in at least the region of the pressure sensor 210. The gap between the two electrodes 216, 217 can be, for example, 0.05 μm to 2 μm. This gap can be formed by having etched away or otherwise removed a portion of the thickness of the high-conductivity silicon layer which serves as the counter electrode 217 in the region above the flexible diaphragm electrode 216. The gap can also be formed by having removed a portion of the thickness of the flexible diaphragm electrode 216 in a similar manner. The gap between the flexible diaphragm electrode 216 and the counter electrode 217 can be a sealed vacuum or the gap can be filled with air or another gas to a desired pressure.

An isolation trench 218 can be formed around the counter electrode 217 so as to electrically isolate it from the flexible diaphragm electrode 216. Conductive vias can be formed through the bulk silicon layer of the top substrate 720 in order to electrically connect the electrodes 216, 217 of the capacitive pressure sensor 210 to the conductive pads 273 of the electrical interconnect circuit 270.

In an embodiment, the faceplate 282 includes an additional capacitive sensor that includes a second set of two electrodes 216, 217 and gap between, in the same manner as capacitive pressure sensor 210. The additional capacitive sensor is further connected to another pair of conductive vias 219 and pair of conductive pads 273, which can be used to connect the additional capacitive sensor to the integrated circuit 290 in the same manner as capacitive pressure sensor 210. However, unlike capacitive pressure sensor 210, which includes an opening in bottom layer substrate 710 so that pressure can act on flexible diaphragm electrode 216 and cause it to deflect in response to pressure changes, the additional capacitive sensor does not include an opening in bottom layer substrate 710. Rather, the bottom layer substrate 710 is continuous across the sensor location and prevents the electrode 216 (of the additional capacitive sensor) from moving in response to changes in external pressure.

While the additional capacitive sensor does not respond to external pressure changes, it can be used to detect strain within the faceplate 282, such as strain caused by bonding stresses created during the attachment of faceplate 282 to housing 284 to create sealed housing 280, stresses created by coefficient of thermal expansion (CTE) mismatch between faceplate 282 and housing 284, or other stresses acting on the faceplate 282 that may be resultant from temperature changes, or the like. Such stresses can cause strain in the faceplate 282 that will affect the output of capacitive pressure sensor 210 and may lead to inaccuracies in its measurement of pressure. The inclusion of the additional capacitive sensor enables the strain in the faceplate 282 to be measured and this information can be used to compensate or correct the output of capacitive pressure sensor 210 to obtain more accurate pressure measurements. In certain embodiments, the additional capacitive sensor can be used as a temperature sensor by measuring the effects described above and ascribing them to changes in temperature. Its output can be calibrated when used as such.

Figure 7B:
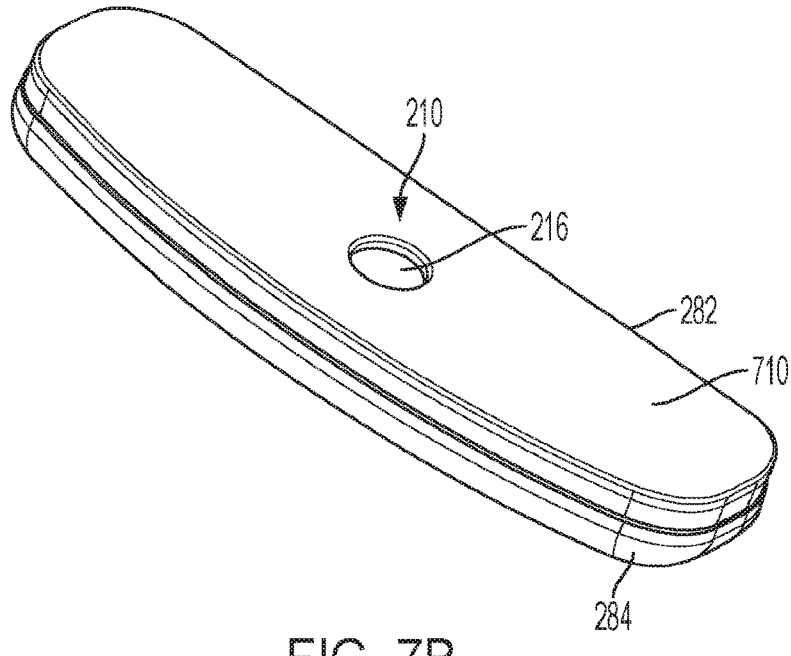
FIG. 7B illustrates a perspective view of an embodiment of an intraocular physiological sensor implant in which the physiological sensor is recessed in the faceplate.

FIG. 7B illustrates an embodiment of the intraocular physiological sensor implant 200 in which the physiological sensor 210 is recessed in the faceplate 282. As discussed above with respect to FIG. 7A, the bulk silicon layer of the bottom substrate 710 can be removed in the region of the capacitive pressure sensor 210, thereby exposing the high-conductivity silicon layer of the bottom substrate to serve as the flexible diaphragm electrode 216. As shown in FIG. 7B, this results in the capacitive pressure sensor 210 being recessed from the exterior surface of the faceplate 282 (i.e., the bottom surface of the bulk silicon layer of the bottom substrate 710). The depression in the faceplate 282 has a sidewall whose height corresponds to the removed thickness of the bulk silicon layer of the bottom substrate 710. As the flexible diaphragm electrode 216 may be delicate, its location in this depression in the faceplate 282 offers a measure of protection against damage when the implant is being handled or manipulated prior to, and during, surgical implantation.

Although the recessed location of the flexible diaphragm electrode 216 may be advantageous for its protective properties, it may also pose some complications which could affect the capability of the capacitive pressure sensor 210 to operate within the eye. For example, the depression in the faceplate 282 may have a tendency to trap an air pocket adjacent to the flexible diaphragm electrode 216 when the sensor implant 200 is inserted into the patient's eye. Although an air pocket may at least partially transmit pressure from the aqueous humor to the flexible diaphragm electrode 216, it is also possible that an air pocket which fills, or partially fills, the depression in the faceplate 282 may negatively impact the accuracy of IOP measurements due to forces generated by surface tension at the interfaces of the air pocket and aqueous humor and/or flexible diaphragm electrode 216, or due to other effects such as affecting the parasitic capacitance acting on the capacitive pressure sensor 210.

This potential problem may be at least partially ameliorated by providing a hydrophilic coating on the inside of the depression. For example, the peripheral wall of the depression in the faceplate 282 may be coated with a hydrophilic material. Similarly, the flexible diaphragm electrode 216 located inside the depression may likewise be coated with a hydrophilic material. The presence of the hydrophilic material within the depression may facilitate priming of the depression with aqueous humor. Examples of suitable hydrophilic materials include various oxides including silicon oxide, titanium oxide, tantalum oxide, various nitrides including silicon nitride, titanium nitride, tantalum nitride, various carbides including silicon carbide, titanium carbide, or other related materials. Such materials may be deposited as a thin layer using atomic layer deposition (ALD), physical vapor deposition (PVD) methods such as sputtering or evaporation, or chemical vapor deposition (CVD), among other methods. Other materials may be applied as a thin film to create a hydrophilic surface including biomaterials such as heparin, poly-L-lysine, or other materials. Alternatively and/or additionally, the hydrophilicity of the hydrophilic surfaces of the peripheral wall of the depression and/or the flexible diaphragm 216 may be increased by increasing the surface roughness using a variety of means such as dry or wet chemical etching or physical etching such as ion bombardment. Such roughening may be performed before, after, or in place of coating with a hydrophilic material. More generally, coatings may be provided to reduce leaking, reduce wear, and increase durability of physiological sensor 210.

In some embodiments, the depression in the faceplate 282 where the flexible diaphragm electrode 216 is located can be filled with a non-compressible, pressure-transmitting gel or other substance prior to insertion into the eye. The gel may displace air from the depression. Further, once the sensing implant 200 is surgically implanted, the gel may act as a pressure-transmitting medium which can allow pressure to be exerted on the capacitive pressure sensor 210 (located in the depression in the faceplate 282) by the aqueous humor in the eye. Examples of suitable materials for the non-compressible, pressure-transmitting gel include silicone gel, fluorosilicone gel, or other related materials.

Figures 7C, 7D, 7E:
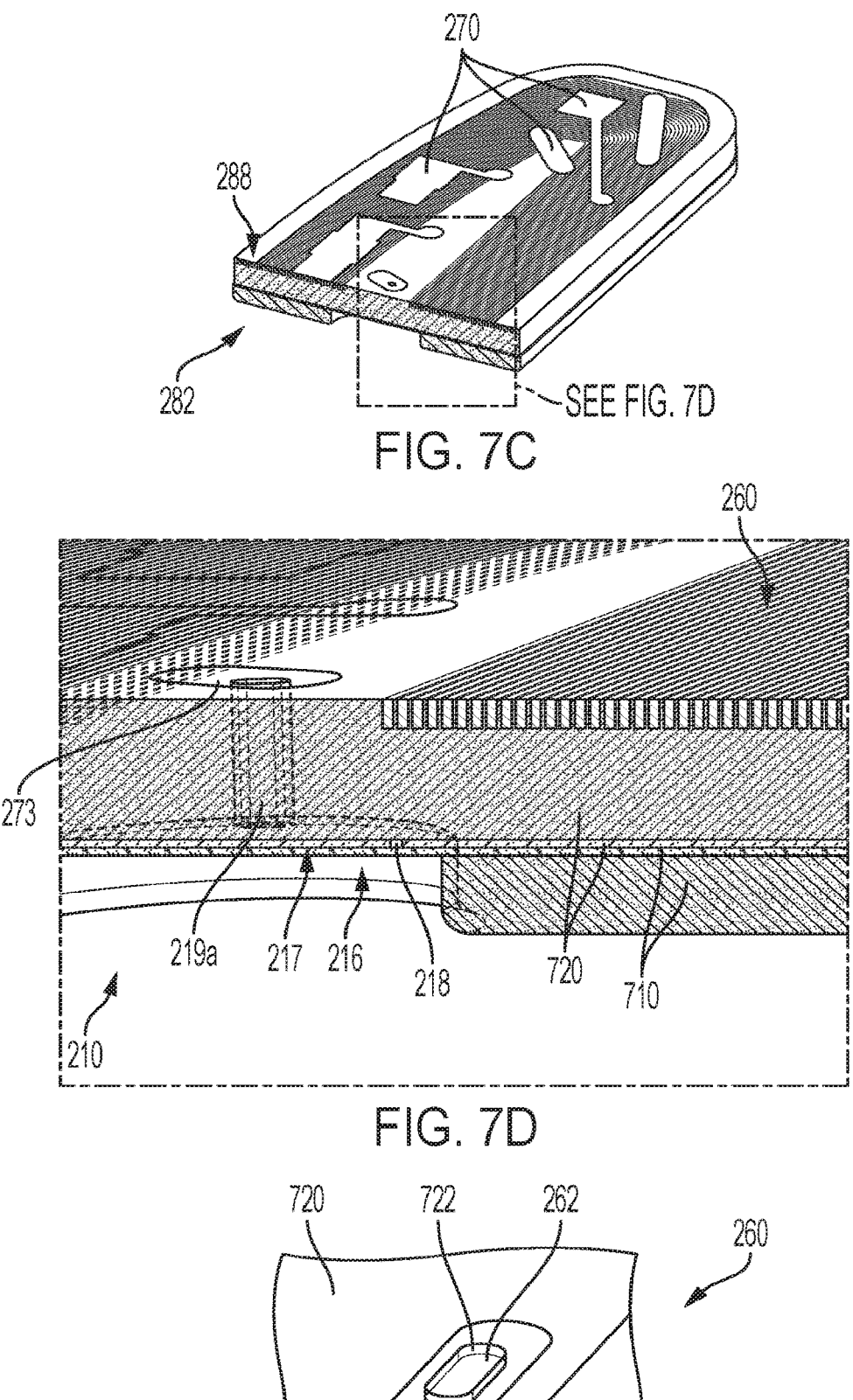
FIG. 7C illustrates a perspective view of a cross-section of a portion of the example faceplate for the housing of the intraocular physiological sensor implant shown in FIG. 7A.
FIGS. 7D-7E illustrate an example embodiment of how the coil inductor is connected to the electrical interconnect circuit of an intraocular physiological sensor implant.

FIG. 7C is a perspective view of a cross-section of a portion of the example faceplate 282 for the housing 280 of the intraocular physiological sensor implant 200 shown in FIG. 7A. The perspective view in FIG. 7C once again shows the flexible diaphragm electrode 216 and the counter electrode 217 of the capacitive pressure sensor 210. It also shows the isolation trench 218 formed around the counter electrode 217 to electrically isolate it from the flexible diaphragm electrode 216. In addition, the view in FIG. 7C shows a conductive via that is formed through the bulk silicon layer of the top substrate 720 in order to electrically connect the counter electrode 217 of the capacitive pressure sensor 210 to one of the conductive pads 273 (see FIG. 6A) of the electrical interconnect circuit 270. Although not shown in the illustrated cross-section, a second conductive via can be formed through the bulk silicon layer of the top substrate 720 in order to electrically connect the flexible diaphragm electrode 216 to the other conductive pad 273. Alternatively, substrates such as top substrate 720 can be any other metal or silica for forming the via. These conductive vias are used to route the capacitance signal from the capacitive pressure sensor 210 to the other components of the sensor implant 200.

FIGS. 7D-7E illustrate an example embodiment of how the coil 260 is electrically connected to the electrical interconnect circuit 270 of the intraocular physiological sensor implant 200. As already discussed, the coil 260 can be formed of a conductive material 262 which is embedded in a channel formed in the top of the bulk silicon layer of the top substrate 720. The channel can be a single continuous channel which spirals around the perimeter of the faceplate 282 to form a spiral of loops. Once the conductive material 262 has been deposited in the channels, an insulating layer 722 can be formed over the embedded conductive material 262. The insulating layer can be, for example, an oxide layer or a polymer layer. A hole can be left in the insulating layer 722 over each end of the coil 260. Conductive pads 274 (see FIG. 6A) which are part of the electrical interconnect circuit 270 can then be connected to the respective ends of the coil 260 through the insulating layer 722.

Figure 8A:
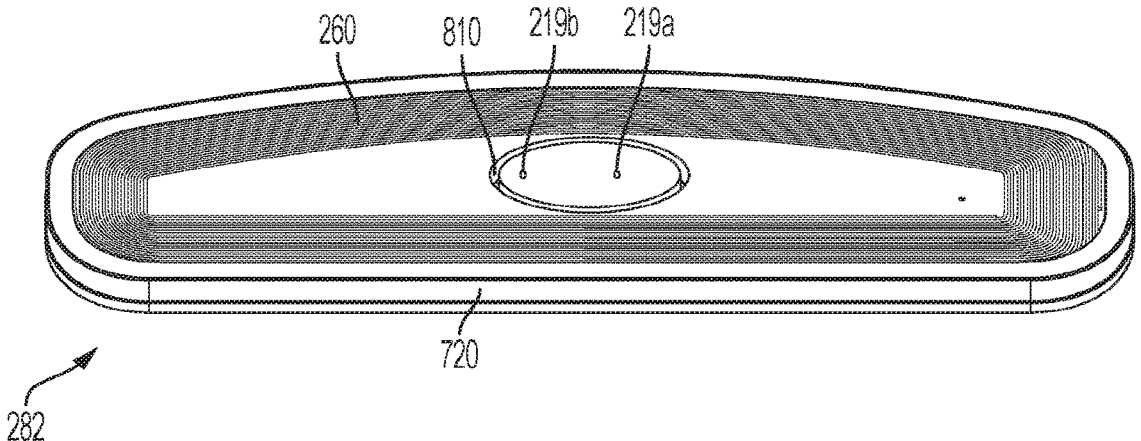
FIG. 8A illustrates a top perspective view of an example embodiment of an intraocular physiological sensor implant faceplate which includes a stress-relief cutout between the loops of an embedded coil and a physiological sensor.

FIG. 8A is a top perspective view of an example embodiment of an intraocular physiological sensor implant faceplate 282 which includes a stress-relief cutout 810 between the loops of the embedded coil 260 and the physiological sensor 210. In addition to the stress-relief cutout 810, FIG. 8A shows the embedded loops of the coil 260 and the conductive vias 219 which pass through the bulk silicon layer of the top substrate 720 from the two electrodes 216, 217 of the capacitive pressure sensor 210.

In embodiments where the coil 260 is embedded in the surface of the faceplate 282, there is a possibility that the embedded coil may affect the mechanical properties of the capacitive pressure sensor 210 which is integrated into the faceplate. For example, the conductive material, such as copper, which makes up the coil 260 is unlikely to have the same coefficient of thermal expansion as the material, such as silicon, which makes up the faceplate 282 and the capacitive pressure sensor 210. Thus, if the temperature of the sensor implant 200 changes after the coil material is deposited into the faceplate 282—for example when the sensor implant rises to body temperature after having been surgically implanted in the patient's eye—then the differing coefficients of thermal expansion of the two materials may cause mechanical stresses and strains to be introduced into the faceplate. Those mechanical stresses and strains have the potential to alter the behavior of the flexible diaphragm of the capacitive pressure sensor 210. This in turn may reduce the accuracy of the intraocular pressure measurements which are captured using the capacitive pressure sensor 210.

Temperature-induced mechanical stresses and strains in the faceplate 282 may be reduced by depositing the coil material into the faceplate in a manufacturing environment where the temperature is held at or near normal human body temperature. The faceplate 282 can also include a stress-relief cutout 810 to reduce the effect of any mechanical stresses and strains which may be induced by the embedded loops of the coil 260 either by temperature or by other means. The stress-relief cutout 810 can surround the capacitive pressure sensor 210 and can be located between the loops of the coil 260 and the capacitive pressure sensor 210.

Figure 8B:
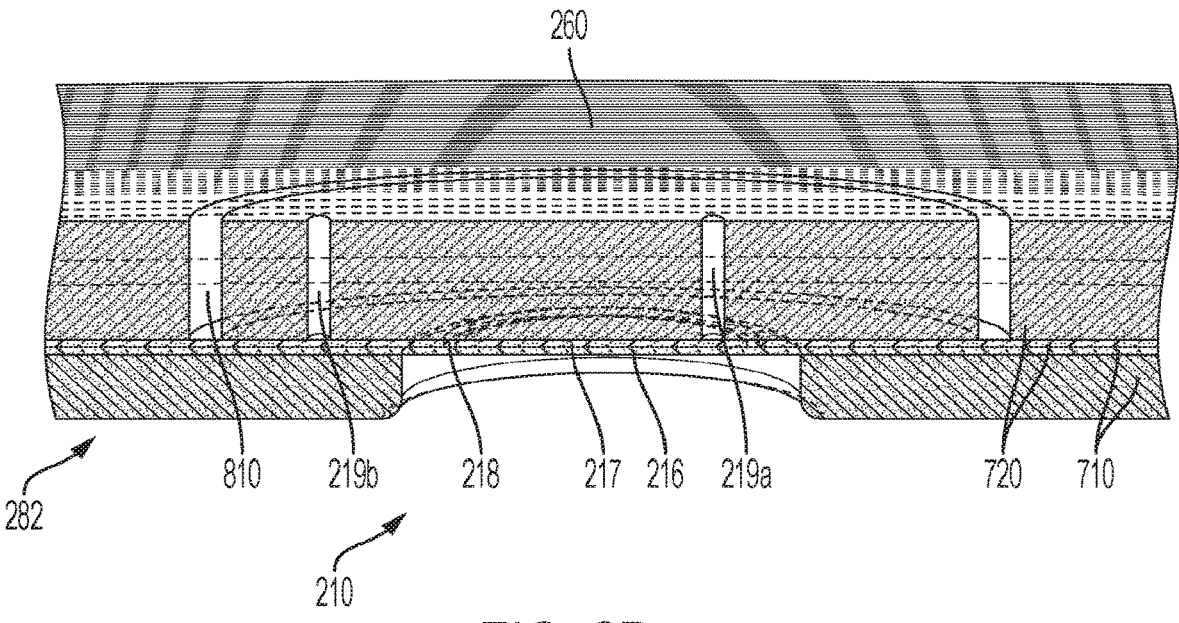
FIG. 8B illustrates a perspective view of a cross-section of the faceplate shown in FIG. 8A.

FIG. 8B is a perspective view of a cross-section of the faceplate 282 through the stress-relief cutout 810. FIG. 8B shows the bottom substrate 710 and the top substrate 720 of the faceplate 282. The loops of the coil 260 are shown embedded in the bulk silicon layer of the top substrate 720. FIG. 8B also shows the flexible diaphragm electrode 216 and the counter electrode 217 of the capacitive pressure sensor 210. A first conductive via 219a passes from the counter electrode 217 through the top substrate 720, while a second conductive via 219b passes from the high conductive silicon layers of the substrates 710, 720, which are extensions of, or contiguous with, the counter electrode 217 and the flexible diaphragm electrode 216, respectively, through the top substrate.

In the illustrated embodiment, the stress-relief cutout 810 is a channel through the bulk silicon layer of the top substrate 720 of the faceplate 282. In the illustrated embodiment, this channel completely surrounds the mechanically-active portion of the flexible diaphragm electrode 216 of the capacitive pressure sensor 210, while the loops of the coil 260 completely surround the stress-relief cutout 810. Thus, the stress-relief cutout 810 is located between the loops of the coil 260 and the mechanically-active portion of the flexible diaphragm electrode 216. The stress-relief cutout 810 helps to mechanically isolate the mechanically-active portion of the flexible diaphragm electrode 216 from the remainder of the faceplate 282. Mechanical stresses resulting from the embedded loops of the coil 216, whether they be induced by temperature changes or other means, therefore have a reduced impact on the mechanical properties of the flexible diaphragm electrode 216.

While the stress-relief cutout 810 is shown as passing through the entire thickness of the bulk silicon layer of the top substrate 720, in other embodiments the stress-relief cutout may only pass partially through the bulk silicon layer of the top substrate 720. Or, the stress-relief cutout 810 may pass completely through the top substrate 720 and partially through the bottom substrate 710. The stress-relief cutout 810 is illustrated as a circular or oval-shaped loop, but other shapes for the stress-relief cutout 810 are also possible. Further, in some embodiments, there may be multiple separate stress-relief cutouts 810 at different angular locations around the flexible diaphragm electrode 216. Some or all of these stress-relief cutouts may not necessarily completely surround the capacitive pressure sensor 210.

Figure 9A:
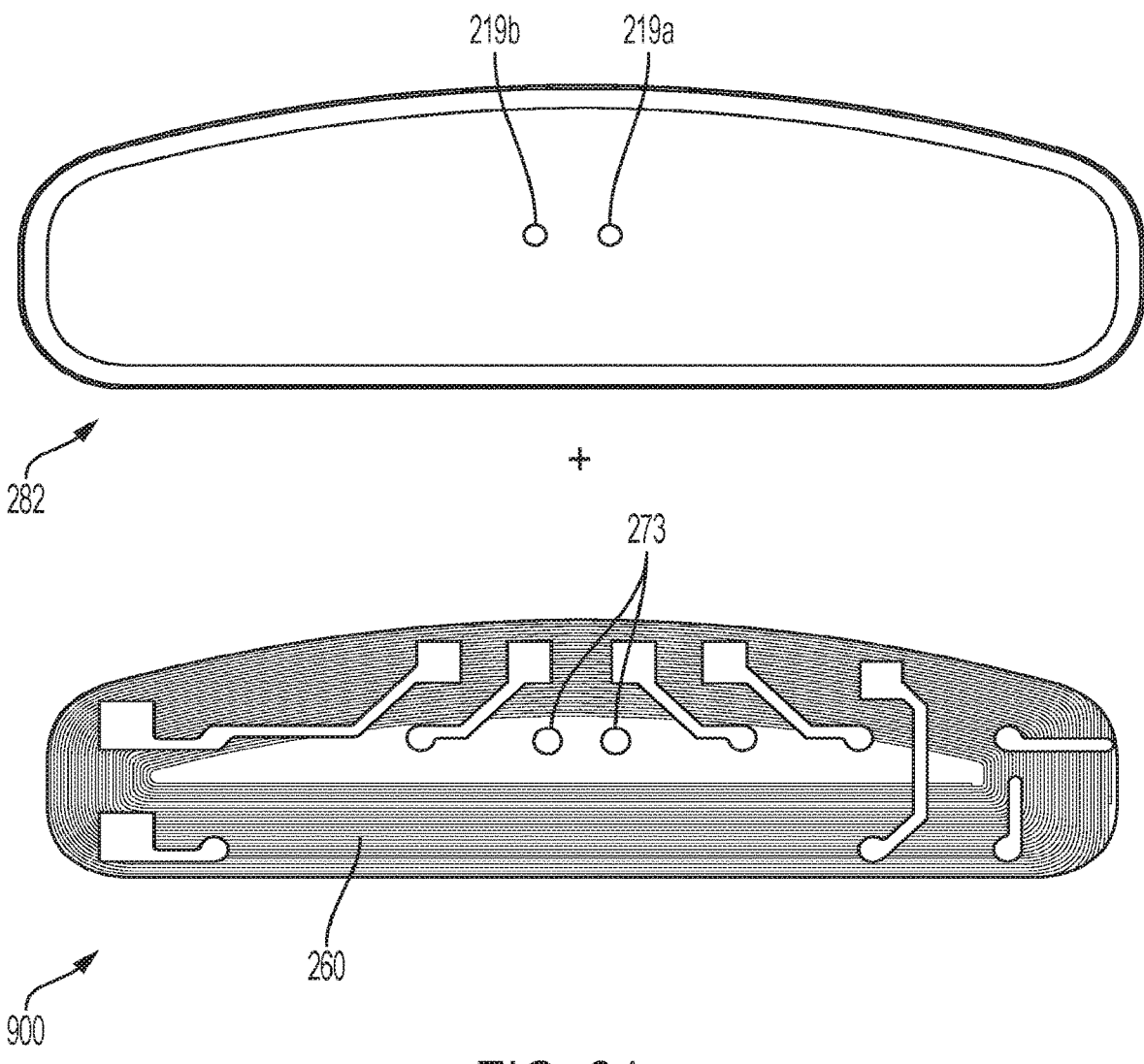
FIG. 9A illustrates an embodiment of a faceplate and circuit board for an intraocular physiological sensor implant.

FIG. 9A illustrates an embodiment of a faceplate 282 and circuit board 900 for the intraocular physiological sensor implant 200. Although the coil 260 and/or the electrical interconnect circuit 270 can be embedded in, or formed on, the interior surface of the faceplate 282, such as shown in FIGS. 5H-6D, this does not have to be the case in every embodiment. For example, as shown in FIG. 9A, the coil 260 and/or the electrical interconnect circuit 270 can be formed as one or more components which are separate from the faceplate 282. In the illustrated embodiment, the coil 260 and the electrical interconnect circuit 270 are provided on a circuit board 900. The circuit board 900 includes two electrical pads 273 which connect with the conductive vias 219 to the electrodes 216, 217 of the capacitive pressure sensor 210 when the circuit board is placed on the faceplate 282. Generally, circuit board 900 may be constructed from silicon, from polymer such as polyimide, or other materials such as glass or other polymers. Circuit board 900 may be several layers stacked together during fabrication, such as to create a multi-layer coil, multiple pieces with one or more turns of the coil each can be stacked together. For example three layers with two layers of coil each may be stacked to create a six layer coil. The top layer would have the circuit traces on its top side. Interconnects between each layer are necessary when stacking multiple pieces.

Figure 9B:
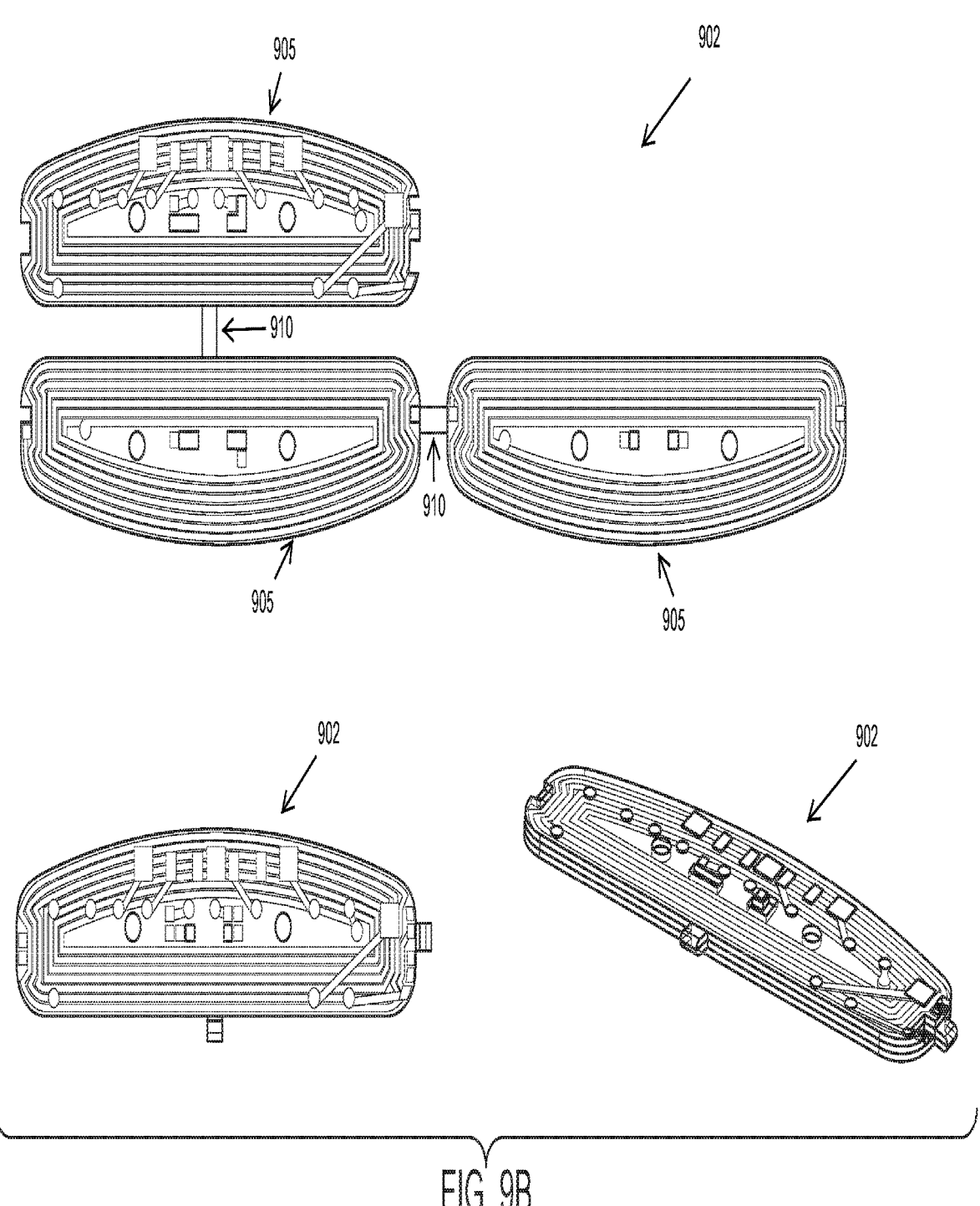
FIGS. 9B-9C illustrate top and perspective views of example embodiments of circuit boards in unfolded and folded configurations.
Figure 9C:
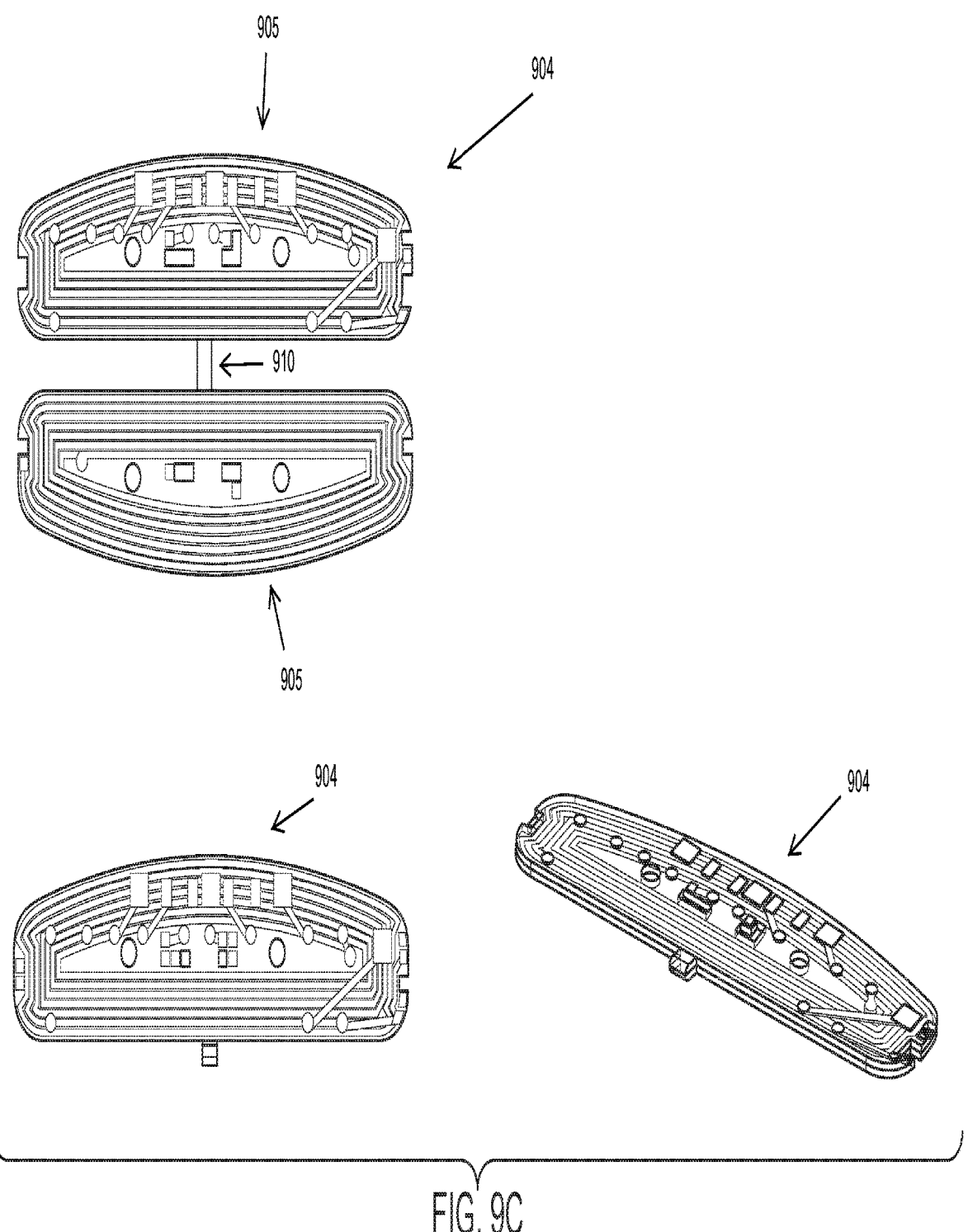

FIGS. 9B-9C show top and perspective views of example embodiments of circuit boards in unfolded and folded configurations, similar to circuit board 900. For example, FIG. 9B illustrates foldable circuit board 902. The illustrated embodiment of the circuit board 902 has a surface area that is preferably larger than the surface of the faceplate 282 where the circuit board is designed to be placed. The larger surface area of the circuit board 902 provides additional area for coil 260 than would be available in a non-folding design. For, example a configuration equivalent to a 4-layer coil can be constructed by folding two 2-layer coil sections 905 of circuit board 902 atop each other. Such a configuration would be useful, for example, to overcome manufacturing limitations in which a 4-layer monolithic coil would be impossible or cost-prohibitive to realize. The circuit board 902 also includes multiple flexible joint regions 910 which allow the various sections 905 of the circuit board 902 to fold up so as to fit in the footprint provided by the faceplate 282. In some embodiments, the sections 905 of the circuit board 902 which are connected by the joint regions 910 are also flexible such that the entire circuit board is flexible. In other embodiments, however, the sections 905 which are connected by the joint regions 910 may be rigid or comparatively rigid. For example, FIG. 9B illustrates that foldable circuit board 902 includes three sections 905, with two flexible joint regions 910. Similarly, for example, FIG. 9C illustrates that foldable circuit board 904 includes two sections 905, with one flexible joint region 910. It should be appreciated that more (or fewer) sections and/or flexible joint regions are contemplated herein.

Figure 9D:
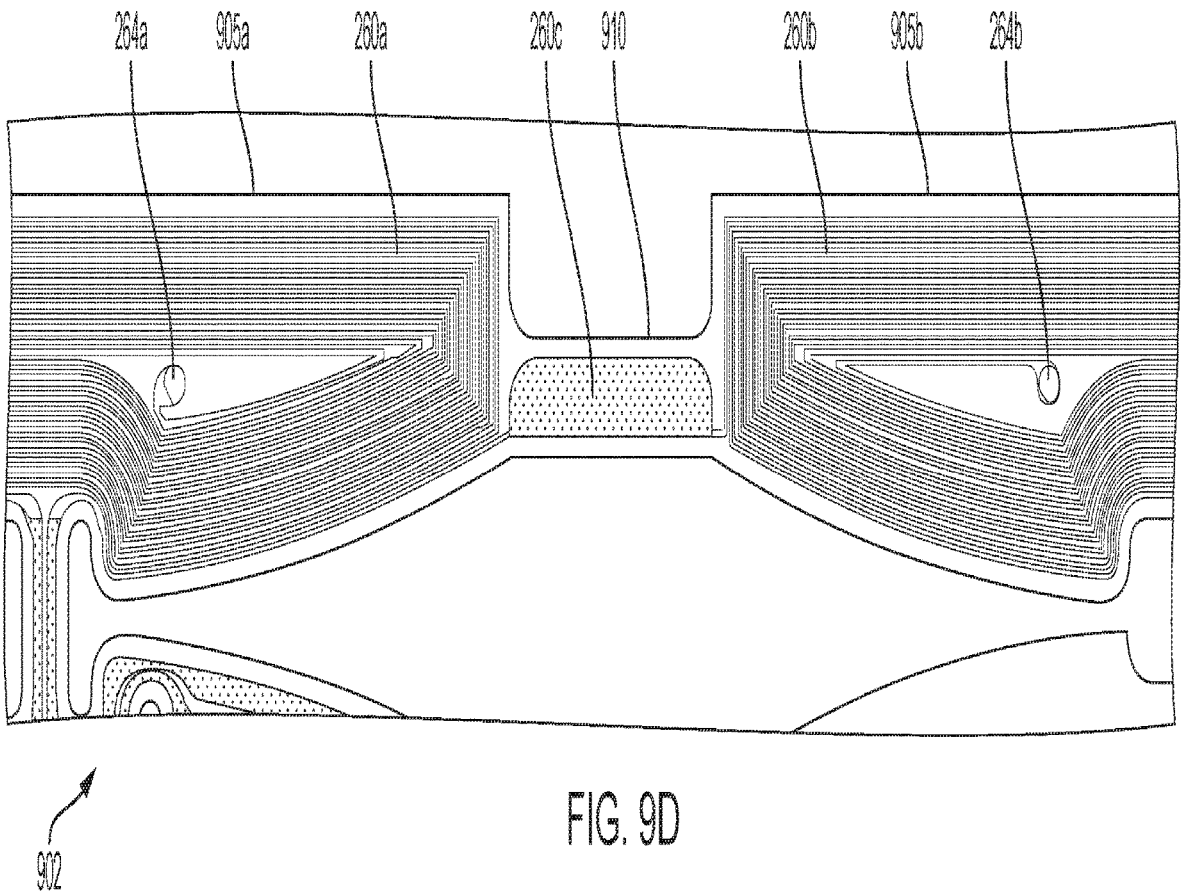
FIG. 9D illustrates an example embodiment of how a coil can be formed on multiple sections of the circuit board.

FIG. 9D illustrates an example embodiment of how the coil 260 can be formed on multiple sections 905 of a circuit board, such as the circuit board 902 illustrated in FIG. 9B. In some embodiments, the coil 260 is a conductive trace that is formed on a single section 905 of the circuit board 902. The conductive trace which makes up the coil 260 can be made by patterning a conductive material on a selected section 905 of the circuit board 902. The conductive material can be patterned onto the circuit board 902 in one or more layers. The width and height of the conductive trace can be specified so as to reduce the electrical resistance of the coil 260 to an acceptable amount.

The conductive trace can be laid out on a section 905 of the circuit board 902 to form multiple loops as a spiral of loops. By increasing the number of loops, the inductance of the coil 260 can be increased, which can also increase the sensitivity of the coil. The space available on a given section 905 of the circuit board 902 may limit the number of loops that can be formed, however. Scarcity of space for forming coil loops can be exacerbated if the manufacturing process used to deposit the conductive material is limited in terms of the height of the conductive trace which can be formed, thereby requiring the conductive trace to be made wider so that the electrical resistance of the trace is suitably low. This space limitation can be overcome, however, by patterning the conductive trace on multiple separate sections 905 of the circuit board 902 in such a manner that the coil loops formed on the separate sections 905 align with one another when the circuit board is in the folded configuration. The coil loops formed on the separate sections 905 of the circuit board 902 can also be laid out in a manner such that electrical currents through the conductive trace induce constructive, rather than destructive, magnetic fields at the coil loops patterned on the separate sections of the circuit board when the circuit board is in the folded configuration.

FIG. 9D shows a portion of first section 905a and a portion of second section 905b of the circuit board 902.

These two sections 905a, 905b are connected by a joint region 910. The conductive trace which forms the coil 260 is formed on both of the sections 905a, 905b of the circuit board 902 and on the joint region 910. A first end 264a of the conductive trace is shown in the first section 905a of the circuit board 902. The conductive trace spirals radially outward from the first end 264a in a counterclockwise direction around the first section 905a of the circuit board 902 so as to form a first set of coil loops 260a. A second end 264b of the conductive trace is shown in the second section 905b of the circuit board 902. The conductive trace spirals radially inward from the joint region 910 to the second end 264b in a clockwise direction around the second section 905b of the circuit board 902 so as to form a second set of coil loops 260b. Thus the rotational direction that current flows when following the path from first end 264a to second end 264b is opposite on the two sections 905a, 905b. The height and width of the conductive trace can be similar in both the first section 905a and the second section 905b of the circuit board 902.

In the illustrated embodiment, the middle portion 260c of the conductive trace is located in the joint region 910 of the circuit board 902. In some embodiments, the middle portion 260c of the conductive trace can be formed with a height that is less than the height of the conductive trace outside of the joint region 910 so as to improve the flexibility of the conductive trace in the joint region of the circuit board 902. If the width of the conductive trace were to remain constant, this reduced height would result in an increase in the electrical resistivity of the middle portion 260c of the conductive trace. In order to avoid, or lesson, this increase in electrical resistivity, the middle portion 260c of the conductive trace can also be formed with a width that is greater than the width of the conductive trace outside of the joint region 910, as illustrated in FIG. 9D.

An electrical current propagating through the conductive trace from the first end 264a of the coil 260 would travel through the first set of coil loops 260a spiraling around the first section 905a of the circuit board 902 in a counterclockwise direction. The electrical current would then pass through the middle portion 260c of the conductive trace, traversing the joint region 910 to the second section 905b of the circuit board 902. At the second section 905b of the circuit board 902, the electrical current would propagate through the second set of coil loops 260b in a clockwise direction towards the second end 264b of the conductive trace. In other words, due to the illustrated layout of the conductive trace, the direction of propagation of an electrical current through the second set of coil loops 260b is opposite of its direction of propagation through the first set of coil loops 260a when the circuit board 902 is in the unfolded configuration. Although both sets of coil loops 260a, 260b spiral radially outward in the same direction, such as counterclockwise, from the respective ends 264a, 264b of the conductive trace, electrical currents through the conductive trace propagate through one set of coil loops 260a from the corresponding end 264a towards the middle portion 260c, and through the second set of coil loops 260b from the middle portion 260c towards the corresponding end 264b.

With reference to FIG. 9D, when the circuit board 902 is in the unfolded configuration, the electrical current propagating from the first end 264a of the conductive trace through the first set of coil loops 260a would induce a magnetic field directed out of the page (when considering conventional current and the right hand rule). In contrast, the same electrical current propagating through the second set of coil loops 260b towards the second end 264b of the conductive trace would induce a magnetic field directed into the page. However, when the circuit board 902 is folded at the joint region 910 so as to place the first and second sections 264a, 264b in a stacked configuration, one directly over the other, the magnetic fields induced by the electrical current at the first and second sets of coil loops 260a, 260b will be aligned with one another in a consistent direction. Thus, when the circuit board 902 is in the folded configuration, the magnetic fields induced by an electrical current through the first and second sets of coil loops 260a, 260b are constructive rather than destructive.

The technique illustrated by the coil configuration shown in FIG. 9D can be used to increase the sensitivity of the coil 260 by allowing for a greater number of loops than can be formed on an individual section 905 of the circuit board 902.

Figure 9E:
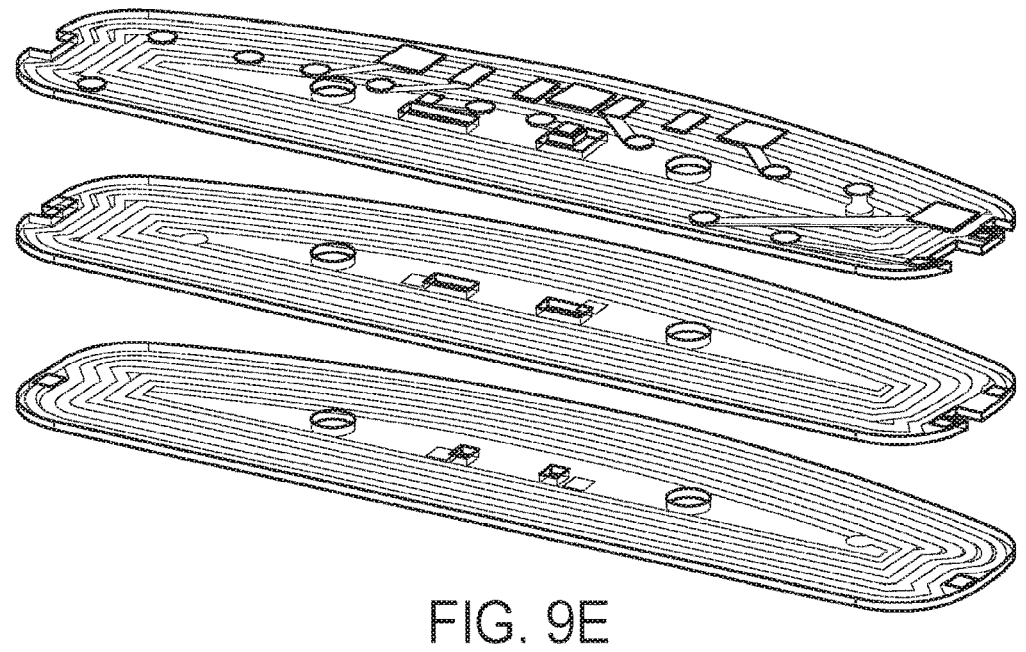
FIGS. 9E-9G illustrate top perspective views of a stacked circuit board.
Figure 9F:
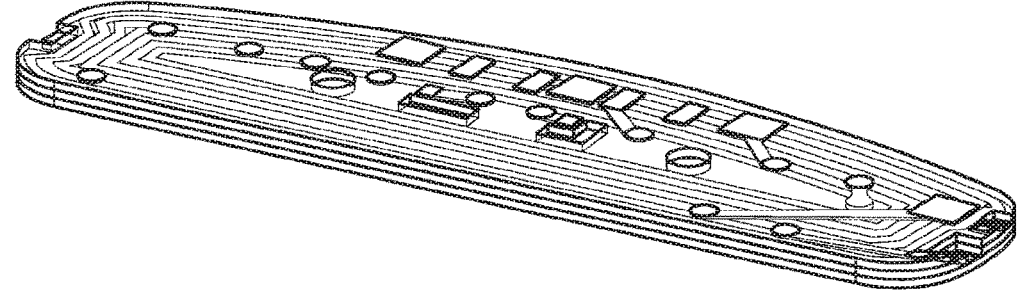
Figure 9G:
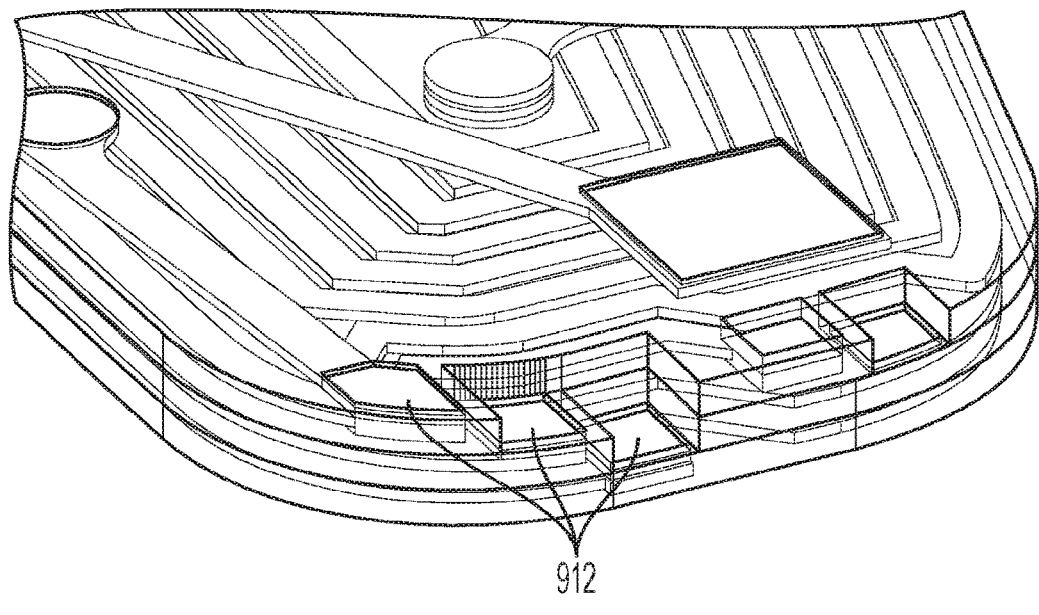

As an alternate to the folded circuit board 902, 904 illustrated by FIGS. 9B-9C above, circuit board 900 may alternatively be stacked. Specifically, FIGS. 9E-9G illustrate top perspective views of a stacked circuit board including top, middle, and lower levels in an exploded configuration (FIG. 9E) and a stacked configuration (FIG. 9F). Each of the top, middle, and lower levels are bonded together at individual pads 912, as illustrated by FIG. 9G. In an embodiment, these individual pads 912 are connected to one another via conductive epoxy beads.

Figures 10A, 10B:
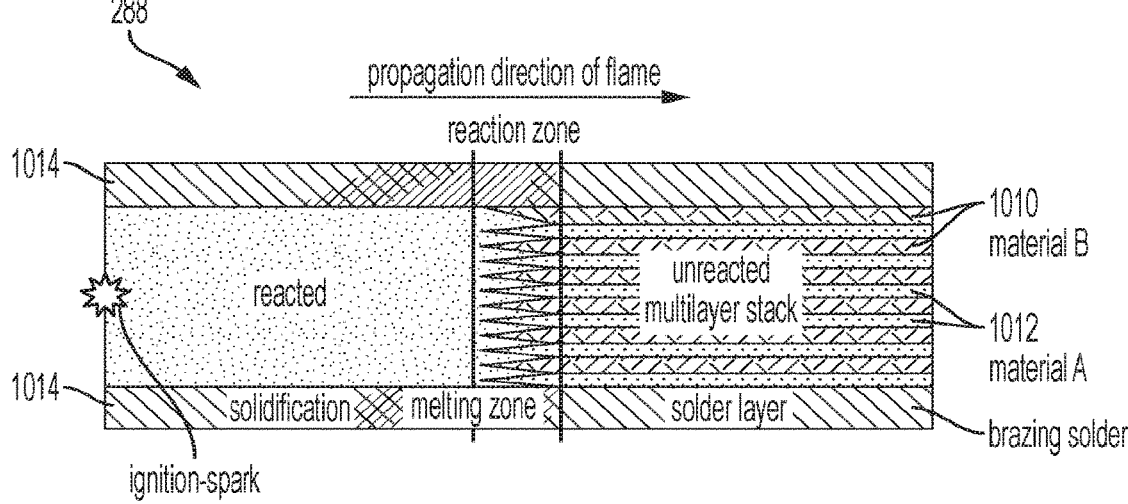
FIG. 10A illustrates a top view of an example embodiment of a hermetic seal between the components which make up the housing of an intraocular physiological sensor implant.
FIG. 10B illustrates a cross-sectional view of an example embodiment of the hermetic seal between the faceplate and the top cover of the housing for an intraocular physiological sensor implant.

FIG. 10A is a top view of an example embodiment of the hermetic seal 288 between the components which make up the housing 280 of the intraocular physiological sensor implant 200. As already discussed, the housing 280 can consist of a bottom faceplate 282 and a top cover 284. The hermetic seal 288 can be provided at the mating surface around the perimeter of these housing parts.

In some embodiments, the hermetic seal 288 is formed by welding, soldering, or brazing the faceplate 282 and the top cover 284 together at the mating surface. This can be accomplished by, for example, providing one or more layers of soldering material at the mating surface and using a heat source to melt the soldering material. The solder material may be a metal with a low melting temperature such as tin or indium or it may be a metal with a higher melting temperature such as gold or aluminum. The solder may alternatively be mixture or an alloy of two or more metals and have a lower melting temperature than that of any of the individual metals in their pure form such as a gold-tin solder, indium-tin solder, indium-silver solder, tin-silver-copper solder, or other related materials. The solder may be a eutectic system in which the ratio of the two or more metals in its composition is such that the melting temperature of the solder has a local minimum in melting temperature as compared to surrounding ratios of metals for that system such as gold-tin at an 80-20 percent-weight ratio. In some embodiments, the soldering material may be provided on the faceplate 282 or the top cover 284 or both components such that is integral to that components or it may also be provided as a separate preform component that is placed between the two pieces during assembly or it may also be dispensed at the seal location as a paste during assembly.

It may be advantageous to use a localized heat source to melt the soldering material so as to avoid thermal damage to the internal components of the sensor implant 200 while sealing the housing 280. In some embodiments, a reactive nanoscale multilayer stack can be used as the localized heat source in a process called reactive bonding. In some embodiments, an unmetallized glass housing is directly bonded to an unmetallized silicon faceplate using a laser welding or laser-assisted diffusion process. Additionally, a laser process can be employed with a solder or other metallization intermediate layer between the silicon faceplate and housing.

FIG. 10B is a cross-sectional view of an example embodiment of the hermetic seal 288 between the faceplate 282 and the top cover 284 of the housing 280 for the intraocular physiological sensor implant 200. The hermetic seal 288 can include, for example, top and/or bottom layers of soldering material 1014. The top layer of the soldering material 1014 can be applied or bonded to the mating surface of the top cover 284, while the bottom layer of the soldering material 1014 can be applied or bonded to the mating surface of the faceplate 282. A reactive nanoscale multilayer stack can be formed adjacent to the layer of soldering material 1014 on either the top cover 284 or the faceplate 282 such that when those two housing parts are joined the reactive nanoscale multilayer stack (RMS) is provided between the layers of soldering material 1014. Alternatively, the RMS may be provided directly on either the top cover 284 or the faceplate 282 without a soldering material. Alternatively, the RMS and/or the soldering material 1014 may be provided as a discrete preform component that is positioned between the top cover 284 and faceplate 282 during assembly. The reactive nanoscale multilayer stack can include alternating layers of a first material 1010, such as aluminum, and a second material 1012, such as nickel. Many other RMS systems with different metal combinations are possible such as Ti/Al, Pd/Al, Zr/Si, Pd/Sn/Pd/Al, or other related metal combinations. The number of layers may range from a few to several dozen to several hundreds and each layer may be on the order of a few nanometers thick. When energy from, for example, a laser is applied to the reactive nanoscale multilayer stack, a self-propagating, exothermic chemical reaction ensues. The chemical reaction results in inter-mixing between the alternating layers of the first material 1010 and the second material 1012. The heat produced by the reaction melts the soldering material, causing it to bond to the reacted nanoscale multilayer stack to form a localized metallic bond. This reaction propagates forward through the reactive nanoscale multilayer stack until traversing the entire perimeter of the housing 280. By implementing a reactive nanoscale multilayer stack, the heat generated is localized and very short in duration and therefore avoids undesirable temperature exposure to the battery or other temperature-sensitive components and also reduces bonding stress due to CTE mismatch between the top cover 284 and faceplate 282 because only the immediately-adjacent material surrounding the bond is heated during the bonding process.

Figure 10C:
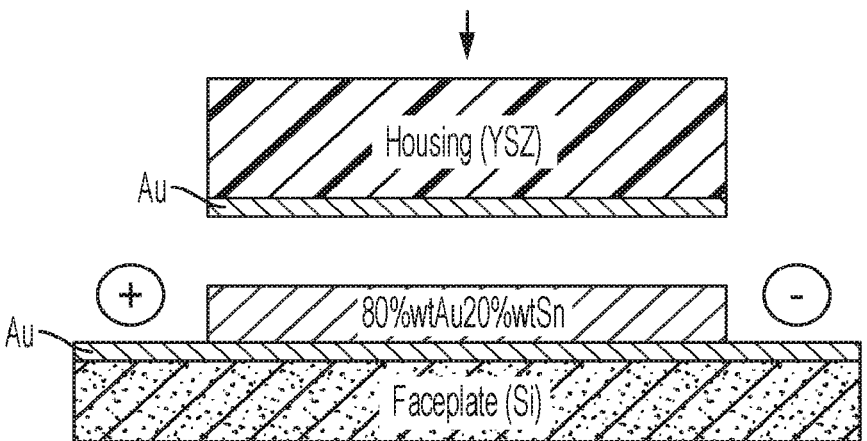
FIGS. 10C-10D illustrate hermetic sealing with a gold-tin sealing ring.
Figure 10D:
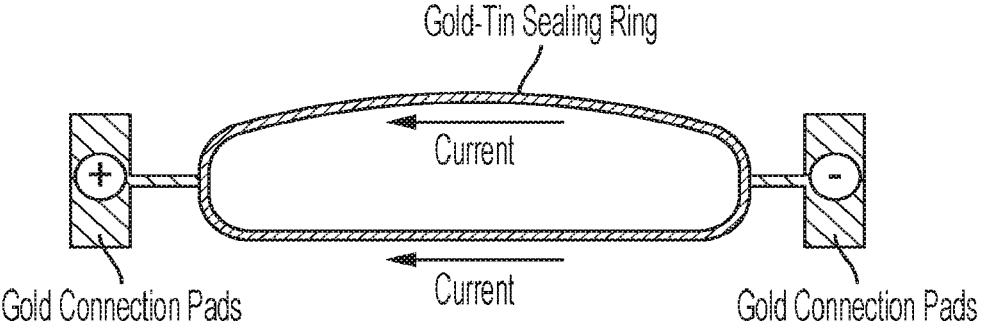

Because the battery 230 is temperature sensitive, as well as due to intrinsic stress caused by CTE mismatch between the top cover 284 and faceplate 282, a preferred bonding technique involves low-temperature bonding and/or localized heating to avoid undue heat exposure to the inner components of the sensor 280 and/or intrinsic stress in the final assembly. One preferred embodiment to enable low-temperature bonding includes a metallization on the periphery of the top cover 284 with gold, or gold and tin, or another metal, and likewise gold, or gold and tin, or another metal, on the faceplate 282. As an example, gold and tin is beneficial due to low creep and high rigidity. In various alternative embodiments, the soldering is achieved using methods of localized heat delivery, such as with a hot air gun or heat-conductive fixturing to provide heat quickly and melt the layers and effect a hermetic seal between the top cover 284 and the faceplate 282 without damaging internal components using a high-concentration of electricity or heat. In another embodiment, electrical current is run through a resistive material to generate heat sufficient to melt the layers as illustrated by FIGS. 10C-10D. For example, current may be passed through the seal itself, such that the seal acts as an autogeneous resistive heater and melts the solder. Contact is made on each end of the seal ring and voltage is applied such that current passes through the seal on both sides. Special care can be taken in locating the current entrance and exit locations to the seal ring to ensure that the current paths on each side of the seal ring are resistively symmetric such that heating is uniform on both sides. The seal material heats up, and the solder melts. In a specific example, AuSn solder would be put on the face plate and/or the housing; Au would be put on both components, such as the housing and the faceplate, so that the Au acts as a barrier on either side of the AuSn solder. Additional metal layers, such as Ti, Ta, Pt, W, or other can be included as additional barrier layers. The current can be run through either component, such as via gold connection pads illustrated in FIG. 10D. In these various embodiments, providing localized heat limits the total heat on the system, thus avoiding risk related to damaging sensitive components such as battery 230 by using a global heating method. It should be appreciated that other localized low-temperature bonding can accomplish this objective.

Figure 11:
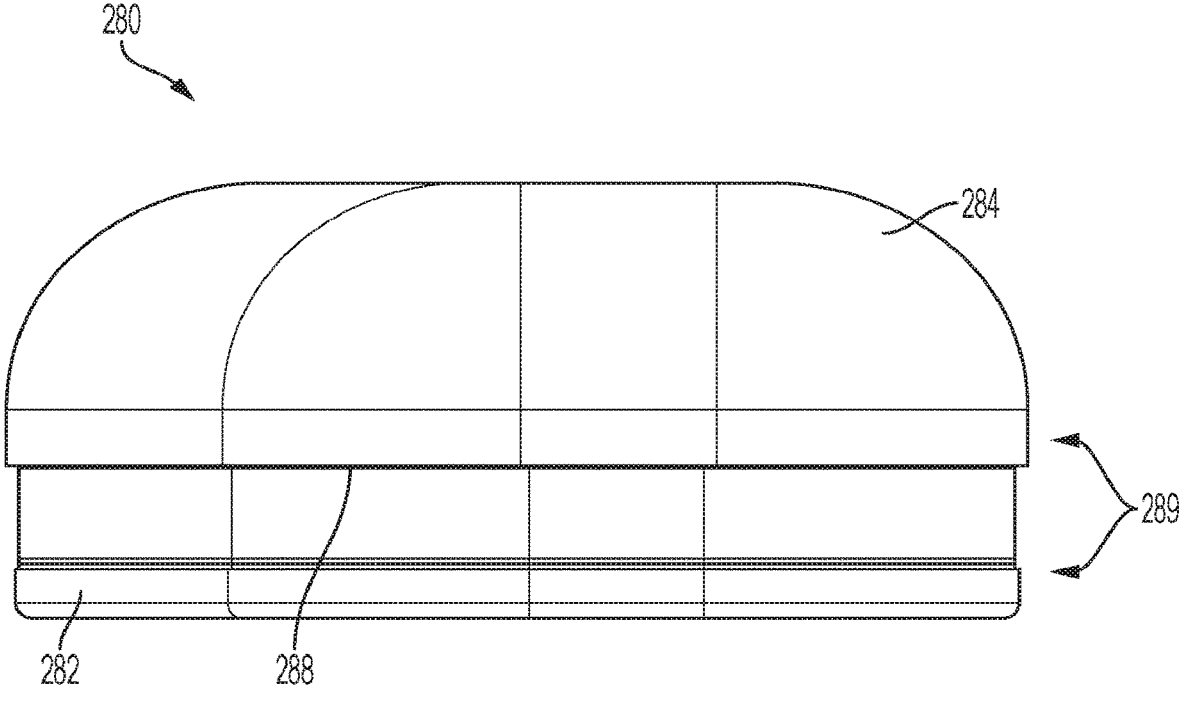
FIG. 11 illustrates an example embodiment of the faceplate and the top cover of the housing for an intraocular physiological sensor implant.

FIG. 11 illustrates example embodiments of the faceplate 282 and the top cover 284 of the housing 280 for the intraocular physiological sensor implant 200. In the illustrated embodiment, the top cover 284 includes a protruding lip 289 adjacent to the hermetic seal 288. The faceplate 282 can also include a protruding lip 289. The protruding lip of the faceplate 282 can be adjacent to the hermetic seal 288 or at some other location, such as near its bottom surface as illustrated. In some embodiments, the protruding lip 289 extends outwardly by at least 5 μm. The protruding lips 289 may be advantageous because they can help protect the hermetic seal 289 from being damaged by tweezers or other tools when the housing 280 of the sensor implant 200 is being handled before or during surgical implantation. For example, if tweezers are used to grasp the sides of the housing 280, then the tweezers will come in contact with the lip 289 rather than the hermetic seal 288. In an embodiment, the bottom of faceplate 282 includes a chamfer or rounded edge which may advantageously reduce the risk of injury that may be associated with sharper edge features; this is unique as Si is brittle and often difficult to manufacture with rounded features, like a chamfer.

In some embodiments, after the faceplate 282 and the top cover 284 have been sealed together, a thin-film coating can be applied to the entire housing 280 of the intraocular physiological sensor implant 200. The thin film can be, for example, titanium dioxide. The thin-film coating may be applied using atomic layer deposition (ALD) techniques. For example, the housing 280 can be alternately exposed to different gaseous precursor species. In an embodiment, thin-film ALD coating includes a multi-layer stack of different materials. For example, various layers in a multi-layer stack could include any of titanium oxide, titanium dioxide, aluminum oxide, aluminum dioxide, hafnium oxide, or other related oxides. In an embodiment, the multi-layer stack includes up to fifty layers. It should be appreciated, however, that more layers, fewer layers, and different materials are contemplated by the ALD coatings disclosed herein. Each of the separate precursor species can react with the surface of the housing 280 in a self-limiting manner such that the reaction terminates once all the reactive sites on the surface have been filled. The reaction of each precursor species can deposit a monolayer of atoms on the surface of the housing

280. By sequentially exposing the housing 280 to different precursor species, a perfect crystalline structure can be built up layer by layer.

The thin-film ALD coating may be a conformal layer of pinhole-free, crystalline titanium dioxide. An ALD coating such as this can provide several benefits. It can act as an additional hermetic seal to help prevent aqueous humor from penetrating the housing 280. By covering any exposed edges of the hermetic seal 288, the ALD coating can help prevent aqueous humor from reacting with metals from the metallic seal and dissolving them or reacting with them to produce corrosion, as well as prevent metals in the hermetic seal from leaching into the patient's eye.

In addition, the ALD coating can protect the housing 280 from dissolution in the aqueous humor over time if the materials used to make the housing are in any way water-soluble. As already discussed, some embodiments of the faceplate 282 and the flexible diaphragm 216 of the capacitive pressure sensor 210 are formed of silicon. This can be advantageous because there are many known manufacturing processes for creating microscopic structures out of silicon. However, uncoated silicon will dissolve in the body at a rate that can result in appreciable thinning during the lifetime of the sensor implant 200, such as 1-2 microns per decade. In some embodiments, the flexible diaphragm 216 may only be approximately 5 μm thick at the time of manufacture. Thus, dissolution of the flexible diaphragm 216 could result in a long-term thinning of the flexible diaphragm 216 which could materially alter its mechanical performance. This would require that the capacitive pressure sensor 210 be periodically re-calibrated. However, an ALD coating over the flexible diaphragm 216 could dramatically reduce the rate of dissolution or even prevent dissolution altogether, thereby helping to avoid the need for periodic re-calibration of the capacitive pressure sensor 210. The ALD coating itself can be applied in a low-stress manner, so its presence does not significantly affect the mechanical performance of the flexible diaphragm 216.

The ALD coating may be relatively soft and may therefore be susceptible to damage during surgical implantation of the sensor implant 200. Thus, the protective lips 289 shown in FIG. 11 can advantageously protect the coating over the hermetic seal 288. In addition, the fact that the flexible diaphragm 216 is located in a depression in the faceplate 282 (as discussed with respect to FIG. 7B) can advantageously protect the coating over the flexible diaphragm.

Wearables and Data Acquisition

In a preferred embodiment, sensor implant 200 autonomously records all data measured, via physiological sensor 210, and stores this data in measurement memory 240. Data may be recorded and stored at regular intervals, such as every fifteen minutes, so as to optimize power consumption from battery 230. Though recorded data is stored in measurement memory 240, this recorded data is occasionally transmitted to external reader devices for subsequent processing and analysis. For example, as previously noted, the transceiver/receiver 250 and the coil 260 may wirelessly transmit pressure measurements, stored in the measurement memory 240, to an external reader device such as a pair of eyeglasses that are worn by the patient. Eyeglasses may advantageously ensure that the external reader device for receiving pressure measurements, such as an antenna and/or coil on the eyeglasses, is located proximate to the sensor implant 200. In an embodiment, the eyeglasses communicate with the sensor implant 200 via inductive coupling.

Additionally, once pressure measurements are received at the eyeglasses, the eyeglasses may subsequently communicate these pressure measurements to additional external reader devices, such as a wearable wrist watch. In various embodiments, the eyeglasses communicate with the wearable wrist watch via Bluetooth, WiFi, Zigbee, or other related wireless communication. Beyond receiving pressure measurements and other data such as battery voltage, temperature measurements, and the like from the sensor implant 200 via the eyeglasses, the wearable wrist watch may communicate with the sensor implant 200 directly or with other physiological sensors and/or take physiological measurements directly. The wearable wrist watch may measure physiological parameters of the patient, such as heart rate, blood pressure, pulse oximetry, or the like. The wearable wrist watch may further measure environmental factors like barometric pressure, air temperature, and the like. The wearable wrist watch may associate these environmental factors with specific pressure measurements, for sensor calibration purposes or to identify data outliers. While the additional external reader device disclosed herein is a wearable wrist watch in one embodiment, it should be appreciated that other devices, such as bracelets, any other wearable electronic device, cell phones, tablets, e-readers, laptops, and the like are contemplated for communicating with the eyeglasses or with the sensor implant 200 directly. In an alternate embodiment, a hand-held reader device could also be used instead of glasses for communication. Generally, the glasses (or the hand-held reader) communicate directly to the implant via inductive link and the wearable device, such as the wristband, communicates to the glasses via Bluetooth. From the patient's point of view, however, it appears that the wristband is directly communicating with the implant. Thus, all patient interaction is done through the wristband, which may include a screen, UI capabilities, and the like. This configuration is beneficial because it only requires Bluetooth capability on the wristband. For example, the wristband does not require high power radiofrequency communication, coils, and the like; these features are included with the glasses.

Beyond data transmission, the eyeglasses are further configured to charge the physiological sensor 200. For example, the coil 260 may receive wireless power from the eyeglasses, via inductive coupling, to charge the battery 230, while the stored measurements are being downloaded at the eyeglasses. A wireless charging device can be integrated in the eyeglasses. The coil 260 can transmit measurement data and receive power for recharging the battery 230 either simultaneously, or one at a time (in either order). In some embodiments, the coil 260 includes multiple conductive loops which are oriented so that their axis is generally aligned with the optical axis of the eye. This orientation can allow for a relatively larger amount of electromagnetic flux to pass through the conductive loops after being transmitted from the eyeglasses.

Ideally, charging of physiological sensor 200 takes approximately thirty minutes, and is performed once a week. In various embodiments, the eyeglasses are configured to perform additional functions, beyond charging and data transmission. For example, the eyeglasses could include a fundus camera, such as along the rim of the glasses or as a clip-on or snap-in module that can be temporarily attached to the glasses, which photographs the patient's optic nerve during charging. These photographs, taken at regular intervals such as during the weekly charging of physiological sensor 200, are useful to the clinician to identify visual field loss. Because glaucoma effects the optic nerve and it is this specific region of the retina that is of most interest in monitoring the progression of glaucoma, and not the entire retina, it is possible to achieve fundus images appropriate for this purpose without necessarily dilating the pupil of the eye. Alternatively or additionally, the eyeglasses could include lights along the rim of the glasses or as a clip-on or snap-in module that can be temporarily attached to the glasses, which could perform peripheral vision testing for the patient. Peripheral vision testing generally includes a series of flashing lights located in various positions in the patient's field of view. This testing could be performed with such a pair of eyeglasses with integrated LEDs at various positions, or fiber optic light pipes to create spots of light visible to the patient in many locations, but sourced from an LED located elsewhere in the frame of the pair of eyeglasses. Similarly to fundus imaging, peripheral vision testing, taken at regular intervals such as during weekly charging, is useful to the clinician to identify rate of peripheral vision decay. Fundus imaging and peripheral vision testing is routinely performed infrequently for glaucoma patients and therefore an at-home testing system as described would provide orders of magnitude more data than is currently provided to the medical professional. This is especially important for visual field testing, which like IOP measurements, exhibits extreme amounts of variation, or noise, in typical patient data. The collection of more data, especially vastly more data than provided by the current standard of care, and subsequent averaging and trend analysis is an effective strategy for improving confidence in the analysis of data sets with inherently large variability.

As previously noted, data may be recorded and stored in measurement memory 240 at regular intervals. However, if the battery 230 runs out of power or becomes nonfunctional, the physiological sensor 200 can transition to on-demand mode. In on-demand mode, the physiological sensor 200 ceases to record measurements at intervals; however, the sensor 200 can be powered-up at any time, such as via eyeglasses charging explained above, so that live pressure measurements can be recorded and transmitted in an on-demand fashion. Specifically, for example, the user powers up physiological sensor 200 via the eyeglasses, which subsequently receive a live pressure measurement directly from physiological sensor 200. This live pressure measurement is then communicated from the eyeglasses to the wearable wrist watch as disclosed above.

Pressure Calibration

Figure 12A:
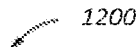
FIG. 12A illustrates a graph of the atmospheric pressure measured by a barometer worn by a user.
Figure 12A:
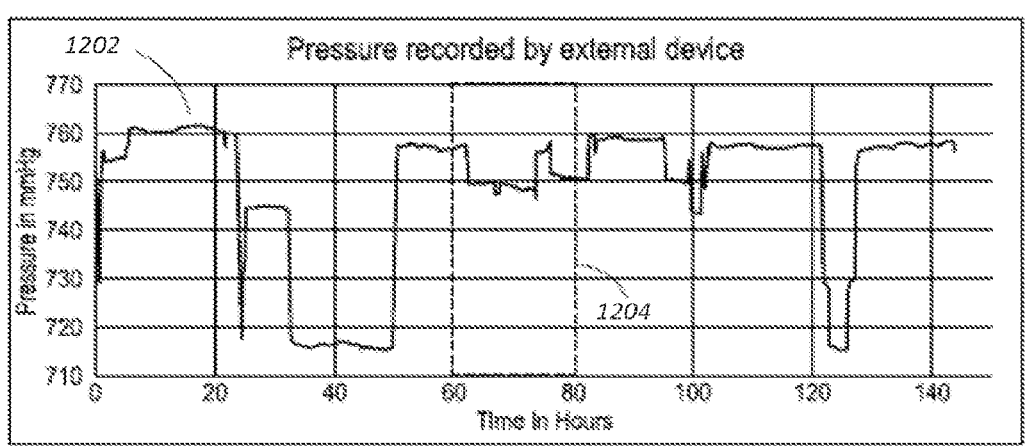
Figure 12B:
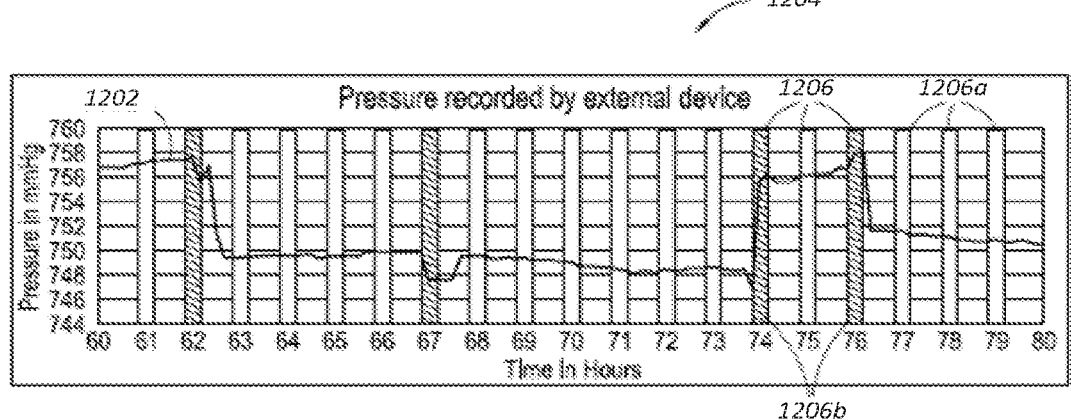
FIG. 12B illustrates a zoomed-in portion of the signal shown in FIG. 12A during the period of time from hour 60 until hour 80.

FIG. 12A is a graph 1200 of the atmospheric pressure measured by a barometer worn by a user. A signal 1202 shows the variation in atmospheric pressure over a period of about 140 hours. FIG. 12B shows a zoomed-in portion 1204 of the signal 1202 during the period of time from hour 60 until hour 80. During this period of time, the signal 1202 shows that the atmospheric pressure usually varied relatively slowly over time, most likely due to normal changes in weather conditions. An example of this kind of relatively slow weather-induced variation over time is shown by the signal 1202 from hour 69 until hour 73. However, the signal 1202 also shows that there were sudden, relatively large magnitude changes that also occurred. Examples of these types of sudden large changes in measured atmospheric pressure are seen in the signal 1202 approximately during hour 63 (i.e., between 62 and 63 on the graph), hour 68 (i.e., between 67 and 68 on the graph), hour 75 (i.e., between 74 and 75 on the graph), and hour 77 (i.e., between 76 and 77 on the graph). These sudden large changes in atmospheric pressure may have been the result of changes in altitude experienced by the user while he or she was driving up or down hills, moving between different floors of a building, and the like.

Because relatively large changes in atmospheric pressure such as these can occur over relatively short periods of time, care should be taken when correlating an atmospheric pressure measurement with an absolute IOP measurement for use in calculating a gauge IOP value: if the external and internal pressure measurements are offset from one another in time by too great a degree, there is a potential that the gauge IOP value derived from the two measurements may be significantly affected by one of these sudden, large magnitude changes in atmospheric pressure, thus reducing the accuracy of the gauge IOP value.

This difficulty in correlating internal absolute IOP measurements with external atmospheric pressure measurements can be exacerbated if there is some amount of drift over time in the accuracy of the respective timekeeping devices used by the external and implanted pressure measurement devices. For example, as shown in FIG. 2B, an IOP sensor implant may include a timekeeping device, such as a timer or a clock, which may be used to indicate the times at which pressure measurements are to be taken. Design constraints may favor or require the use of relatively simple timer or clock circuits. For example, cost, power consumption, and/ or circuit size constraints may favor or require the use of less advanced timers and/or clocks, such as ones which do not include a piezoelectric resonator, in implantable sensor devices. These timers and/or clocks may be less accurate than more advanced versions which would require, for example, larger numbers of circuit elements, a larger amount of space within the implantable sensor device, and/or more power. As a result, the timekeeping accuracy of the timers and/or clocks which may be used in implantable devices of the sort described herein may drift over time. In addition, these timekeeping devices may be more affected by temperature variations.

Even a timekeeping drift of just 0.1%, for example, can result in relatively large inaccuracies over periods of time such as days, weeks, or months. As a result, there may be a time offset between an atmospheric pressure measurement taken by an external device and an internal absolute IOP measurement taken by an implant within the patient's eye even though the respective timekeeping elements used by the two devices may indicate that the two measurements were taken concurrently. And, of course, a significant change in either the atmospheric pressure or the absolute IOP could occur during that time offset. If so, it would result in an inaccurate calculation of the gauge IOP value.

Figure 12C:
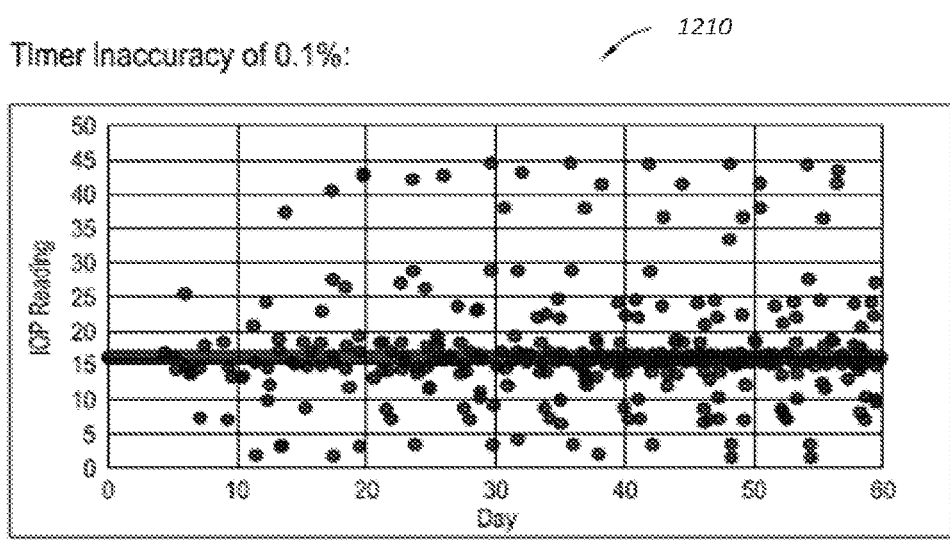
FIG. 12C illustrates the simulated effect of a timer inaccuracy of 0.1% which causes time offsets between absolute IOP measurements and atmospheric pressure measurements used to calculate gauge IOP values.
Figure 12D:
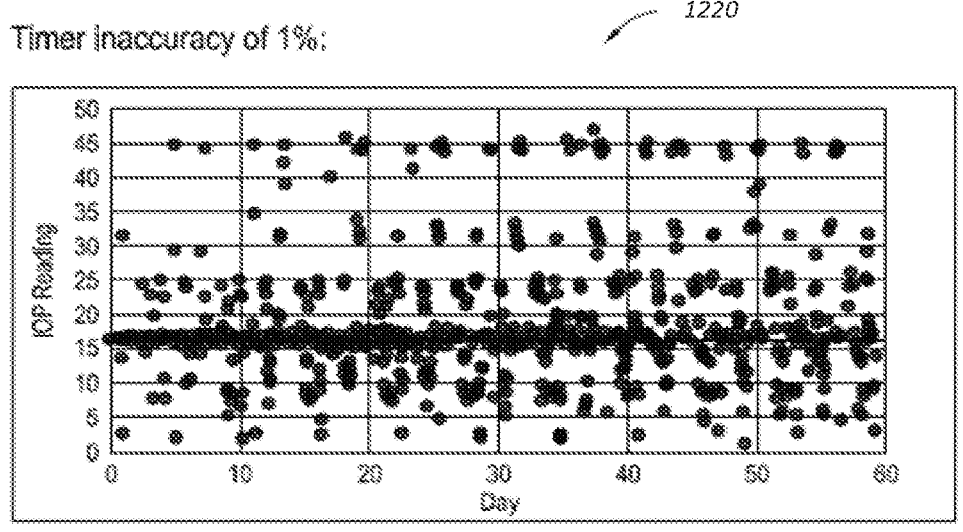
FIG. 12D illustrates the simulated effect of a timer inaccuracy of 1% which causes time offsets between absolute IOP measurements and atmospheric pressure measurements used to calculate gauge IOP values.
Figure 13A:
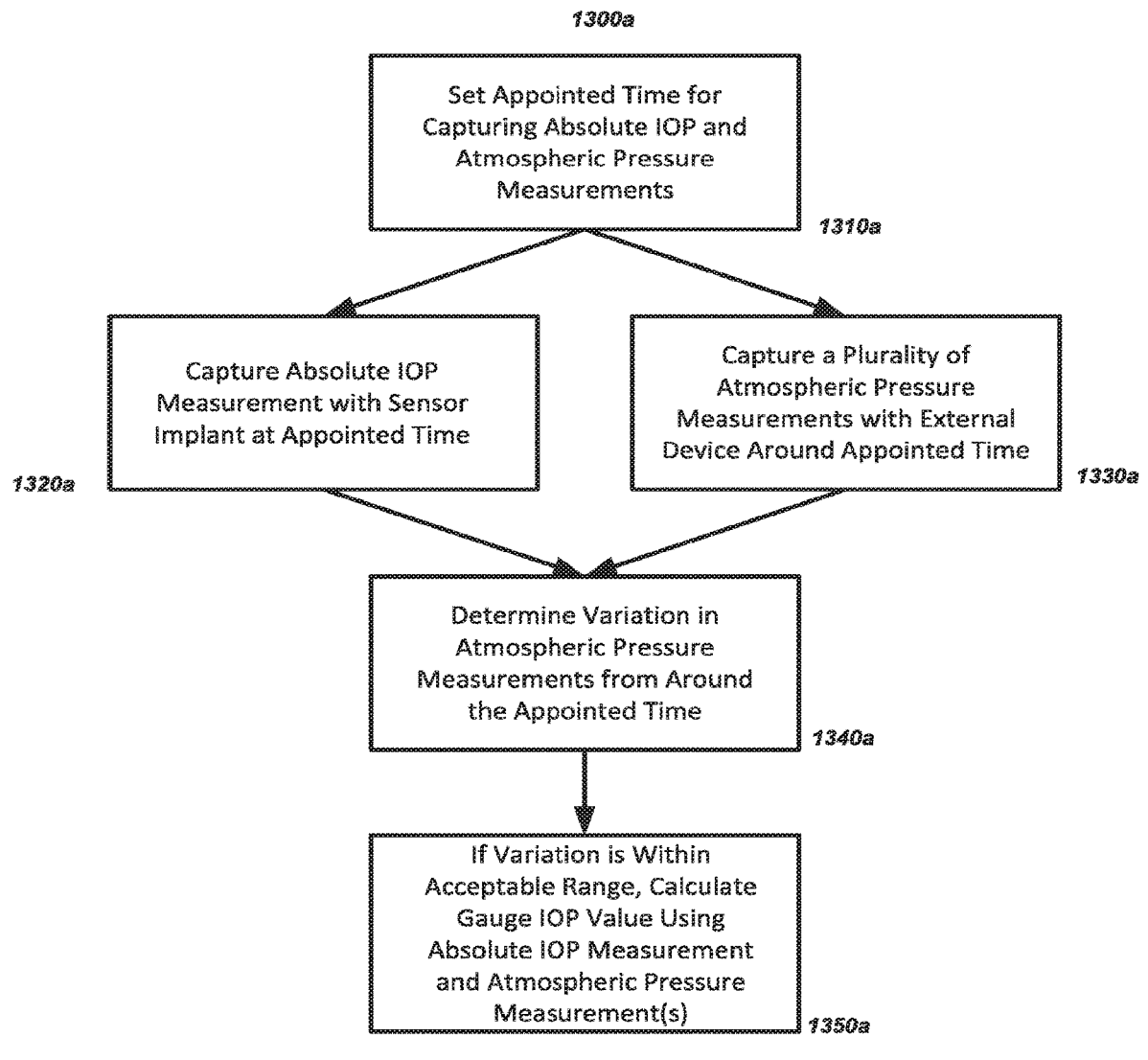
FIG. 13A illustrates an example method for calculating a gauge IOP value using one or more atmospheric pressure measurements from an external device and one or more absolute IOP measurements from a sensor implant within the patient's eye.

FIGS. 12C and 12D are graphs 1210, 1220, respectively, which illustrate examples of the inaccuracies in calculated gauge IOP values which may result from time offsets between absolute IOP measurements and atmospheric pressure measurements. FIG. 12C illustrates the simulated effect of a timer inaccuracy of 0.1%, while FIG. 12D illustrates the simulated effect of a timer inaccuracy of 1%. In both graphs 1210, 1220, the plotted gauge IOP values were calculated by subtracting atmospheric pressure values from absolute IOP values at regular intervals, such as every hour. In these simulated examples, the absolute IOP signal and the atmospheric pressure signal were designed to result in a constant gauge IOP signal of 16 mmHg. That is, although the absolute IOP signal and the atmospheric pressure signal both varied in time similarly to what is shown in FIGS. 12A and 12B, the difference between these signals—gauge IOP—was designed to be constant. If the gauge IOP values had been calculated using absolute IOP values and atmospheric pressure values that were perfectly synchronized in time, then the plotted gauge IOP values would have remained constant at 16 mmHg. However, in these simulations, time drift was introduced between the atmospheric pressure values and the respective absolute IOP values used to calculate the gauge IOP values. As shown in the graphs 1210, 1220, within just a few days or less, the simulated timer inaccuracies resulted in a lack of synchronization between the respective absolute IOP values and atmospheric pressure values, which in turn caused large, false variations in the calculated gauge IOP values. FIGS. 13A and 13B illustrate example methods for avoiding these types of inaccuracies.

FIG. 13A illustrates an example method 1300a for calculating a gauge IOP value using one or more atmospheric pressure measurements from an external device and one or more absolute IOP measurements from a sensor implant within the patient's eye. The method begins at block 1310a where the appointed times and/or intervals are set for capturing absolute IOP measurements, using a sensor implant in the patient's eye, and atmospheric pressure measurements, using an external device. For example, both the external device and the implanted sensor device can be set (e.g., using onboard software, firmware, and/or hardware) so as to capture measurements at, or around, times $T_1$, $T_2$, $T_3$, . . . , and the like. These times may be independently measured by the external device and the sensor implant using, for example, their respective onboard timekeeping devices.

As already discussed, even though the respective timekeeping devices used by the external device and the sensor implant may be initially synchronized, timekeeping drift may cause them to gain or lose time with respect to one another, thus losing synchronization. As a result, the sensor implant may actually capture absolute IOP measurements at times $T_1 \pm \Delta_1$, $T_2 \pm \Delta_2$, $T_3 \pm \Delta_3$, and the like. Similarly, the external device may actually capture atmospheric pressure measurements at times $T_1 \pm \delta_1$, $T_2 \pm \delta_2$, $T_3 \pm \delta_3$, and the like, where $\Delta_n$ and $\delta_n$ may be different and unknown. Additionally, or alternatively, both the external device and the sensor implant can be set so as to capture measurements at, or around, intervals $I_1$, $I_2$, $I_3$ . . . But, once again, there may be unknown offsets between the instants in time when the external atmospheric pressure measurements and the absolute TOP measurements are actually captured.

At block 1320a, the sensor implant captures an absolute TOP measurement within the patient's eye at the appointed time/interval (e.g., $T_1$, $I_1$). This measurement may be stored in an onboard memory or transmitted to an external reader device. At least partially concurrently, at block 1330a, the external device captures a plurality of measurements during a window of time that may extend before and/or after the appointed time/interval (e.g., $T_1$, $I_1$). The length of the atmospheric pressure measurement window can be determined based on, for example, the timekeeping drift that is present in the sensor implant timekeeping device and/or the timekeeping device used by the external device which measures atmospheric pressure. The amount of timekeeping drift can specify an uncertainty window around each appointed measurement time during which a measurement may occur. In some embodiments, the atmospheric pressure measurement window can be set to be at least as large as this timekeeping uncertainty window. For example, in some embodiments the external device captures a plurality of measurements during a 20 minute window of time centered on the appointed time/interval. These atmospheric pressure measurement windows are indicated in FIG. 12B by the bars 1206 which are centered at each hour on the hour. The number of atmospheric pressure measurements captured during each atmospheric pressure measurement window can be selected based on, for example, the length of the window of time, the desired sampling rate, the available memory, or other selection means. During the window of time, atmospheric pressure measurements may be captured, for example, every second, every 10 seconds, every minute, or other time frequencies.

At block 1340*a*, the measurements captured during the atmospheric pressure measurement window of time can be analyzed to determine the amount of variation that is present in the measurements. For example, the atmospheric pressure measurements can be analyzed to determine whether, during the window around the appointed measurement time/interval, the variation between the atmospheric pressure measurement values stays within a selected range (e.g., variation ≤10 mmHg, ≤5 mmHg, ≤1 mmHg, ≤10%, ≤1%) The calculation of the variation in the atmospheric pressure signal can be done according to any appropriate mathematical technique, including calculation of one or more differences, calculation of a variance or standard deviation, or other related techniques. This analysis can be performed by, for example, the external measurement device. Alternatively, the analysis can be performed by a separate processing device to which the atmospheric pressure measurements are uploaded. In FIG. 12B, the unshaded bars 1206*a* are examples of ones where the amount of variation in the measurements captured during an atmospheric pressure measurement window was within a selected acceptable range, while the shaded bars 1206*b* are examples of ones where the amount of variation was found to be outside the selected acceptable range.

At block 1350*a*, if the variation in the atmospheric pressure measurements captured during the window of time is acceptable, then one or more of the atmospheric pressure measurements within the window can be accepted and used, together with the absolute IOP measurement captured at the appointed time/interval using the sensor implant, to calculate a gauge TOP value. For example, the atmospheric pressure measurement which is nearest in time to the appointed time/interval may be selected for use in the calculation of the gauge TOP value. Or the average of all measurements during the atmospheric pressure measurement window may be used. Or a representative atmospheric pressure value can be computed or selected from all the measurements in the atmospheric pressure measurement window in some other way. However, in these embodiments, an atmospheric pressure measurement is only accepted for use in calculating a gauge TOP value if the atmospheric pressure data are relatively stable (within prescribed limits which can be set based on the application or the desired accuracy) over the course of the atmospheric pressure measurement window. In this way, a gauge TOP value is only calculated for times when it is relatively certain that the calculated value will not be substantially negatively impacted by variations in atmospheric pressure experienced by the user during the atmospheric pressure measurement window. Alternatively, the gauge TOP value could be calculated in all cases and then only stored and/or presented to the user if the foregoing criterion is met. Or a suspect gauge TOP value (e.g., one calculated using data captured during a period of time when variation in atmospheric pressure exceeded some set threshold) can be presented to the user with a flag or notification that it is a suspect value. The calculation of a gauge TOP value according to block 1350*a* can be performed by, for example, an external device to which atmospheric pressure measurements and TOP measurements are both uploaded.

FIG. 13B illustrates an example method 1300*b* for correlating an atmospheric pressure measurement from an external device with an absolute IOP measurement from a sensor implant for purposes of determining a gauge IOP value. The method 1300*b* begins at block 1310*b*, where an external device or system which is used to capture atmospheric pressure measurements initiates a synchronization operation by wirelessly transmitting synchronization information to the sensor implant within the patient's eye. The synchronization information can be, for example, a value, such as a timestamp or a unique correlation ID number, which is associated with a particular time (e.g., the current time when the synchronization signal is transmitted), as indicated by the timekeeping device used by the external device to determine when to capture atmospheric pressure measurements. In some embodiments, the synchronization information may be wirelessly transmitted at a different frequency than that which is used to send wireless power to the implant and/or to download data from the implant. The synchronization information can be stored by the external device in association with the time of the synchronization operation, as indicated by its onboard clock or timer. The synchronization information can be stored together with the measurements of atmospheric pressure, which may also be stored in association with the times when they were captured, as indicated by the onboard clock or timer.

In some embodiments, the synchronization information is transmitted by the external device at predetermined times and/or intervals. In some cases, the user may be prompted to interact with the external device so as to initiate a synchronization operation. In some embodiments, the external device used to capture atmospheric pressure measurements may be an article designed to be worn on the wrist like a watch. The external device may output an audible alarm or other prompt to remind the user to perform a synchronization operation. The synchronization operation may require the user to bring the external device in proximity to his or her eye so as to allow the sensor implant to more readily receive the synchronization information. In some embodiments the external device may transmit the synchronization information using a transmission power sufficiently high so that the user is not required to bring the external device in proximity to his or her eye. In such embodiments the external device may be located on the body of the patient, for example on the wrist of the user or hung from neck of the user, or even nearby the user such as in the same room, and it may not be required that the user bring the external device into close proximity to his or her eye.

At block 1320*b*, the sensor implant receives the synchronization information and associates it with the current time, as indicated by its onboard timekeeping device (e.g., clock or timer). The sensor implant can then store the synchronization information along with the associated time of the synchronization operation. The synchronization information can be stored together with the measurements of absolute IOP, which may also be stored in association with the times when they were captured, as indicated by the onboard timekeeping device of the sensor implant.

Then, at block 1330*b* the sensor implant captures an absolute IOP measurement within the patient's eye at the appointed measurement time/interval. At least partially concurrently, at block 1340*b*, the external device captures one or more atmospheric pressure measurements at and/or around the appointed measurement time (e.g., as discussed with respect to FIG. 13A).

After absolute IOP and atmospheric pressure measurements have been captured, they can both be uploaded, together with the synchronization information respectively stored by the two devices, to a processing device. The processing device can then, at block 1350*b*, correlate one or more absolute IOP measurements with one or more atmospheric pressure measurements based on the synchronization information. As already mentioned, the synchronization information received from the atmospheric pressure measurement device is associated with the time indicated by its timekeeping device when the synchronization operation was performed. Similarly, the synchronization information received from the sensor implant is associated with the time indicated by its timekeeping device when the synchronization operation was performed. Thus, the synchronization information can be used to identify one or more atmospheric pressure measurements which were taken at, or approximately at, the same time as an absolute IOP measurement from the sensor implant (e.g., within minutes or, more preferably, within seconds of each other). Then, at block 1360*b*, the processing device can calculate a gauge IOP value using the correlated absolute IOP measurements and atmospheric pressure measurements. In other embodiments, the implant need not necessarily include a timekeeping device but may instead rely on receiving a wireless signal from an external device to initiate an IOP measurement. The external device could perform an atmospheric pressure measurement at or near the time when the wireless signal is transmitted (e.g., within 1 s, or within 10 s, or within 60 s).

In some embodiments, absolute IOP measurements can be correlated with respective concurrent atmospheric pressure measurements by using signal processing techniques, such as pattern correlation. For example, both a signal made up of absolute IOP measurements taken over time and a signal made up of atmospheric pressure measurements taken over an at least partially overlapping period of time can be analyzed according to known signal processing techniques (e.g., autocorrelation, feature extraction algorithms, or other processing techniques) to identify signal features, such as peaks, patterns, ad the like. If matching features are identified in both signals, then one of the signals can be shifted in time with respect to the other (e.g., by the time offset between matching features) so as to correlate absolute IOP measurements and atmospheric pressure measurements which were taken concurrently. These concurrent measurements can then be used to calculate gauge IOP values. This method could be applied in addition to other synchronizing methods (e.g., as discussed with respect to FIGS. 13A and 13B).

In some embodiments, an external device, such as the one used to measure atmospheric pressure, can emit a control signal to an IOP sensing implant which causes the implant to capture an absolute IOP measurement. The external device can capture an atmospheric pressure measurement substantially concurrently with the control signal such that the absolute IOP measurement and the atmospheric pressure measurement are taken sufficiently concurrently to avoid substantial inaccuracies in the calculation of gauge IOP values. In some such embodiments, the external device can prompt the user to initiate absolute IOP and atmospheric pressure measurements at appointed times. For example, the external device may provide an indicator such as an alarm to remind the user to initiate the measurements at an appointed time. In order to initiate the measurements, the user may, for example, actuate a button, switch, or other feature on the external device. This action may 1) initiate an atmospheric pressure measurement; and 2) initiate the control signal from the external device to the implanted IOP sensing implant. As just discussed, this control signal may be used to cause the IOP sensing implant to capture an absolute IOP measurement. In such embodiments, the control signal may include, or consist of, a unique correlation ID number, or other uniquely identifying characteristic as described previously herein, which would enable the measurements of the IOP sensing implant and the external device to be correctly correlated even in the case that a control signal was not properly received by the IOP sensing implant. The external device may be provided in a kit with information which indicates that the user should bring the external device in proximity to his or her eye when performing this operation so as to improve communication of the control signal to the IOP sensing implant.

In some embodiments, the IOP sensing implant may include a low power clock—which may be relatively inaccurate—to initiate a ready state in which the implant can receive a signal from an external device. For example, the low power clock may cause the implant to enter this ready state for a window of time during which a signal such as those described herein (e.g., synchronization signal, control signal, or the like) is expected to be received from an external device. This period may be, for example, a 1, 5, 10, 30, or 60 minute window about the time when a signal is expected from the external device. This scheme may be beneficial because it may allow for the use of radio signals rather than signals sent via inductive coupling. While radio signals can travel further, they may lack the power needed to wake up the implant from a sleep state. For radio signals to be used, typically the TOP sensing implant needs to have a radio circuit powered on and ready to receive the signal. It can be advantageous, though, to use the low-power clock to shut down the radio circuit except during the ready period when a signal is expected from the external device. In some embodiments, the low power clock can be synched to the correct time at various intervals by an external device (e.g., during a charging or data download interaction).

Power Supplies

The various TOP sensing implants described herein can include one or more power supply devices to provide operating power for the various components of the TOP sensing implants. In some embodiments, an TOP sensing implant can include two separate power supply devices of different types. A first power supply device can be, for example, a battery, while a second power supply device can be, for example, a capacitor or supercapacitor. These separate power supply devices can collectively supply operating power for the TOP sensing implant.

While batteries can hold much greater amounts of energy than capacitors, capacitors offer the advantage of being capable of being re-charged very quickly, such as within just seconds or less. This characteristic is especially advantageous for supercapacitors because of their relatively large energy storage capacity as compared to other types of capacitors. Supercapacitors are capable of storing 1-2 orders of magnitude, or more, of energy per unit volume or mass than, for example, electrolytic capacitors. Unlike a solid dielectric used by other capacitors, supercapacitors may also employ, for example, electrostatic double-layer capacitance and/or electrochemical pseudocapacitance in order to store energy. Some energy storage devices may possess combinations of physical, chemical, or behavioral properties that make their classification as a battery, capacitor, or super capacitor somewhat indeterminate. In some embodiments, a supercapacitor may be considered as having 1-2 orders of magnitude less storage capacity per unit volume or mass than a battery as well as the capability to be fully charged within a comparatively short time period, such as 1-10 seconds, by the application of an appropriate voltage.

The IOP sensing implant may include a circuit with separate physical connections to the battery and to the supercapacitor, such as one pair of pads for each power source. The circuit may also include a third, separate pair of pads for the inductor coil. When the external inductive field is present, the circuit may cause a voltage to be applied to both the supercapacitor and the battery, with a source current to charge both of them. The voltage may remain on while the external inductive field is present (the supercapacitor will charge relatively quickly to that voltage and the battery will continue to draw current for a longer period of time). The supercapacitor and battery can be connected to the same charge circuit in parallel with the same charging voltage applied. This configuration may be advantageous because it does not require complex charging circuitry. However, in other embodiments, there could also be two different charge circuits—one to charge the supercapacitor and another to charge the battery (possibly with different voltages and/or currents).

For discharging, in some embodiments the supercapacitor and the battery are not connected in parallel. Instead, the IOP sensing implant may be powered from the supercapacitor until its charge is depleted and then the implant may switch to use the battery. Alternatively, the supercapacitor may be used to charge the battery (while the battery powers the implant). This approach could introduce energy losses during the charging of the battery, but could be an advantageous approach if, for example, the self-discharge rate of the supercapacitor is high.

Figure 14A:
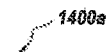
FIG. 14A illustrates a graph which shows the power usage of an example IOP sensing implant in the case where the implant is powered by a battery and, separately, for the case where the implant is powered by a supercapacitor.
Figure 14A:
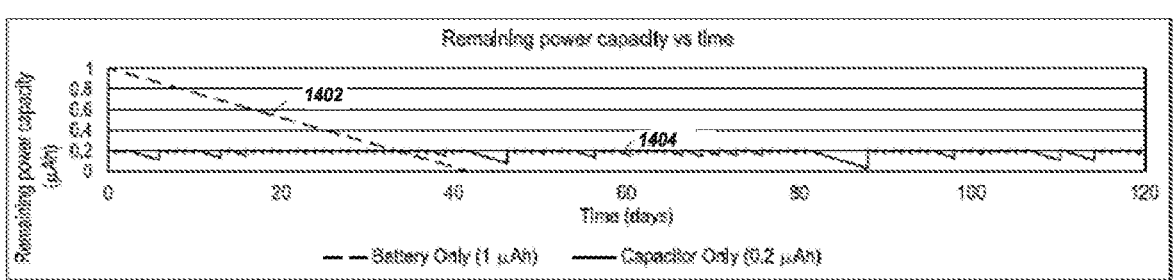

FIG. 14A is a graph 1400*a* which shows the power usage of an example IOP sensing implant in the case where the implant is powered by a battery (i.e., signal 1402) and, separately, for the case where the implant is powered by a supercapacitor (i.e., signal 1404). Signal 1402 illustrates the first case where the IOP sensing implant is powered solely by a battery. In this example, the IOP sensing implant is assumed to use 1 nAh of electrical energy per hour and the battery is assumed to have a usable storage capacity of 1 μAh. As shown by the signal 1402, the plotted remaining power capacity starts at 1 μAh and linearly decreases at a rate of 1 nAh per hour until all of the stored energy in the battery is exhausted after approximately 41 days.

Meanwhile, signal 1404 illustrates the second case where the TOP sensing implant is powered solely by a supercapacitor. In the case where the TOP sensing implant is powered at least partially by a supercapacitor, the TOP sensing implant may be part of a system which is designed to prompt the patient to perform charging interactions, or to more frequently perform charging interactions, with the TOP sensing implant. In such embodiments, an external charging device can be provided for wirelessly charging the TOP sensing implant. Wireless power transfer from the external device to the TOP sensing implant can be performed using electromagnetic energy, such as radio frequency (RF) energy, infrared (IR) energy, or the like. The electromagnetic energy can be transferred by, for example, inductive coupling, propagating waves, or the like. The external charging device can include, for example, a charging power source, a transmitter, and a coil or inductive coupling element. The TOP sensing implant can likewise include a coil or inductive coupling element to receive power from the external charging device.

In addition, the external charging device can also include an output device, such as a speaker, a display, a haptic transducer, or other related components. The output device can be used by the external charging device to provide prompts to the patient to perform charging interactions with the TOP sensing implant. Such prompts can be provided at regular intervals, such as daily, every 12 hours, weekly, or the like. Or the prompts can be provided at irregular intervals based on some criterion, such as when the supercapacitor has a predetermined percentage of power capacity remaining. The prompts may take the form of, for example, an audible cue, such as an alarm. In other embodiments, the prompt may be a visual cue, such as a certain symbol or text on a display. In still other embodiments, the prompt may take some other form, such as, for example, a haptic cue.

A charging interaction prompt can coincide with a timer synchronization prompt and/or a data download prompt. In such embodiments, use of a supercapacitor power source may have a synergistic effect because the user may already be required to perform regular timer synchronization interactions due to time-keeping drift onboard the TOP sensing implant, as discussed herein, and/or data downloads due to limited memory capacity using, for example, inductive coupling. These interactions can be taken advantage of to also charge the supercapacitor. Accordingly, it may be possible to eliminate or reduce the frequency, and associated inconvenience, of battery recharges, which may otherwise require 30-45 minutes of wearing a special charging device.

The charging interactions themselves can take many forms. For example, the patient may be required to manipulate a control on the external charging device, such as a button, switch, or other related feature. Manipulation of the control can cause the external charging device to initiate the wireless transfer of power from the external charging device to the TOP sensing implant. The control can also initiate the synchronization of timekeeping devices, the downloading of data from the TOP sensing implant, or the like, as discussed elsewhere herein.

In some embodiments, the external charging device may include or be accompanied by usage instructions which indicate to the user that he or she should bring the external charging device in proximity to his or her eye as part of the charging interaction. Closer physical proximity between the external power charging device and the TOP sensing implant will generally improve power transfer to the implant. In some embodiments, the external charging device may repeatedly or continuously provide the prompt until sensing that the user has carried out the charging interaction. Since the power source is a supercapacitor, the charging interaction may only take seconds or less, thus making it practical to conduct frequent charging interactions.

In some embodiments, the external charging device may be set to provide the charging prompt at intervals of time such that the expected energy usage of the TOP sensing implant during the interval is less than the storage capacity of the supercapacitor. For example, for the case illustrated by signal 1404, the TOP sensing implant is assumed to use 1 nAh of electrical energy per hour and the supercapacitor is assumed to have a usable storage capacity of 0.2 μAh. Thus, the supercapacitor can provide sufficient energy to power the TOP sensing implant for several days. So long as the external charging device prompts the user to conduct charging interactions with the TOP sensing implant at intervals which are shorter than this expected operation time (and assuming the user actually conducts the prompted charging interactions), then the TOP sensing implant can operate continuously. For example, signal 1404 shows that charging interactions are prompted—and generally performed—daily. However, even if the patient ignores the charging interaction prompt for a few days at a time (as indicated by the larger teeth in the sawtooth signal waveform 1404), the TOP sensing implant can still be operated continuously because the supercapacitor is capable of storing adequate energy to power the device for a few days at a time. The expected energy usage of the TOP sensing implant can be determined in a variety of ways, including experimentally during typical usage conditions or analytically based on rated power usage of the various components of the sensing implant.

Figure 14B:
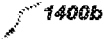
FIG. 14B illustrates a graph which shows the power usage of an example IOP sensing implant that is powered by the combination of a battery and a supercapacitor, where the capacity of the supercapacitor is less than the power usage of the implant between charging interaction times.
Figure 14B:
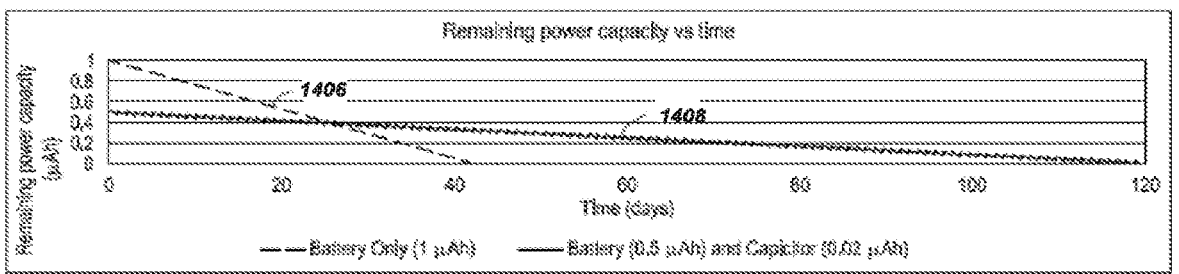

FIG. 14B is a graph 1400b which shows the power usage of an example IOP sensing implant that is powered by the combination of a battery and a supercapacitor, where the capacity of the supercapacitor is less than the power usage of the implant between charging interaction times. In the example illustrated by signal 1408, the IOP sensing implant consumes 1 nAh of electrical power per hour, while the battery has a storage capacity of 0.5 µAh and the supercapacitor has a storage capacity of 0.02 µAh. As just described with respect to FIG. 14A, the IOP sensing implant can be part of a system which includes an external charging device which occasionally prompts the patient to perform a charging interaction to charge the supercapacitor. (As mentioned above, the charging interaction prompt can also serve as, or coincide with, timer synchronization prompts and/or data download prompts.) In the example illustrated by signal 1408, the external charging device outputs the charging interaction prompt daily and the supercapacitor is therefore re-charged daily so long as the patient adheres to the prompt. This is evident from the 0.02 µAh sawtooth pattern which is evident in the signal 1408, where the supercapacitor is charged and then drops in remaining capacity until being re-charged once again. The 0.02 µAh storage capacity of the supercapacitor in this example is slightly less than the expected energy usage of 0.024 µAh by the IOP sensing implant between the daily charging interaction times.

For comparison purposes, FIG. 14B also includes a signal 1406, which illustrates a case where the IOP sensing implant is powered solely by a battery with a storage capacity of 1 µAh—double the storage capacity of the battery represented by signal 1408. As shown by the signal 1406, this battery capacity is sufficient to power the IOP sensing implant for approximately 41 days. But notwithstanding the fact that the battery corresponding to signal 1406 has twice the capacity as the battery corresponding to signal 1408, the IOP sensing implant corresponding to signal 1408 can operate approximately 3 times longer than the IOP sensing implant corresponding to signal 1406. This is due to the presence of the supercapacitor combined with regular or daily charging interaction. This example illustrates the synergy which can be achieved by using even a relatively small-capacity supercapacitor in conjunction with a battery to supply operating power to the IOP sensing implant.

Figure 14C:
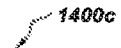
FIG. 14C illustrates a graph which shows the power usage of an example IOP sensing implant that is powered by the combination of a battery and a supercapacitor, where the capacity of the supercapacitor is greater than the power usage of the implant between charging interaction times.
Figure 14C:
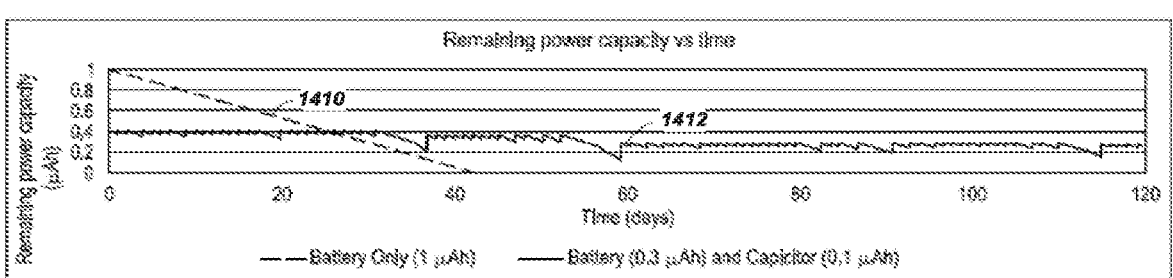

FIG. 14C is a graph 1400c which shows the power usage of an example IOP sensing implant that is powered by the combination of a battery and a supercapacitor, where the capacity of the supercapacitor is greater than the power usage of the implant between charging interaction times. In the example illustrated by signal 1412, the TOP sensing implant once again consumes 1 nAh of electrical power per hour, while the battery has a storage capacity of only 0.3 µAh and the supercapacitor has a storage capacity of 0.1

µAh. Once again, the TOP sensing implant can be part of a system which includes an external charging device which occasionally prompts the patient to perform a charging interaction to charge the supercapacitor. In the example illustrated by signal 1412, the external charging device outputs the charging interaction prompt daily and the supercapacitor is therefore generally re-charged daily, though allowance is made for these charging interactions to be occasionally skipped.

For comparison purposes, FIG. 14C also includes a signal 1410, which illustrates a case where the TOP sensing implant is powered solely by a battery with a storage capacity of 1 µAh—more than three times the storage capacity of the battery represented by signal 1412. As shown by the signal 1410, this battery capacity is sufficient to power the TOP sensing implant for approximately 41 days. In contrast, the TOP sensing implant corresponding to signal 1412 can operate for much longer periods of time because the supercapacitor is capable of supplying all of the necessary operating power for the entire period of time between scheduled charging interaction prompts. So long as the patient adheres to these prompts and carries out the charging interactions, the battery power is not needed. However, the battery is available to supply back-up power in the event that the patient fails to adhere to one or more charging interaction prompts.

Figure 15:
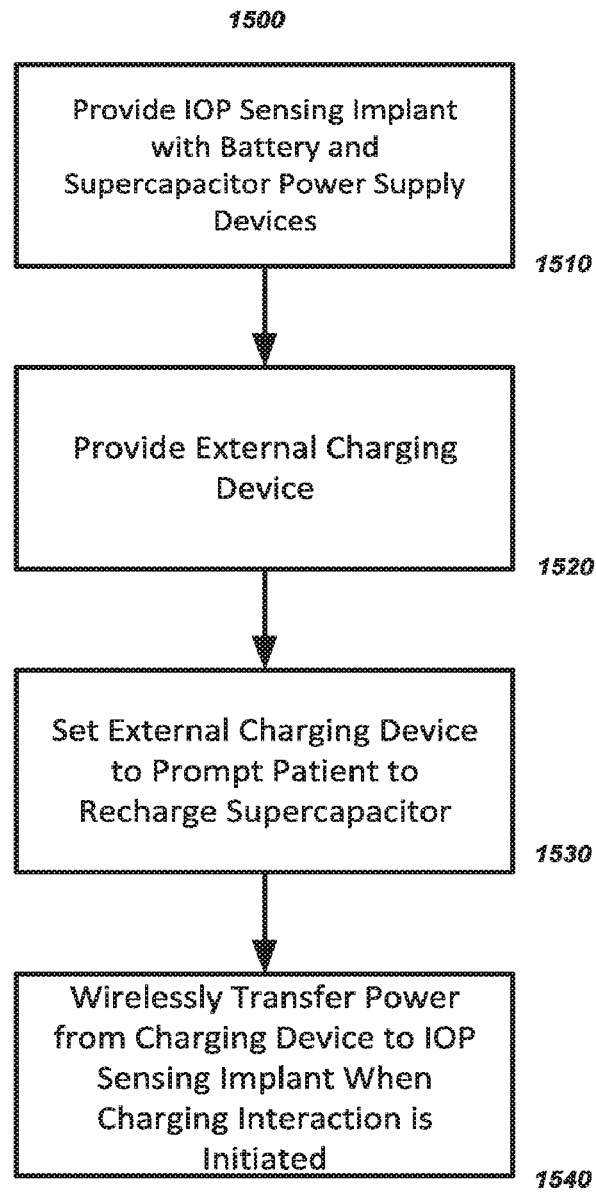
FIG. 15 illustrates a flowchart which illustrates a method for supplying operating power to an IOP sensing implant.

FIG. 15 is a flowchart which illustrates a method 1500 for supplying operating power to an TOP sensing implant. The method 1500 begins at block 1510 where a battery and a supercapacitor are provided onboard the TOP sensing implant to provide operating power for the implant. At block 1520, an external charging device is provided. At block 1530, the external charging device is set to prompt the patient to initiate a charging interaction between the external charging device and the TOP sensing implant. Finally, at block 1540, the external charging device wirelessly transfers power to, for example, a supercapacitor onboard the TOP sensing implant when a charging interaction is initiated. As already discussed, charging interactions can be prompted by the external charging device at, for example, regular intervals or based on satisfaction of some criterion.

Various embodiments of implantable physiological sensors, and associated methods, with a variety of features, have been described herein. Although not every embodiment has been illustrated with every feature, it should be understood that the features described herein can be freely combined with the various embodiments that are described and illustrated. The various physiological sensors described herein can also have any feature, characteristic, element, or the like that is disclosed in connection with the sensor devices described in the following U.S. patent documents, which are each hereby incorporated by reference in their entirety: U.S. Pat. Nos. 6,981,958; 7,678,065; U.S. Patent Publication No. 2010/0056979; and U.S. Patent Publication No. 2010/0106073. In addition, the various physiological sensors described herein can be used in, for example, any manner or application that is described in the foregoing patent documents.

The various illustrative devices, logical blocks, modules, circuits, and algorithm steps described in connection with the embodiments disclosed herein can be implemented as, for example, electronic hardware, such as analog and/or digital circuitry, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

Some of the various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein.

Embodiments have been described in connection with the accompanying drawings. However, it should be understood that the figures are not necessarily drawn to scale. Distances, angles, and other dimensions are merely illustrative and do not necessarily bear an exact relationship to actual dimensions and layout of the devices illustrated. In addition, the foregoing embodiments have been described at a level of detail to allow one of ordinary skill in the art to make and use the devices, systems, and methods described herein. A wide variety of variation is possible. Components, elements, and/or steps can be altered, added, removed, or rearranged. While certain embodiments have been explicitly described, other embodiments will become apparent to those of ordinary skill in the art based on this disclosure. The scope of certain inventions disclosed herein is indicated by the appended claims rather than by the foregoing description. All changes which come within the meaning and range of equivalency of the claims are to be embraced within their scope.

What is claimed is:

1. A method of implanting an intraocular implant, wherein the intraocular implant comprises:
    a housing comprising an aperture configured to receive an anchor, the housing further comprising a faceplate,
    a physiological sensor including a flexible diaphragm that forms a unitary body with the faceplate, and
    an anchor comprising a penetrating head and an elongate body,
    the method comprising:
        inserting the anchor into the aperture of the housing and securing the anchor to the housing; and
        implanting the intraocular implant into the eye by penetrating the penetrating head-into ocular tissue.

2. The method of claim 1, wherein the anchor further comprises a retention head wherein a maximum diameter of the retention head is greater than a diameter of the aperture, and the retention head comprises a gap through a center of the retention head, configured to allow a diameter of the retention head to be reduced from the maximum diameter, and wherein inserting the anchor into the aperture of the housing comprises:
    squeezing the retention tip to reduce the diameter of the retention head,
    inserting the anchor into the aperture while the diameter of the retention head is reduced, and translating the retention head through the aperture until the elongate body is disposed within the aperture.

3. The method of claim 1, wherein the aperture comprises a through hole from a first side of the housing to a second side of the housing.

4. The method of claim 1, wherein the anchor is removably coupled to the housing.

5. The method of claim 1, wherein the anchor is permanently affixed to the housing.

6. The method of claim 1, wherein the anchor comprises one or more in-flow outlets and one or more out-flow outlets.

7. The method of claim 1, wherein the housing includes a geometric profile that matches a geometric profile of the anchor to prevent twisting of the anchor relative to the housing.

8. The method of claim 1, wherein the housing includes one or more protrusions or grooves to facilitate the flow of aqueous humor around the housing.

9. The method of claim 3, wherein the through hole is positioned outside a central third of the housing.

10. The method of claim 1, wherein the anchor is a drug eluting anchor.

11. The method of claim 1, wherein the anchor is a drug eluting anchor and wherein the anchor has one or more fluid flow passageways.

12. The method of claim 1, wherein the implanting the intraocular implant occurs after the securing the anchor to the housing.

13. A method of implanting an intraocular implant, wherein the intraocular implant comprises:
    a housing comprising a physiological sensor integrated with the housing, wherein the housing comprises a faceplate and the physiological sensor comprises a flexible diaphragm that forms a unitary body with the faceplate, and
    an anchor comprising a penetrating head, an elongate body, and an out-flow outlet,
    the method comprising:
        penetrating the anchor into a physiological aqueous humor outflow pathway; and
        positioning the out-flow outlet of the anchor in the physiological aqueous humor outflow pathway.

14. A method of implanting an intraocular implant, wherein the intraocular implant comprises:
    a housing comprising a faceplate,
    a physiological sensor including a flexible diaphragm that forms a unitary body with the faceplate, and
    an anchor comprising a penetrating head and an elongate body,
    the method comprising:
        implanting the intraocular implant into the eye by penetrating the penetrating head into ocular tissue.

15. The method of claim 14, wherein the faceplate and the flexible diaphragm are formed from silicon.

16. The method of claim 14, wherein the intraocular implant is implanted into an iridocorneal angle of the eye.

17. The method of claim 14, wherein the faceplate comprises a contoured surface.

* * * * *